US012569608B2

(12) United States Patent
Fischell et al.

(10) Patent No.: US 12,569,608 B2
(45) Date of Patent: Mar. 10, 2026

(54) CATHETER-BASED EXTRACORPOREAL MEMBRANE OXYGENATION (ECMO)

(71) Applicant: VivaCath, Inc., San Jose, CA (US)

(72) Inventors: Tim A. Fischell, Kalamazoo, MI (US);
Frank Saltiel, Kalamazoo, MI (US);
Jeffrey Payne, Temecula, CA (US)

(73) Assignee: VivaCath, Inc., San Jose, CA (US)

( * ) Notice: Subject to any disclaimer, the term of this
patent is extended or adjusted under 35
U.S.C. 154(b) by 0 days.

(21) Appl. No.: 19/264,838

(22) Filed: Jul. 9, 2025

(65) Prior Publication Data

US 2025/0339600 A1     Nov. 6, 2025

Related U.S. Application Data

(63) Continuation-in-part of application No.
PCT/US2025/025872, filed on Apr. 22, 2025, which
is a continuation-in-part of application No.
19/056,723, filed on Feb. 18, 2025, and a
continuation-in-part of application No.
PCT/US2024/050853, filed on Oct. 10, 2024, and a
continuation-in-part of application No. 18/642,779,
filed on Apr. 22, 2024, now Pat. No. 12,226,564.

(51) Int. Cl.
*A61M 1/36*          (2006.01)
(52) U.S. Cl.
CPC ...  *A61M 1/3659* (2014.02); *A61M 2202/0021*
(2013.01); *A61M 2202/0413* (2013.01); *A61M*
*2205/10* (2013.01); *A61M 2210/125* (2013.01);
*A61M 2210/127* (2013.01)
(58) Field of Classification Search
CPC .............. A61M 1/3659; A61M 1/3661; A61M 1/3666; A61M 1/3667; A61M 1/1698;
A61M 25/10; A61M 2025/0004; A61M
2210/125; A61M 2210/127
See application file for complete search history.

(56) References Cited

U.S. PATENT DOCUMENTS

| | | |
|---|---|---|
| 5,186,713 A | 2/1993 | Raible |
| 6,673,041 B1 | 1/2004 | Macoviak |
| 6,709,418 B1 | 3/2004 | Aboul-Hosn et al. |

(Continued)

FOREIGN PATENT DOCUMENTS

| | | |
|---|---|---|
| WO | WO2021/167653 A1 | 8/2021 |
| WO | WO2022/271999 A1 | 12/2022 |

(Continued)

OTHER PUBLICATIONS

Fischell et al.; U.S. Appl. No. 19/146,216 entitled "Apparatuses for
antegrade transcatheter valve repair or implanation," filed Jul. 7,
2025.

*Primary Examiner* — Philip R Wiest
(74) *Attorney, Agent, or Firm* — Shay Glenn LLP

(57) ABSTRACT

Apparatuses and methods for performing transseptal extra-
corporeal membrane oxygenation are disclosed. The method
may include puncturing a septum between the right atrium
and the left atrium and advancing a catheter system through
the puncture and into the aorta. The catheter system may
include coaxially arranged and independently moveable
venous and arterial sheaths having independently position-
able openings for removing blood from the patient and for
returning oxygenated blood to the patient, e.g., within the
aorta.

20 Claims, 64 Drawing Sheets

(56) References Cited

U.S. PATENT DOCUMENTS

| | | | |
|---|---|---|---|
| 6,814,713 | B2 | 11/2004 | Aboul-Hosn et al. |
| 6,935,344 | B1 | 8/2005 | Aboul-Hosn et al. |
| 8,591,460 | B2 | 11/2013 | Wilson et al. |
| 9,168,352 | B2 | 10/2015 | Kelly et al. |
| 9,764,118 | B2 | 9/2017 | Anderson et al. |
| 10,307,575 | B2 | 6/2019 | Alaswad |
| 11,304,803 | B2 | 4/2022 | Huber |
| 11,491,313 | B2 | 11/2022 | Fischell et al. |
| 11,759,315 | B1 | 9/2023 | Fischell et al. |
| 11,766,328 | B1 | 9/2023 | Fischell et al. |
| 11,925,554 | B1 | 3/2024 | Fischell et al. |
| 11,964,091 | B1 | 4/2024 | Fischell et al. |
| 12,186,189 | B2 | 1/2025 | Fischell et al. |
| 12,226,564 | B1 | 2/2025 | Fischell et al. |
| 12,390,328 | B2 | 8/2025 | Fischell et al. |
| 12,390,572 | B2 | 8/2025 | Fischell et al. |
| 2003/0149395 | A1 | 8/2003 | Zawacki |
| 2009/0005725 | A1 | 1/2009 | Shorey |
| 2009/0112050 | A1 | 4/2009 | Farnan et al. |
| 2009/0149950 | A1 | 6/2009 | Wampler |
| 2010/0331939 | A1 | 12/2010 | Elencwajg |

| | | | | |
|---|---|---|---|---|
| 2011/0152741 | A1 | 6/2011 | Banchieri et al. | |
| 2016/0082176 | A1 | 3/2016 | Kelly et al. | |
| 2018/0126127 | A1 | 5/2018 | Devereux et al. | |
| 2019/0255299 | A1 | 8/2019 | Fischell et al. | |
| 2019/0307996 | A1* | 10/2019 | Alaswad | A61M 60/216 |
| 2020/0147343 | A1 | 5/2020 | Fabro | |
| 2020/0179661 | A1 | 6/2020 | Fischell et al. | |
| 2020/0254166 | A1 | 8/2020 | Stack et al. | |
| 2020/0409239 | A1 | 12/2020 | Ito | |
| 2021/0077084 | A1 | 3/2021 | Stack | |
| 2021/0220131 | A1* | 7/2021 | Stack | A61F 2/2427 |
| 2021/0402138 | A1 | 12/2021 | Kelly et al. | |
| 2022/0047303 | A1 | 2/2022 | Willis et al. | |
| 2022/0273853 | A1 | 9/2022 | Heilmann et al. | |
| 2022/0305250 | A1 | 9/2022 | Heilmann | |
| 2022/0323663 | A1 | 10/2022 | Heilmann | |
| 2022/0355065 | A1 | 11/2022 | Ardehali | |
| 2025/0186669 | A1 | 6/2025 | Fischell et al. | |

FOREIGN PATENT DOCUMENTS

| | | | |
|---|---|---|---|
| WO | WO2024/077290 | A1 | 4/2024 |
| WO | WO2025/080895 | A1 | 4/2025 |

* cited by examiner

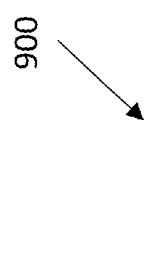
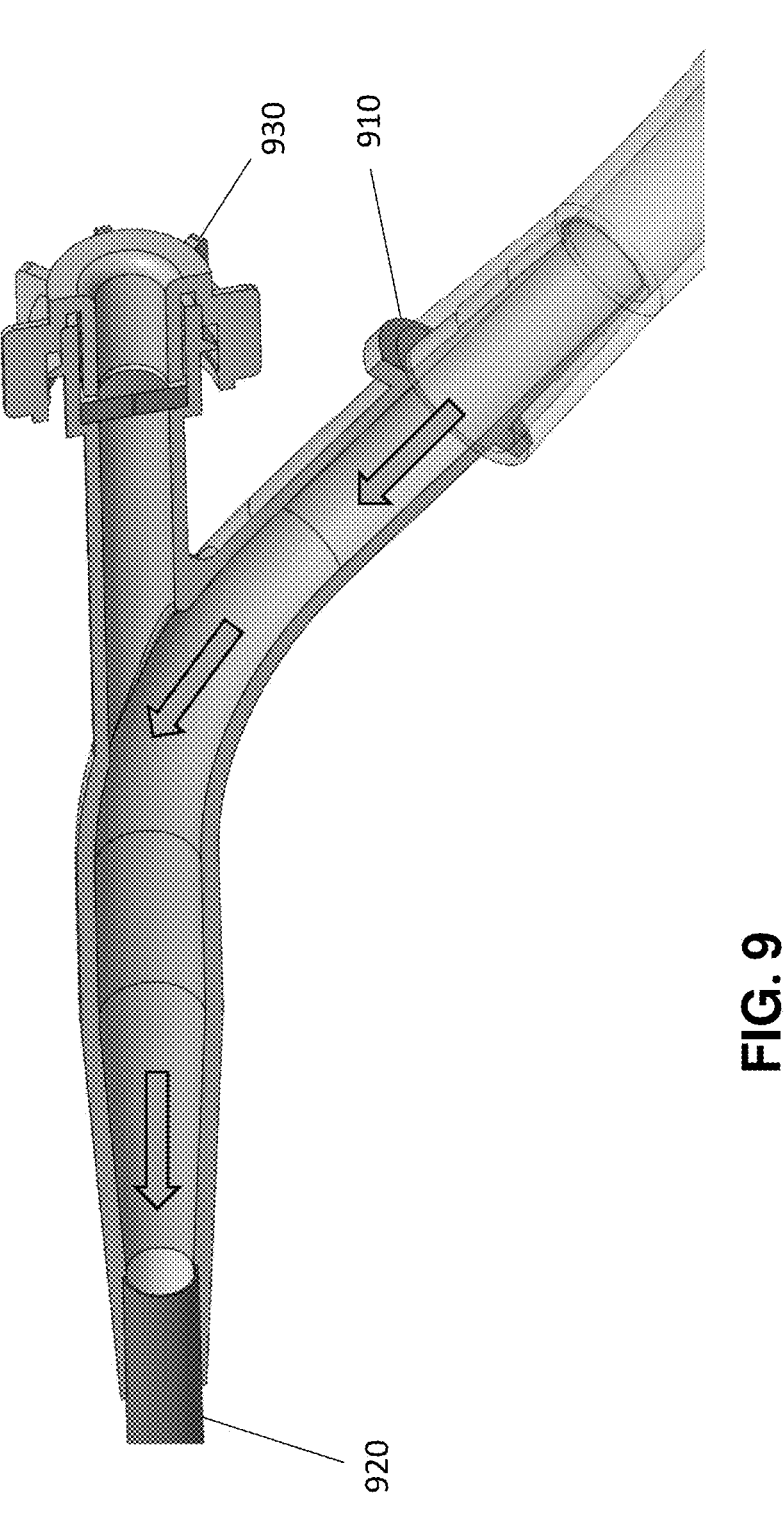
FIG. 9

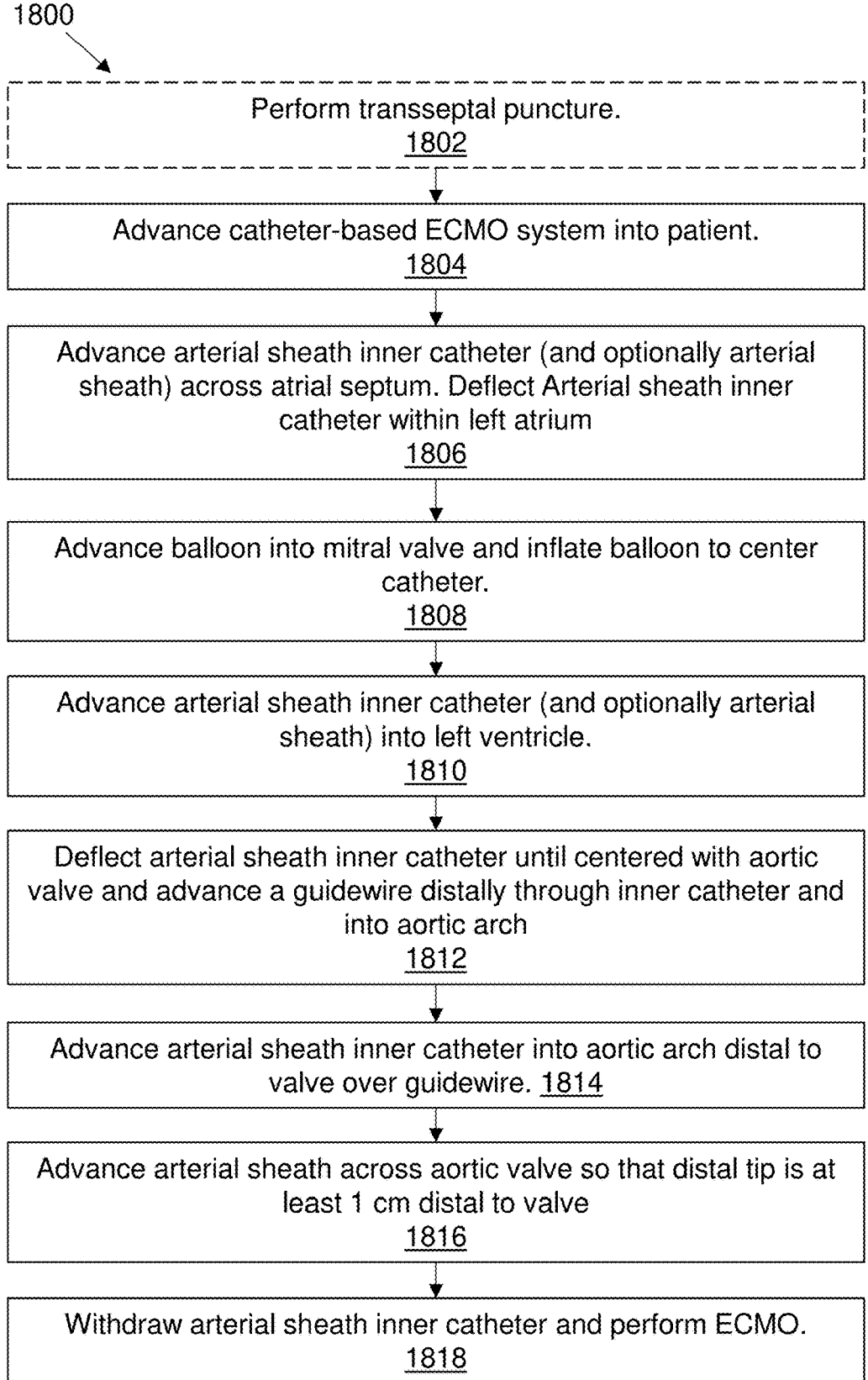

Perform transseptal puncture.
1802

Advance catheter-based ECMO system into patient.
1804

Advance arterial sheath inner catheter (and optionally arterial sheath) across atrial septum. Deflect Arterial sheath inner catheter within left atrium
1806

Advance balloon into mitral valve and inflate balloon to center catheter.
1808

Advance arterial sheath inner catheter (and optionally arterial sheath) into left ventricle.
1810

Deflect arterial sheath inner catheter until centered with aortic valve and advance a guidewire distally through inner catheter and into aortic arch
1812

Advance arterial sheath inner catheter into aortic arch distal to valve over guidewire. 1814

Advance arterial sheath across aortic valve so that distal tip is at least 1 cm distal to valve
1816

Withdraw arterial sheath inner catheter and perform ECMO.
1818

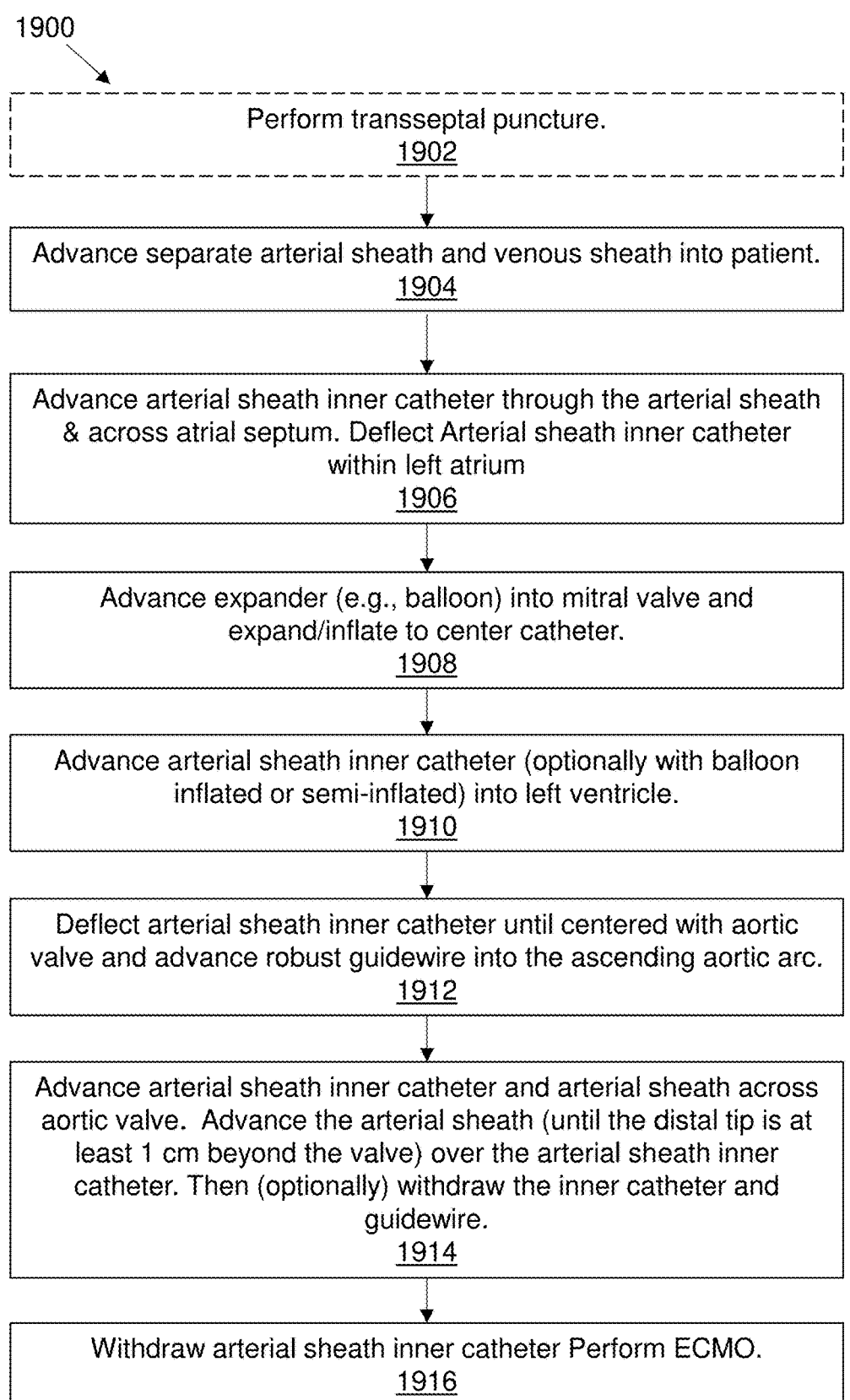

Perform transseptal puncture.
1902

Advance separate arterial sheath and venous sheath into patient.
1904

Advance arterial sheath inner catheter through the arterial sheath & across atrial septum. Deflect Arterial sheath inner catheter within left atrium
1906

Advance expander (e.g., balloon) into mitral valve and expand/inflate to center catheter.
1908

Advance arterial sheath inner catheter (optionally with balloon inflated or semi-inflated) into left ventricle.
1910

Deflect arterial sheath inner catheter until centered with aortic valve and advance robust guidewire into the ascending aortic arc.
1912

Advance arterial sheath inner catheter and arterial sheath across aortic valve.  Advance the arterial sheath (until the distal tip is at least 1 cm beyond the valve) over the arterial sheath inner catheter. Then (optionally) withdraw the inner catheter and guidewire.
1914

Withdraw arterial sheath inner catheter Perform ECMO.
1916

FIG. 19

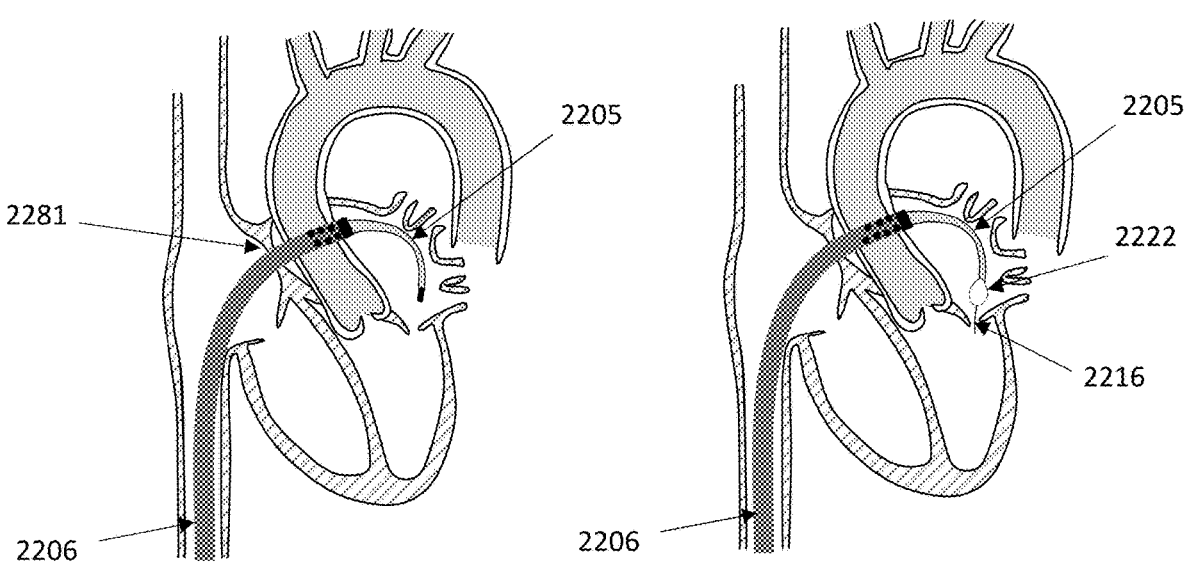
FIG. 22A
FIG. 22B
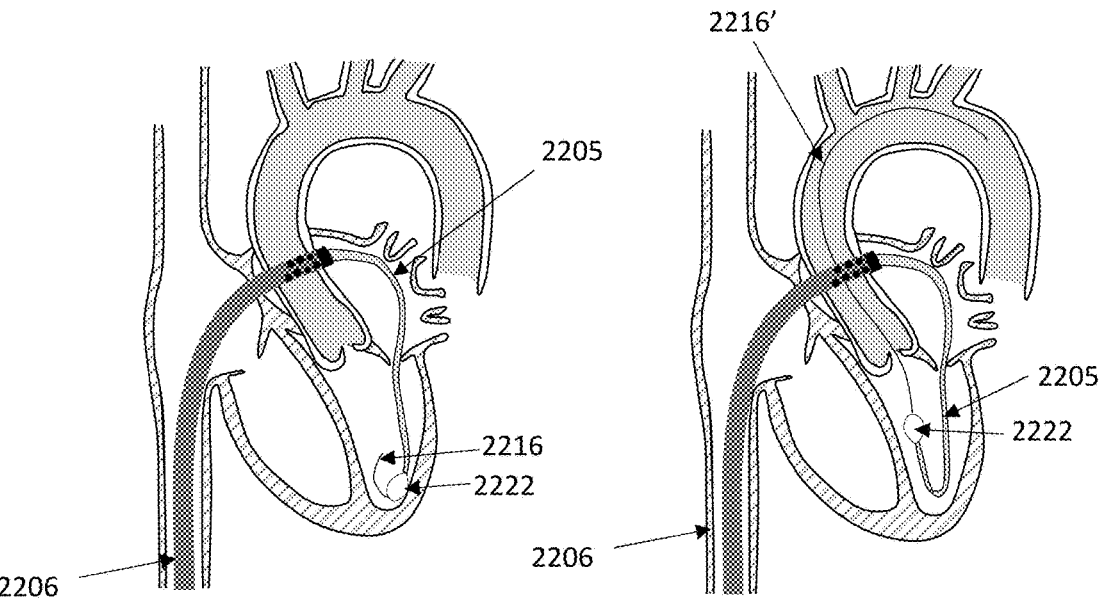
FIG. 22C
FIG. 22D

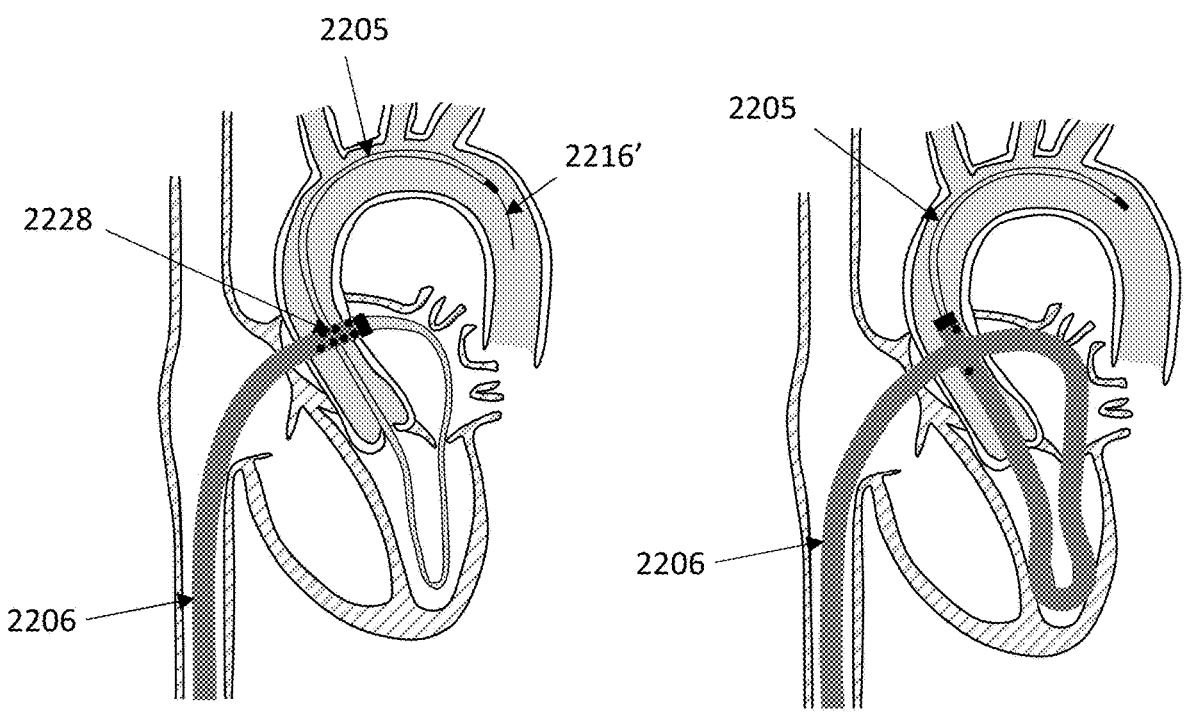
FIG. 22E
FIG. 22F
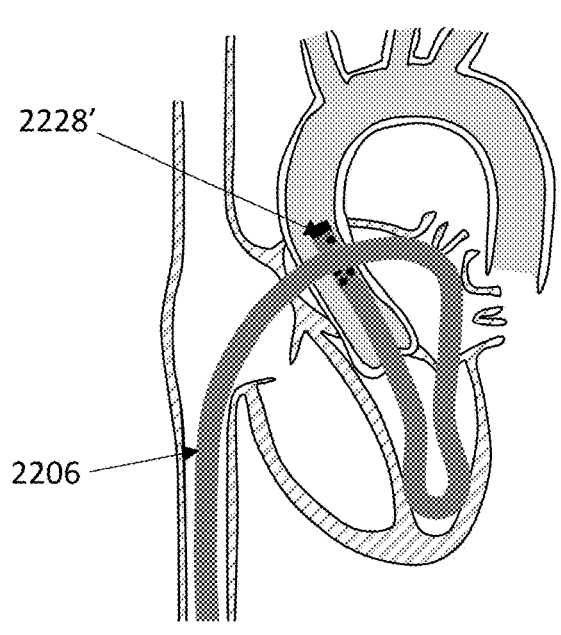
FIG. 22G

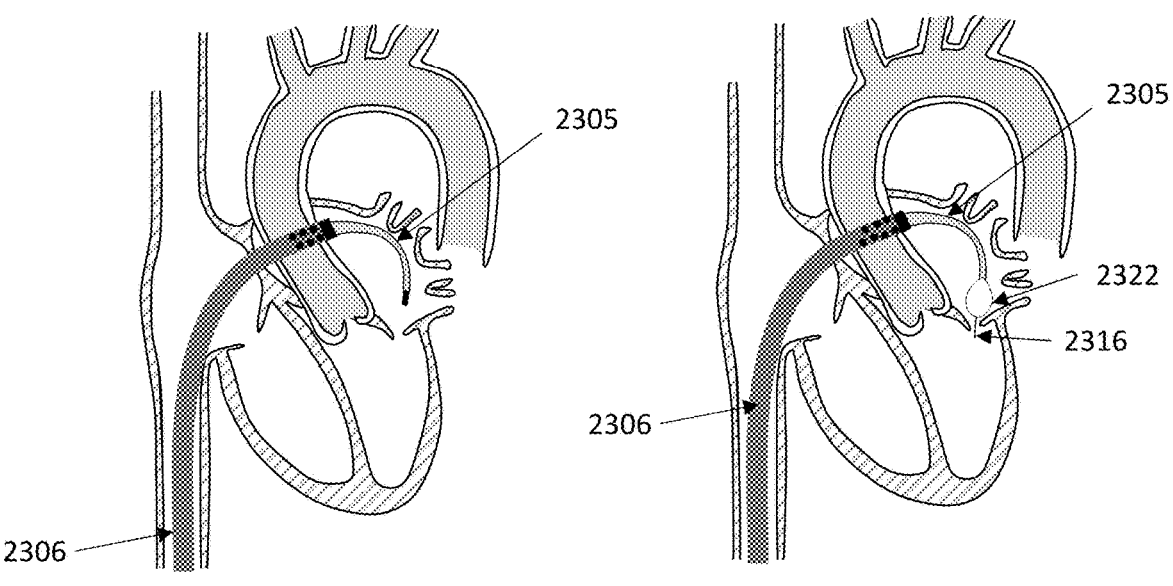
FIG. 23A
FIG. 23B
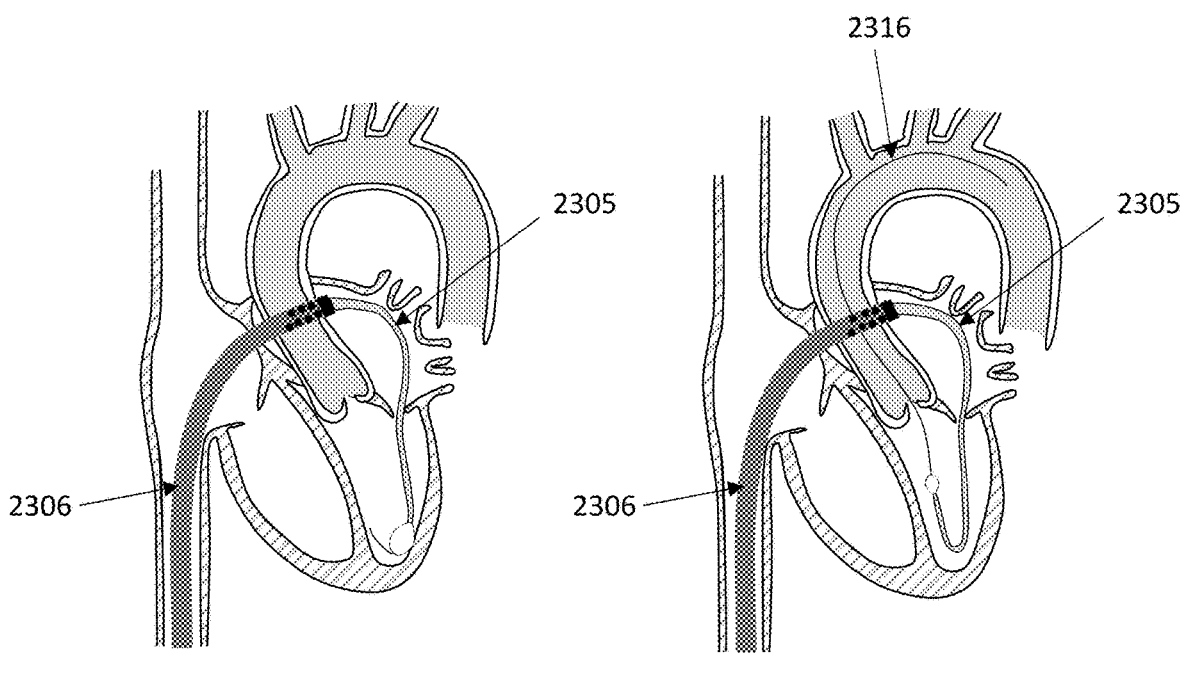
FIG. 23C
FIG. 23D

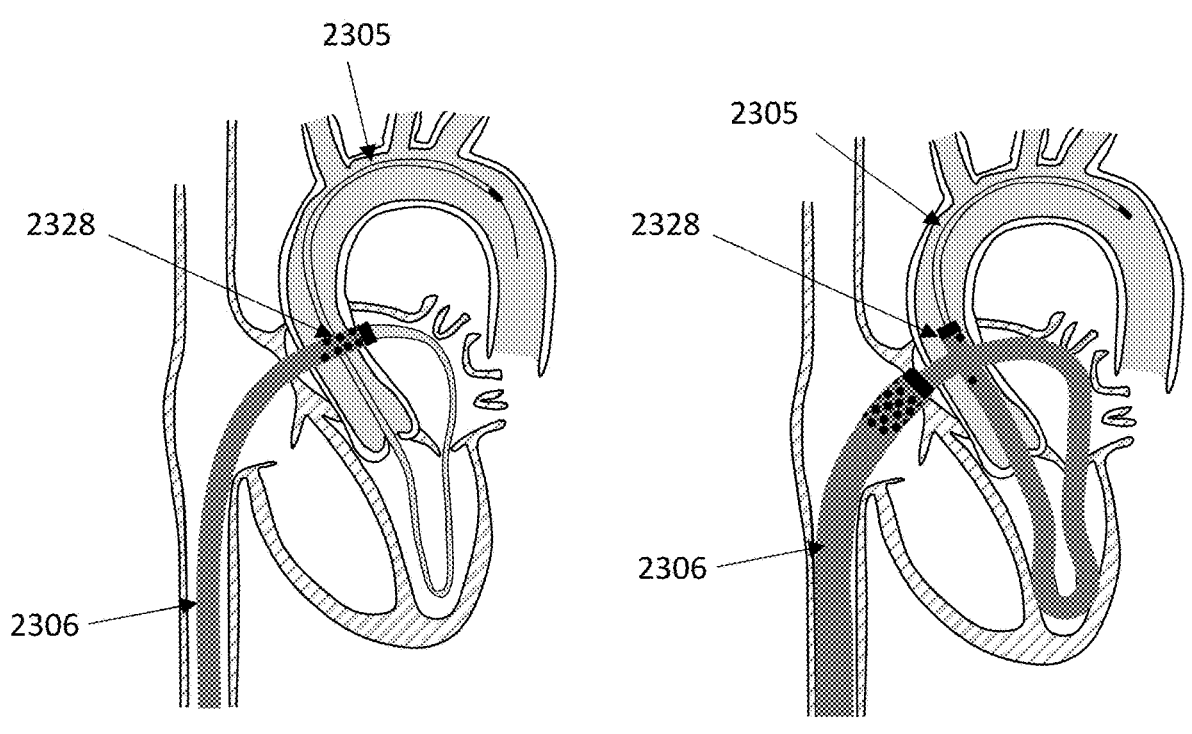
FIG. 23E
FIG. 23F
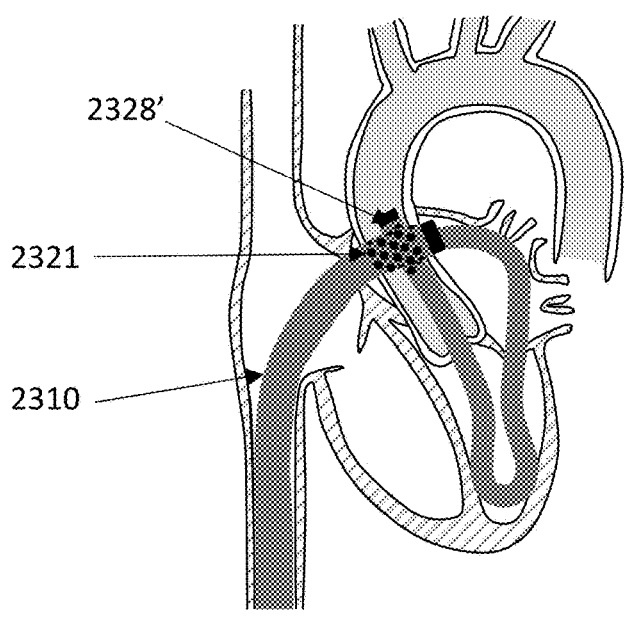
FIG. 23G

Deflection length = 4-5cm

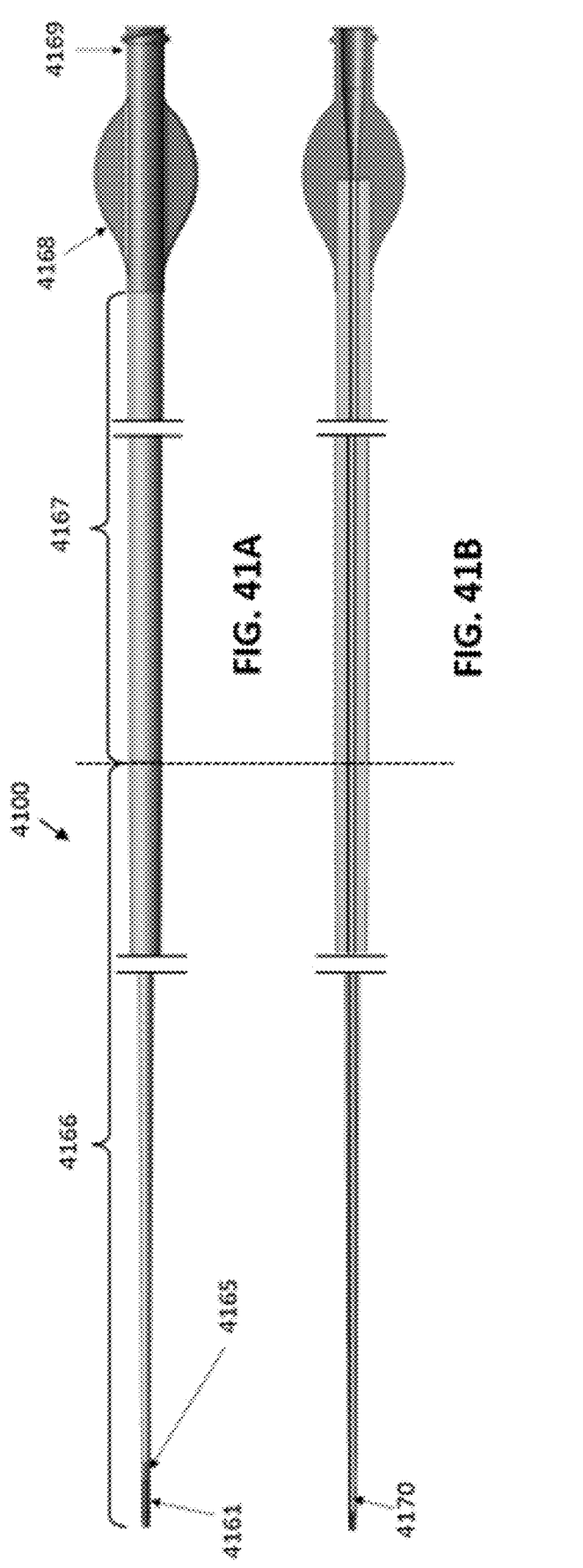
FIG. 41A
FIG. 41B
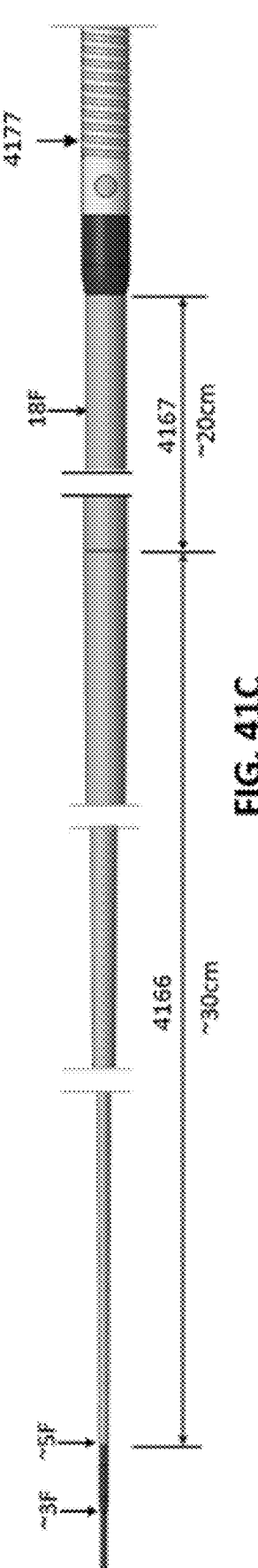
FIG. 41C 4585    4561    4534    4561

4561    4581

4585

4535

4561

CATHETER-BASED EXTRACORPOREAL MEMBRANE OXYGENATION (ECMO)

CLAIM OF PRIORITY

This patent application claims priority as a continuation-in-part to International Patent Application No. PCT/US2025/025872, titled "CATHETER-BASED EXTRACORPOREAL MEMBRANE OXYGENATION (ECMO)," and filed on Apr. 22, 2025, which claims priority to U.S. patent application Ser. No. 19/056,723, filed on Feb. 18, 2025, titled "METHOD AND APPARATUS FOR CATHETER-BASED EXTRACORPOREAL MEMBRANE OXYGENATION (ECMO)," now U.S. Patent Application Publication No. 2025/0186669, to U.S. patent application Ser. No. 18/642,779, filed on Apr. 22, 2024, titled "METHOD AND APPARATUS FOR CATHETER-BASED EXTRACORPOREAL MEMBRANE OXYGENATION (ECMO)," now U.S. Pat. No. 12,226,564, and to International Patent Application No. PCT/US2024/050853, filed on Oct. 10, 2024, titled "METHOD AND APPARATUS FOR CATHETER-BASED EXTRACORPOREAL MEMBRANE OXYGENATION (ECMO)," now International Publication No. WO 2025/080895. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein may be related to extracorporeal membrane oxygenation (ECMO). More specifically, the methods and apparatuses described herein may relate to apparatuses that may enable a surgeon to perform ECMO procedures through a catheter guided to a patient's heart region.

BACKGROUND

Historically, heart lung bypass techniques have been used as a core technology for performing open heart surgeries such as coronary bypass grafting, or complex valve replacement or repair. These procedures are typically done in the operating room with an open chest and cannulas inserted into the heart structures, such as the right atrium, and aorta.

Percutaneous, extracorporeal membrane oxygenation (ECMO) using catheter-based systems have been used for short-term ECMO for critically ill patients with cardiopulmonary disease. Conventionally, a large bore sheath or cannula that is placed in the femoral vein, which can be advanced into the iliac vein or possibly the inferior vena cava to allow a high flow removal of deoxygenated venous blood. The blood is then pumped to an extracorporeal membrane oxygenator that oxygenates the blood. A second large bore cannula is placed in the femoral artery, and this is attached to the outflow from the membrane oxygenator and pump to perfuse this oxygenated blood into the iliac artery or distal abdominal aorta. This type of system is commonly referred to as "VA (venous-arterial) ECMO".

Conventional ECMO has been associated with complications that lead to critical limb ischemia secondary to large bore arterial cannula/catheters. These complications can occur in up to ten percent of conventional ECMO procedures and are associated with a higher mortality. Thus, there is a critical need for an improved technology to better enable catheter-based cardiopulmonary bypass/ECMO.

SUMMARY OF THE DISCLOSURE

Described herein are apparatuses, systems, and methods to provide ECMO therapies to a patient. The therapies may be delivered through one or more catheters that are percutaneously delivered and are advanced to the heart region. In some examples, at least one catheter may be advanced through a transseptal puncture, advanced through the left atrium, left ventricle, and into the aorta. Blood may be removed through a venous catheter positioned in the inferior vena cava and returned through an arterial catheter in the aorta.

Any of the methods described herein may be used for transseptal extracorporeal membrane oxygenation. The method may include advancing a first inner catheter that is distally tapered and a second inner catheter through a transseptal puncture, wherein the second inner catheter is coaxial with and surrounds the first inner catheter and an outer surface of the second inner catheter is flush with an outer surface of the first inner catheter, deflecting the first inner catheter within the left atrium so that a distal tip of the first inner catheter is disposed substantially toward an approximate center of a mitral valve, advancing the first inner catheter and the second inner catheter through the approximate center of the mitral valve, deflecting the distal tip of the first inner catheter toward a valve, advancing the first inner catheter and the second inner catheter through the valve, withdrawing the first inner catheter, and receiving, from the patient, oxygen-poor blood through an outer catheter and returning oxygenated blood through the second inner catheter, wherein the outer catheter surrounds the second inner catheter.

Any of the methods described herein may further comprise inflating a balloon disposed around a distal end of the first inner catheter to center the first inner catheter with respect to the mitral valve. In general, the balloon may be inflated with a gas or a liquid, such as saline. Any of the methods described herein can also include inflating the balloon before advancing the first inner catheter and the second inner catheter through the mitral valve.

Any of the methods described herein, deflecting the distal tip of the first inner catheter toward a valve may include deflecting the distal tip by more than 170 degrees with respect to a proximal section of the first inner catheter. In general, the distal tip may be deflected by any feasible amount more than about 140 degrees or more (e.g., 150 degrees or more, 160 degrees or more, 170 degrees or more, etc.).

In any of the methods described herein, the second inner catheter may include a plurality of holes disposed around a body of the second inner catheter to return the oxygenated blood.

In any of the methods described herein, the outer catheter may include a plurality of holes disposed around a body of the outer catheter to receive the oxygen-poor blood (venous blood) and/or blood from the left atrium.

Any of the methods described herein can further include inserting a first guidewire through the first inner catheter, the second inner catheter, and the outer catheter prior to deflecting the first inner catheter within the left atrium. Furthermore, the method can include withdrawing the first guidewire prior to deflecting the distal tip of the first inner catheter toward the valve and inserting a second guidewire stiffer than the first guidewire, after withdrawing the first guidewire.

Any of the methods described herein can include puncturing the septum between the right atrium and the left atrium before advancing the first inner catheter and the second inner catheter through the transseptal puncture.

Example methods for transseptal extracorporeal membrane oxygenation can include advancing a first catheter that includes an inner sheath and an outer sheath through a transseptal puncture, wherein the outer sheath is coaxial with and surrounds the inner sheath and an outer surface of the outer sheath is flush with an outer surface of the inner sheath, advancing a second catheter into an inferior vena cava, deflecting the inner sheath within the left atrium so that a distal tip of the inner sheath is disposed substantially toward an approximate center of a mitral valve, advancing the inner sheath through the approximate center of the mitral valve, deflecting the distal tip of the inner sheath toward a valve, advancing the first catheter through the valve, withdrawing the inner sheath from the first catheter, and receiving, from the patient, oxygen-poor blood through the second catheter and returning oxygenated blood through the first catheter.

In any of the methods described herein can further include inflating a balloon disposed around a distal end of the inner sheath to center the first inner catheter with respect to the mitral valve. Furthermore, the methods may include inflating the balloon before advancing the inner sheath and the outer sheath through the mitral valve.

In any of the methods described herein, deflecting the distal tip of the inner sheath toward a valve may comprise deflecting the distal tip by more than about 140 degrees (e.g., about 150 degrees or more, about 160 degrees or more, about 170 degrees or more, etc.) with respect to a proximal section of the inner sheath.

In any of the methods described herein, the second catheter can include a plurality of holes disposed around a body of the second catheter to return the oxygenated blood. In a similar manner, in any of the methods described herein, the outer sheath can include a plurality of holes disposed around a body of the outer sheath to receive the oxygen-poor blood.

Any of the methods described herein can further include inserting a first guidewire through the inner sheath and the outer sheath prior to deflecting the inner sheath within the left atrium. Furthermore, any of the methods can further include withdrawing the first guidewire prior to deflecting the distal tip of the inner sheath toward the valve and inserting a second guidewire stiffer than the first guidewire, after withdrawing the first guidewire.

Any of the methods described herein can include puncturing the septum between the right atrium and the left atrium before advancing the inner sheath and the outer sheath through the transseptal puncture.

Also described herein are apparatuses (e.g., systems and devices) for performing any of these methods. In particular, described herein are system for performing transseptal extracorporeal membrane oxygenation (ECMO) on a patient. In some cases the system includes: a first inner catheter that is distally tapered; an arterial sheath catheter, wherein the arterial sheath catheter is configured to coaxially surround the first inner catheter so that a distal outer surface of the arterial sheath catheter is flush with an outer surface of the first inner catheter, further wherein the arterial sheath catheter comprises a plurality of arterial infusion holes at a distal end region of the first inner catheter; a venous sheath catheter, wherein the venous sheath catheter is configured to coaxially surround the arterial sheath catheter so that a distal outer surface of the venous sheath catheter is flush with an outer surface of the arterial sheath catheter, further wherein the venous sheath catheter comprises a plurality of lateral venous inflow holes through a sidewall region; a first proximal connector configured to couple a lumen of the arterial sheath catheter that is in fluid communication with the plurality of arterial infusion holes to an oxygenator; and a second proximal connector configured to couple a lumen of the venous sheath catheter that is in fluid communication with the plurality of lateral venous inflow holes to a venous aspiration pump.

In general, the inner catheter (either the first inner catheter and/or a second inner catheter) may be configured to be moved independent of the outer catheter, and may extend for 20 cm or more (e.g., 25 cm or more, 30 cm or more, 35 cm or more, 40 cm or more, 50 cm or more, 55 cm or more, etc., between 20-55 cm, between 25-50 cm, between 30-50 cm, etc.) beyond the distal tip of the outer catheter. In use, the inner catheter may be advanced, in some cases, all the way across the mitral valve around the apex and into the ascending aorta. Sequentially, the outer catheter would then be advanced over the inner catheter, once it has been advanced all the way past the mitral valve around the apex and into the aorta. Thus, the inner catheter may be configured so that an outer catheter may move freely (e.g., slide) over the inner catheter. The outer catheter may have a generally smooth shape. In some cases the inner catheter may be configured to limit the extension of the inner catheter distal to the outer catheter.

In some cases the first inner catheter may include a distal expandable dilator. For example, the distal expandable dilator may comprise a balloon. Any of these apparatuses may include a second inner catheter having a distal end region configured to be deflected between 140-190 degrees.

Any of these apparatuses may include a venous sheath hub comprising the second proximal connector, wherein the venous sheath catheter extends distally from the venous sheath hub. In some cases the apparatus may include an arterial sheath hub comprising the first proximal connector, wherein the arterial sheath catheter extends distally from the arterial sheath hub. The plurality of lateral venous inflow holes may be configured to be positioned within a patient's inferior vena cava when the plurality of arterial infusion holes is positioned within the patient's ascending aortic arch when the distal outer surface of the venous sheath catheter is flush with an outer surface of the arterial sheath catheter.

In any of these apparatuses, the sidewall region comprising the plurality of lateral venous inflow holes may be configured to be positioned across a patient's heart septum when the plurality of arterial infusion holes is positioned within the patient's ascending aortic arch when the distal outer surface of the venous sheath catheter is flush with an outer surface of the arterial sheath catheter.

Any of these apparatuses may include a first interference fit between a distal inner surface of the arterial sheath catheter and the outer surface of the first inner catheter. Any of these apparatuses may include a second interference fit between a distal inner surface of the venous sheath catheter and the outer surface of the arterial sheath catheter.

For example, described herein are systems for performing transseptal extracorporeal membrane oxygenation (ECMO) on a patient, the system comprising: a first inner catheter that is distally tapered; an arterial sheath catheter, wherein the arterial sheath catheter is configured to coaxially surround the first inner catheter so that a distal outer surface of the arterial sheath catheter is flush with an outer surface of the first inner catheter, further wherein the arterial sheath catheter comprises a plurality of arterial infusion holes at a distal end region of the first inner catheter; a venous sheath catheter, wherein the venous sheath catheter is configured to coaxially surround the arterial sheath catheter so that a distal outer surface of the venous sheath catheter is flush with an outer surface of the arterial sheath catheter, further wherein the venous sheath catheter comprises a plurality of lateral venous inflow holes through a sidewall region; an arterial hub in fluid communication with the plurality of arterial infusion holes; and a venous hub in fluid communication with the plurality of lateral venous inflow holes.

The arterial hub may be configured to couple a lumen of the arterial sheath catheter to a first connector. The venous hub may be configured to couple a lumen of the venous sheath catheter to a second connector. The first inner catheter may include a distal expandable dilator configured to center the first inner catheter within a patient's lumen. The arterial hub is configured to deliver oxygenated blood to the arterial infusion holes.

In some cases the venous hub is configured to receive oxygen-poor blood from the patient. The plurality of lateral venous inflow holes may be configured to be positioned within a patient's inferior vena cava when the plurality of arterial infusion holes is positioned within the patient's ascending aortic arch when the distal outer surface of the venous sheath catheter is flush with an outer surface of the arterial sheath catheter. The sidewall region comprising the plurality of lateral venous inflow holes may be configured to be positioned across a patient's heart septum when the plurality of arterial infusion holes is positioned within the patient's ascending aortic arch when the distal outer surface of the venous sheath catheter is flush with an outer surface of the arterial sheath catheter. Any of these apparatuses may include a second inner catheter having a distal end region configured to be deflected between 140-190 degrees. The arterial hub may be configured to be coupled to an oxygenator and the venous hub is configured to be coupled to a venous aspiration pump.

As mentioned, the inner catheter may be configured as a guide catheter, so that it may extend distal to the outer catheter to allow positioning of the inner catheter across the mitral valve around the apex and into the ascending aorta, and the outer catheter may then be advanced over the inner catheter and advanced all the way past the mitral valve around the apex and into the aorta.

In general, a system for performing transseptal extracorporeal membrane oxygenation (ECMO) on a patient may include: a first inner catheter that is distally tapered; a first sheath catheter, wherein the first sheath catheter is configured to coaxially surround the first inner catheter, further wherein the first sheath catheter comprises a plurality of infusion holes at a distal end region of the first inner catheter; a second sheath catheter, wherein the second sheath catheter is configured to coaxially surround the first sheath catheter so that a distal inner surface of the second sheath catheter is flush with an outer surface of the first sheath catheter, further wherein the second sheath catheter comprises a plurality of lateral inflow holes through a sidewall region; a first proximal connector configured to couple a lumen of the first sheath catheter that is in fluid communication with the plurality of infusion holes to an oxygenator or aspiration pump; and a second proximal connector configured to couple a lumen of the second sheath catheter that is in fluid communication with the plurality of lateral inflow holes to an aspiration pump or oxygenator.

For example, a system for performing transseptal extracorporeal membrane oxygenation (ECMO) on a patient may include: a first inner catheter that is distally tapered; an arterial sheath catheter, wherein the arterial sheath catheter is configured to coaxially surround the first inner catheter so that a distal outer surface of the arterial sheath catheter is flush with an outer surface of the first inner catheter, further wherein the arterial sheath catheter comprises a plurality of arterial infusion holes at a distal end region of the first inner catheter and wherein the first inner catheter is configured to extend more than 15 mm distal to the arterial sheath catheter; a venous sheath catheter, wherein the venous sheath catheter is configured to coaxially surround the arterial sheath catheter so that a distal inner surface of the venous sheath catheter is flush with an outer surface of the arterial sheath catheter, further wherein the venous sheath catheter comprises a plurality of lateral venous inflow holes through a sidewall region; a first proximal connector configured to couple a lumen of the arterial sheath catheter that is in fluid communication with the plurality of arterial infusion holes to an oxygenator; and a second proximal connector configured to couple a lumen of the venous sheath catheter that is in fluid communication with the plurality of lateral venous inflow holes to a venous aspiration pump.

The first inner catheter may be configured to extend more than 20 mm distal to the arterial sheath catheter (e.g., more than 25 mm, more than 30 mm, more than 35 mm, more than 40 mm, more than 35 mm, more than 50 mm, etc. distal to the arterial sheath catheter).

A system for performing transseptal extracorporeal membrane oxygenation (ECMO) on a patient may include: an arterial sheath set including: an arterial sheath catheter, wherein the arterial sheath catheter comprises a plurality of arterial infusion holes at a distal end region of the arterial sheath catheter, a first inner catheter configured to be axially positioned within a lumen of the arterial sheath and comprising a steerable distal end region configured to extend distally out of the arterial sheath, and a second inner catheter configured to be axially positioned within a lumen of the first inner catheter and comprising a distal expander, wherein the distal expander is configured to extend distally out of the first inner catheter; and a venous sheath catheter comprising a plurality of lateral venous inflow holes through a sidewall region of the venous sheath catheter, wherein the arterial sheath catheter is configured to extend distally from out of a lumen of the venous sheath catheter, further wherein the plurality of lateral venous inflow holes are configured to extend across a left atrium when the arterial sheath is positioned at least 1 cm distal to an aortic valve.

The venous sheath may be configured to slide over the arterial sheath catheter. In some examples the venous sheath catheter is configured to coaxially surround the arterial sheath catheter so that a distal inner surface of the venous sheath catheter is flush with an outer surface of the arterial sheath catheter. Any of these apparatuses (e.g., systems) may include a first proximal connector configured to couple a lumen of the arterial sheath catheter that is in fluid communication with the plurality of arterial infusion holes to an oxygenator. Any of these apparatuses may be comprising a second proximal connector configured to couple a lumen of the venous sheath catheter that is in fluid communication with the plurality of lateral venous inflow holes to a venous aspiration pump.

The distal expander may comprise a balloon. In some cases the first inner catheter is configured to extend distally out of the arterial sheath when an inner engagement region at a distal end of the arterial sheath engages with a complimentary region on the outer surface of the first inner catheter proximal to the steerable distal end region. The second inner catheter may be configured to extend distally out of the first inner catheter when an inner engagement region at a distal end of the first inner catheter engages with a complimentary region on the outer surface of the second inner catheter proximal to the distal expander.

For example, a system for performing transseptal extracorporeal membrane oxygenation (ECMO) on a patient may include: an arterial sheath set including: an arterial sheath catheter, wherein the arterial sheath catheter comprises a plurality of arterial infusion holes at a distal end region of the arterial sheath catheter, a first inner catheter configured to be axially positioned within a lumen of the arterial sheath and comprising a steerable distal end region configured to extend distally out of the arterial sheath when an inner engagement region at a distal end of the arterial sheath engages with a complimentary region on the outer surface of the first inner catheter proximal to the steerable distal end region, and a second inner catheter configured to be axially positioned within a lumen of the first inner catheter and comprising a distal expander, wherein the distal expander is configured to extend distally out of the first inner catheter when an inner engagement region at a distal end of the first inner catheter engages with a complimentary region on the outer surface of the second inner catheter proximal to the distal expander; and a venous sheath catheter comprising a plurality of lateral venous inflow holes through a sidewall region of the venous sheath catheter, wherein the arterial sheath catheter is configured to extend distally from out of a lumen of the venous sheath catheter, further wherein the plurality of lateral venous inflow holes are configured to extend across a left atrium when the arterial sheath is positioned at least 1 cm distal to an aortic valve.

For example, a system for performing transseptal extracorporeal membrane oxygenation (ECMO) on a patient may include: an arterial sheath set including: an arterial sheath catheter, wherein the arterial sheath catheter comprises a plurality of arterial infusion holes at a distal end region of the arterial sheath catheter, an inner catheter configured to be axially positioned within a lumen of the arterial sheath and comprising a steerable distal end region and an expander distal to the steerable distal end region, wherein the steerable distal end region and the expandable regions are configured to extend distally out of the arterial sheath when an inner engagement region at a distal end of the arterial sheath engages with a complimentary region on the outer surface of the first inner catheter proximal to the steerable distal end region; and a venous sheath catheter comprising a plurality of lateral venous inflow holes through a sidewall region of the venous sheath catheter, wherein the arterial sheath catheter is configured to extend distally from out of a lumen of the venous sheath catheter, further wherein the plurality of lateral venous inflow holes are configured to extend across a left atrium when the arterial sheath is positioned at least 1 a venous sheath catheter comprising a plurality of lateral venous inflow holes through a sidewall region of the venous sheath catheter, wherein the arterial sheath catheter is configured to extend distally from out of a lumen of the venous sheath catheter, further wherein the plurality of lateral venous inflow holes are configured to extend across a left atrium when the arterial sheath is positioned at least 1 cm distal to the aortic valve cm distal to the aortic valve.

The venous sheath may be configured to slide over the arterial sheath catheter. In some examples the venous sheath catheter is configured to coaxially surround the arterial sheath catheter so that a distal inner surface of the venous sheath catheter is flush with an outer surface of the arterial sheath catheter. Any of these apparatuses may include a first proximal connector configured to couple a lumen of the arterial sheath catheter that is in fluid communication with the plurality of arterial infusion holes to an oxygenator. Any of these apparatuses may include a second proximal connector configured to couple a lumen of the venous sheath catheter that is in fluid communication with the plurality of lateral venous inflow holes to a venous aspiration pump. The distal expander may be a balloon.

Also described herein are ECMO and LAVA-ECMO methods using any of these apparatuses. For example, a method for performing transseptal extracorporeal membrane oxygenation (ECMO) on a patient may include: introducing an arterial sheath catheter through a right atrium and into a patient's heart via an arterial access site; advancing a daughter inner catheter through the arterial sheath catheter and into a left atrium; advancing a granddaughter inner catheter out of a lumen of the daughter inner catheter and into the left ventricle with a balloon at a distal end of the granddaughter inner catheter at least partially expanded; deflecting a distal end region of the granddaughter inner catheter towards an aortic valve; advancing the granddaughter inner catheter distally across the aortic valve and into an ascending aortic arch; advancing the daughter inner catheter distally into the ascending aortic arch; advancing the arterial sheath catheter over the daughter inner catheter until the arterial sheath catheter is at least 1 cm distal to the aortic valve; and receiving, from the patient, oxygen-poor blood through a venous sheath catheter and returning oxygenated blood through the arterial sheath catheter to the ascending aortic arch.

In any of these methods deflecting the granddaughter inner catheter may comprise advancing the daughter inner catheter over the granddaughter inner catheter and deflecting the daughter inner catheter to deflect the granddaughter inner catheter. Advancing the daughter inner catheter may comprise advancing the daughter inner catheter distally over the granddaughter inner catheter into the ascending aortic arch. In some cases advancing the arterial sheath catheter over the daughter inner catheter comprises advancing the arterial sheath catheter over the daughter inner catheter and granddaughter inner catheter.

Any of these methods may include withdrawing the daughter inner catheter and granddaughter inner catheter through the arterial sheath catheter before returning oxygenated blood through the arterial sheath catheter. In any of these methods deflecting the distal end region of the granddaughter inner catheter comprises actuating a deflection mechanism comprising a pullwire extending through the daughter inner catheter to deflect the distal end region of the daughter inner catheter. Any of these methods may include delivering a guidewire through the granddaughter inner catheter into the left ventricle before advancing the granddaughter inner catheter. For example, any of these methods may include delivering a guidewire through the granddaughter inner catheter and into the ascending aorta before advancing the granddaughter inner catheter into the ascending aorta. In general, any of these methods may include advancing a venous sheath catheter over the mother catheter. In some cases advancing the venous sheath catheter comprises sealing the venous sheath catheter to an outer surface of the arterial sheath catheter. Any of these methods may include positioning the venous sheath catheter in an inferior vena cava.

In some cases the granddaughter inner catheter includes a low durometer deflection jacket that allows asymmetric compression of the inner shaft under pull wire tension. Any of these methods may include positioning the venous sheath catheter so that a plurality of inflow openings on the venous sheath catheter are positioned within the right atrium, the left atrium, or both the right atrium and left atrium. The daughter inner catheter may include a laser-cut hypotube with a spine to control planar deflection. Any o of these methods may include visualizing a radiopaque distal tip and a mid-shaft marker band on the granddaughter inner catheter. In some examples the method may include coupling the arterial sheath catheter and the venous sheath catheter to an ECMO pump device and performing ECMO.

For example, a method for performing transseptal extracorporeal membrane oxygenation (ECMO) on a patient may include: introducing an arterial sheath catheter through a right atrium and into a patient's heart via an arterial access site; advancing a daughter inner catheter through the arterial sheath catheter and into a left atrium; advancing a granddaughter inner catheter out of a lumen of the daughter inner catheter and into the left ventricle with a balloon at a distal end of the granddaughter inner catheter expanded; advancing the daughter inner catheter over the granddaughter inner catheter; deflecting a distal end region of the granddaughter inner catheter towards an aortic valve; advancing the granddaughter inner catheter distally out of the daughter inner catheter across the aortic valve and into the ascending aorta; advancing the daughter inner catheter distally over the granddaughter inner catheter into the ascending aorta; and advancing the arterial sheath catheter over the daughter inner catheter and granddaughter inner catheter until the arterial sheath catheter is at least 1 cm distal to the aortic valve; and receiving, from the patient, oxygen-poor blood through a venous sheath catheter and returning oxygenated blood through the arterial sheath catheter to the ascending aortic arch.

A method for performing transseptal extracorporeal membrane oxygenation (ECMO) on a patient may include: introducing an arterial sheath catheter through a right atrium and into a patient's heart via an arterial access site; advancing a daughter inner catheter through the arterial sheath catheter and into a left atrium; advancing a granddaughter inner catheter out of a lumen of the daughter inner catheter and into the left ventricle with a balloon at a distal end of the granddaughter inner catheter at least partially expanded; deflecting a distal end region of the granddaughter inner catheter towards an aortic valve; advancing the granddaughter inner catheter distally across the aortic valve and into an ascending aortic arch; advancing the daughter inner catheter distally into the ascending aortic arch; advancing the arterial sheath catheter over the daughter inner catheter until the arterial sheath catheter is at least 1 cm distal to the aortic valve; positioning a venous sheath catheter so that a plurality of inflow openings on the venous sheath catheter are positioned within the right atrium, the left atrium, or both the right atrium and left atrium; and receiving, from the patient, oxygen-poor blood through the venous sheath catheter and returning oxygenated blood through the arterial sheath catheter to the ascending aortic arch.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 9 shows a cross-sectional view of an example arterial hub.

FIG. 12A shows a region of a catheter-based ECMO system of FIG. 1.

FIG. 12B shows a cross-sectional view of the region of FIG. 12A.

FIG. 12C shows a cross-sectional detailed view of a tip shown in FIG. 12B.

FIG. 18 is a flowchart showing an example method for performing ECMO with the catheter-based ECMO system of FIG. 1.

FIG. 19 is a flowchart showing an example method for performing ECMO with a two catheter-based ECMO system.

FIGS. 22A-22G illustrate an example of a method of using an apparatus as described herein to perform ECMO in which a separate venous input catheter is used with an arterial output catheter (e.g., inner catheter).

FIGS. 23A-23G illustrate an example of a method of using an apparatus as described herein to perform ECMO in which a nested venous input catheter (e.g., outer catheter) is used with an arterial output catheter (e.g., inner catheter).

FIG. 25 shows the expander un-expanded, and FIG. 26 shows the expander expanded.

FIG. 27A shows the proximal ends of the arterial sheath, first inner catheter and second inner catheter nested within each other. FIG. 27B shows a section through the proximal end of the arterial sheath.

FIG. 29A shows a perspective view with the distal expander (e.g., balloon) expanded). FIG. 29B shows an enlarged sectional view through the second inner catheter of FIG. 29A.

FIG. 31A shows an enlarged section through the distal end region, including the steerable region. FIG. 31B shows an enlarged sectional view of the tip region. FIG. 31C shows a perspective view of a portion of the distal end region including the attachment for a pull wire/tendon. FIGS. 31D and 31E illustrate examples of deflection spines that may be used with the first inner catheters described herein. FIG. 31F is an enlarged section view of the proximal end region of the deflection region. FIG. 31G shows an enlarged view of a portion of the proximal end of the deflection region, showing the transition from the steerable region to the elongate shaft of the catheter.

FIG. 34A shows a perspective view of the proximal hub of an arterial sheath coupled to a cannula hub. FIG. 34B shows a section through the device of FIG. 34A. FIG. 34C illustrates operation of the device of FIGS. 34A-34B.

In FIG. 35, the venous sheath may be positioned separately than the arterial sheath set or may be applied over the arterial sheath set.

In FIG. 36A the venous sheath is shown in a perspective view. FIG. 36B shows a section through the venous sheath of FIG. 36A. FIG. 36B shows the distal tip of the venous sheath.

FIGS. 37A-37B illustrate examples of venous sheath inner catheters that may be used as part of any of these venous sheath sets as described herein. FIG. 37A shows a side perspective view of the venous sheath inner catheter. FIG. 37B shows a section view through the venous sheath inner catheter shown in FIG. 37A.

FIG. 38A shows a side perspective view with the distal expander expanded. FIG. 38B shows a section through the second inner catheter of FIG. 38A.

FIG. 39A shows an enlarged section through the distal end region, including the steerable region and expander. FIG. 39B shows an enlarged sectional view of the tip region. FIG. 39C shows a perspective view of a portion of the distal end region including the attachment for a pull wire/tendon. FIGS. 39D and 39E illustrate examples of deflection spines that may be used with the first inner catheters described herein. FIG. 39F is an enlarged section view of the proximal end region of the deflection region. FIG. 39G shows an enlarged view of a portion of the proximal end of the deflection region, showing the transition from the steerable region to the elongate shaft of the catheter.

FIG. 40A is a perspective view of the septal dilator daughter catheter. FIG. 40B shows section through the septal dilator daughter catheter of FIG. 40A. FIG. 40C shows an enlarged view of the distal end region of the septal dilator daughter catheter of FIG. 40A.

FIGS. 41A-41C show an example of another variation of a septal dilator daughter catheter, configured as a tapered dilator daughter catheter that may be part of any of the arterial sheath sets described herein, e.g., for use with an arterial sheath catheter. FIG. 41A is a perspective view of the tapered dilator daughter catheter. FIG. 41B is a section view through the tapered dilator daughter catheter of FIG. 41A. FIG. 41C is an enlarged view of the distal end region of the tapered dilator daughter catheter of FIGS. 41A-41B.

FIG. 42A is a perspective view of one example of a venous sheath configured as a "grandmother" catheter for use with an arterial sheath set. FIG. 42B shows a side perspective view of the venous sheath of the venous sheath system shown in FIG. 42A. FIG. 42C is a section through the venous sheath of FIG. 42B. FIG. 42D is an enlarged view of the distal end region of the venous sheath of FIG. 42B.

FIG. 43A shows a section through a distal end of the venous sheath of FIG. 42A. FIG. 43B shows an example of a pullwire/tendon control system for a venous sheath such as the one shown in FIG. 42B.

FIG. 44A shows partial perspective view (e.g., with the outer regions removed) of a venous sheath, including the deflection region and a region of shaft proximal to the deflection region. FIG. 44B shows one example of a distal end region of a venous sheath with the outer layers removed. FIG. 44C shows another example of a distal end region of a venous sheath with the outer layers (e.g., jackets) removed.

FIG. 45A is a side perspective view with a portion of the outer jacket removed. FIG. 45B shows a detail of a distal end (steerable) region including side openings with the outer layers (outer jacket) removed.

DETAILED DESCRIPTION

The present disclosure is related to systems, methods, and apparatuses that solve technical problems related to providing extracorporcal membrane oxygenation (ECMO) therapy through catheter-based systems. Two different examples of systems are described herein; combinations of these two systems may be made, thus any of the features of these systems may be incorporated together. A first example system and method uses three distinct catheters. That is, the first system can include a first catheter (sometimes referred to as a sheath or outer catheter), surrounding a second catheter (sometimes referred to as an inner catheter), and optionally including a third catheter that may be nested within the first and second catheters. These catheters may be used with one or more guidewires. The catheters may be configured so that the outer and/or inner catheters may include lateral openings for blood input (e.g., venous input) and blood output (e.g., arterial output), respectively. In some examples, the catheters can slide independently within each other. A pull wire attached to a handle can enable the surgeon to deflect a distal tip of the system to guide the insertion and placement of the system. The system can provide the removal of blood from a first location and the return of blood to a second location. In some examples the system can include two separate (non-coupled) catheters. A first catheter may be used to remove blood while a second catheter can be used to return blood.

In general for any of the systems described herein, a catheter may be advanced across the atrial septum, through the mitral valve, and into the aorta. Optionally this catheter may be positioned with the arterial outputs near the aortic root, in the ascending aorta, in the aortic arch or in the descending aorta. This catheter, which may be the inner catheter, may be used to deliver oxygenated blood to the patient. An outer catheter, which may be coaxial to other catheter(s), and/or may be configured to be separately positionable relative the other catheter(s), can remove oxygen-poor blood from the patient. In some examples, this catheter may be positioned in the inferior vena cava.

Figure 1:
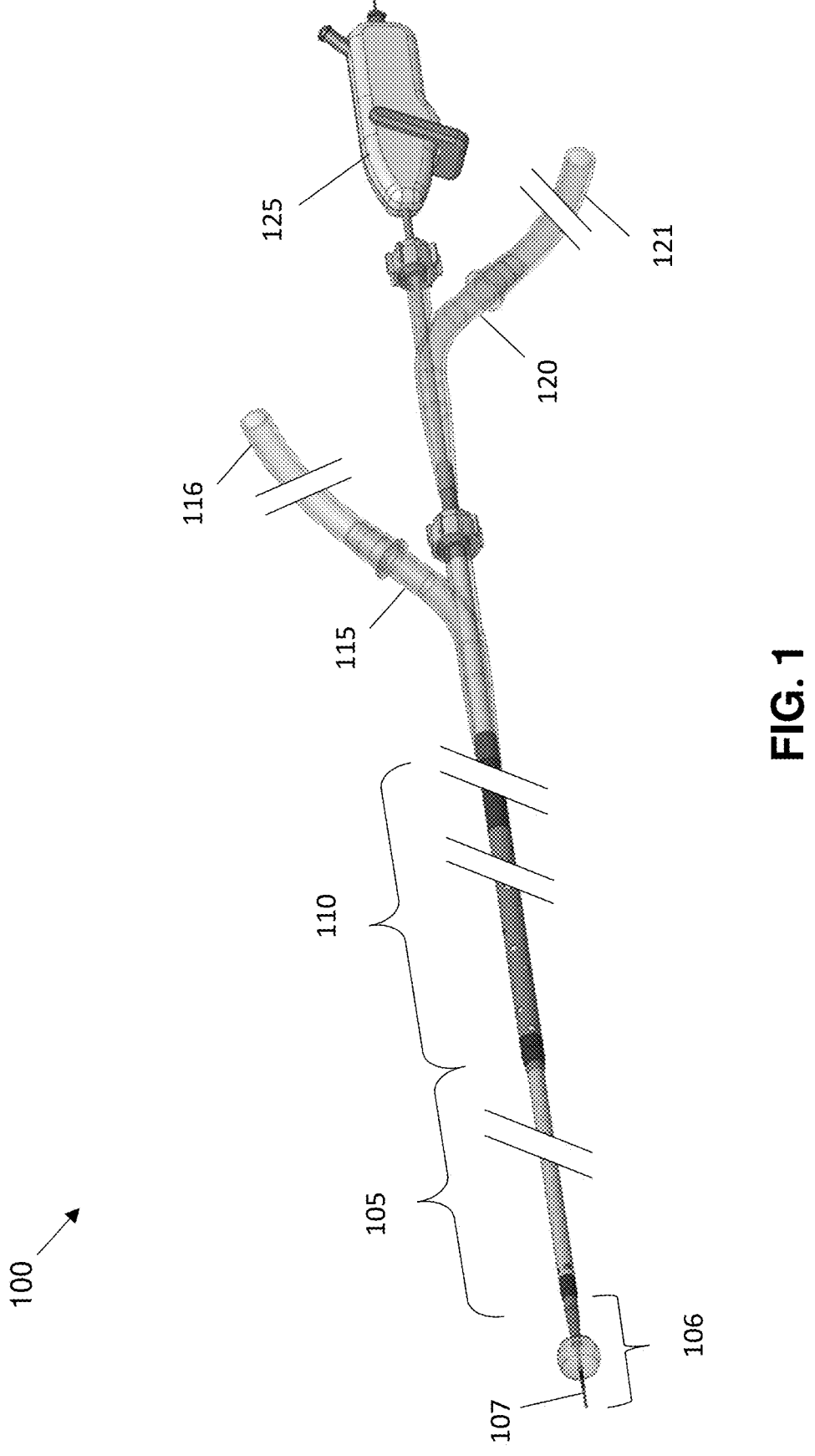
FIG. 1 is an example catheter-based ECMO system.

FIG. 1 is an example catheter-based ECMO system 100. Although described herein, the catheter-based ECMO system 100 may be implemented as an apparatus and be incorporated or included within any other feasible system. In general, the catheter-based ECMO system can include two or three catheters which are coaxial, concentric and surround each other. For example, the catheter-based ECMO system 100 may include an arterial sheath 105, an (optional) arterial sheath inner catheter 106, a guidewire 107, a venous sheath 110, a venous hub 115, an arterial hub 120, and a handle 125. The arterial sheath inner catheter 106 can be a first inner catheter, the arterial sheath 105 can be a second inner catheter, and the venous sheath 110 can be an outer catheter. Notably, as used herein, the terms sheath and catheter may be used interchangeably. Thus, the venous sheath 110 may also be described as a catheter, a sheath, or venous catheter. In other examples, the catheter-based ECMO system 100 may include fewer, more, or different elements. In FIG. 1 the arterial sheath inner catheter 106 is shown with a distal balloon 201 (see FIGS. 2A-2B), however in some examples the arterial sheath 105 may include a distal balloon. Alternatively, the arterial sheath 105 may be optional and the arterial sheath inner catheter 106 may be included and may interface directly with the venous sheath 110 (e.g., the outer catheter). The arterial sheath inner catheter 106 may include one or more openings for passing oxygenated blood (e.g., infusion holes).

The catheter-based ECMO system 100 can be used to receive oxygen-poor blood (deoxygenated blood) or blood from the left atrium from a patient, oxygenate the blood outside the patient's body, and return the oxygenated blood to the patient. In general, the catheter-based ECMO system 100 can include two more (e.g., three) coaxial catheters that are configured to be guided into various veins and arteries of a patient and then provide a means for removing the oxygen-poor blood from the patient, passing the blood through an external oxygenator, and then returning the now oxygenated to the patient. As described herein, the catheter-based ECMO system 100 is advanced through a vein and a distal tip of one of the catheters is further advanced through a transseptal puncture. Blood is removed via another one of the catheters proximal to the distal tip. Oxygenated blood is returned to the patient through the distal tip (and optionally one or more infusion holes) into the aorta. Operation of the catheter-based ECMO system 100 is described in more detail in conjunction with FIGS. 15A-15I, FIG. 18, and FIGS. 23A-23G.

As noted above, the catheter-based ECMO system 100 can include two or three coaxial catheters: the arterial sheath inner catheter 106, the arterial sheath 105, and/or the venous sheath 110. The (in some cases, optional) arterial sheath inner catheter 106 may be the innermost catheter (a first inner catheter), surrounded by the arterial sheath 105 (a second inner catheter), further surrounded by the venous sheath 110 (an outer catheter). Blood is removed from the patient via the venous sheath 110 and returned to the patient via the arterial sheath 105. The venous hub 115 is coupled to the venous sheath 110 and allows blood to be transported from the catheter-based ECMO system 100 through tubing 116. Blood from the venous hub 115 is directed to an external oxygenator (not shown).

The arterial hub 120 is coupled to the arterial sheath 105 through one or more lumens. Tubing 121 may be coupled to the arterial hub 120 and the external oxygenator. Oxygenated blood is returned to the patient via the arterial hub 120 and the arterial sheath 105.

The handle 125 may be used to advance and retract the catheter-based ECMO system 100 to and from the patient. In some examples, the handle 125 may be used to deflect a distal end of the arterial sheath inner catheter 106.

One or more guidewires may be included as part of the system. In some examples, the guidewire 107 may be approximately 0.035 inches in diameter. In some other examples, the guidewire 107 may be any greater diameter, such as diameters greater than 0.035 inches (including, but not limited to 0.040, 0.045, 0.050, or any other feasible greater diameter). In some other examples, the guidewire 107 may be any other lesser diameter, including diameters less than 0.035 inches (including, but not limited to 0.030, 0.025, 0.020, or any other feasible smaller diameter). The guidewire 107 may be formed from any feasible material, including Nitinol.

Figures 2A, 2B:
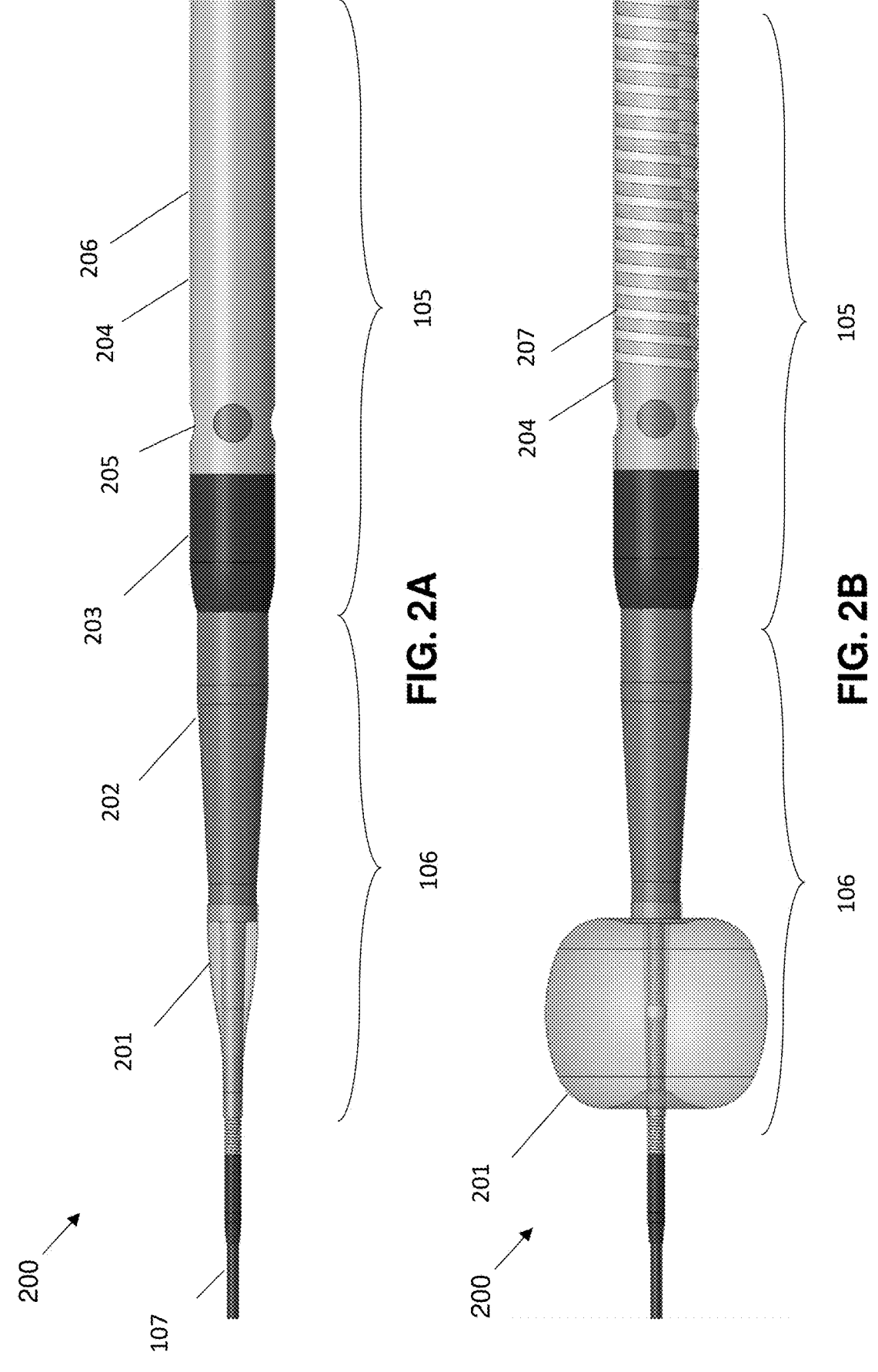
FIG. 2A shows a distal end of a catheter-based ECMO system.
FIG. 2B shows another view of the distal end of the catheter-based ECMO system.

FIG. 2A shows a distal end of a catheter-based ECMO system 200. In some examples, the catheter-based ECMO system 200 may be an example of the catheter-based ECMO system 100 of FIG. 1. Thus, the catheter-based ECMO system 200 can include the guidewire 107, the arterial sheath inner catheter 106, and the arterial sheath 105. The arterial sheath inner catheter 106 may be flexible and can taper from the arterial sheath 105 to the distal tip of the arterial sheath inner catheter 106. The arterial sheath inner catheter 106 may include a balloon 201 and a tapered element 202.

The balloon 201, shown deflated here, may be used during positioning of the catheter-based ECMO system 200. Operation of the balloon 201 is described in more detail below in conjunction with FIGS. 2A, 2B, FIGS. 15A-15I, and FIGS. 17A-17I. The tapered element 202 enables smooth insertion into the patient. The tapered element 202 may be formed from any durable, and generally pliable material. Generally, the tapered element 202 may taper from a larger diameter proximally to a smaller diameter distally.

The arterial sheath 105 can include a tip 203 and an arterial body 204. The arterial body 204 can include one or more infusion holes 205 disposed on the arterial body 204. The arterial body 204 may be covered with a polymer body 206. In general, the arterial sheath 105 is used to return oxygenated blood to the patient. The oxygenated blood may be pumped through the arterial sheath 105 through the infusion holes 205. In some examples, the arterial sheath inner catheter 106 may be withdrawn from the arterial sheath 105 allowing oxygenated blood to be returned through an opening of the tip 203.

FIG. 2B shows another view of the distal end of the catheter-based ECMO system 200. In this view, the arterial sheath 105 is depicted with an inner hypotube 207. In general, the hypotube 207 may be disposed underneath the polymer body 206. The hypotube 207 may provide flexible rigidity for the arterial sheath 105. That is, the hypotube 207 can be more rigid toward the handle (not shown) and more flexible toward the tip 203.

The balloon 201 is shown inflated. The balloon 201 may help guide or center the arterial sheath inner catheter 106 during insertion into the patient, particularly within the patient's heart, and may assist in the safe crossing of the mitral valve.

Figure 3:
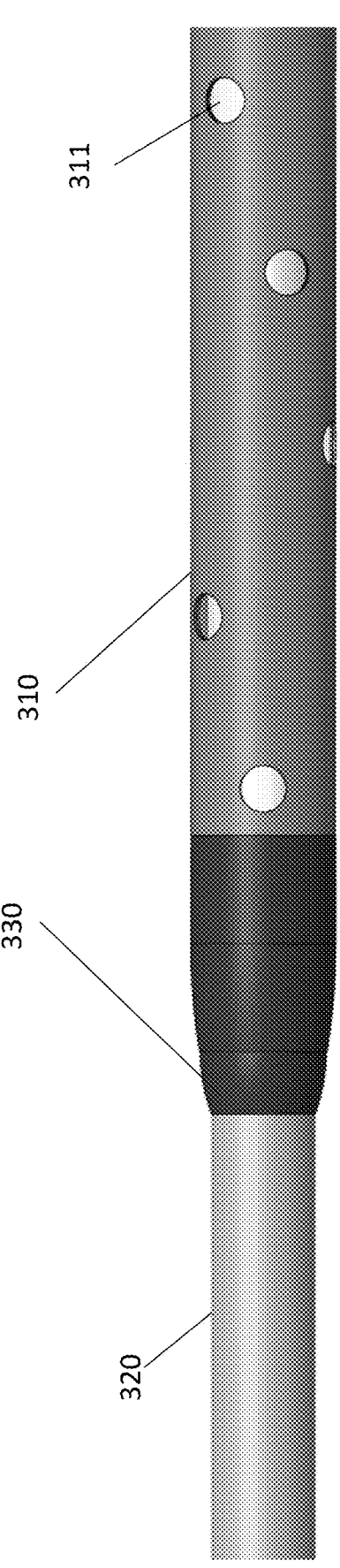
FIG. 3 shows another view of a catheter-based ECMO system.

FIG. 3 shows another view of a catheter-based ECMO system 300. In some examples, the catheter-based ECMO system 300 may be an example of the catheter-based ECMO system 100 of FIG. 1. In particular, FIG. 3 shows a transition between a venous sheath 310 (another example of the venous sheath 110) and an arterial sheath 320 (which can be another example of the arterial sheath 105).

In some examples the venous sheath 310 may have a size of approximately 30 Fr and arterial sheath 320 may have a size of approximately 22 Fr. In general, the size of the arterial sheath 320 may be smaller than the size of the venous sheath 310 to allow the arterial sheath 320 to be fully coaxial with respect to the venous sheath 310. The venous sheath 310 may include a plurality of inflow holes 311 disposed about the sides of the venous sheath 310.

The catheter-based ECMO system 300 may include a compliant and durable seal 330 between the venous sheath 310 and the arterial sheath 320. The seal 330 may be made of any feasible and generally lubricious material that can provide a liquid-tight (watertight) seal to the arterial sheath 320. In some examples, there may be a slight interference fit between an inner diameter of the seal 330 and an outer diameter of the arterial sheath 320.

Figure 4:
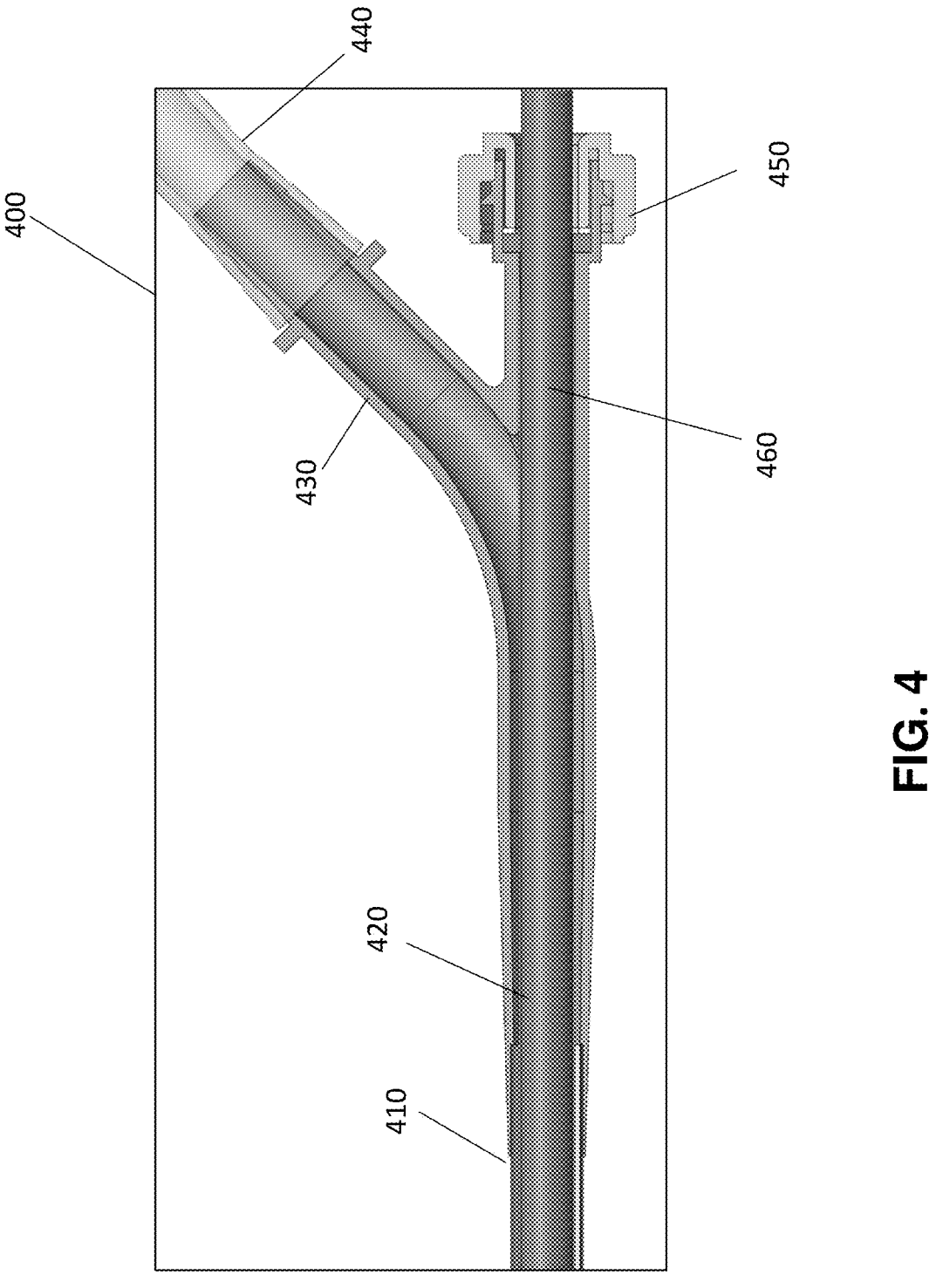
FIG. 4 shows an example of a venous hub.

FIG. 4 shows an example of a venous hub 400. The venous hub 400 may be an example of the venous hub 115 of FIG. 1. The venous hub 400 includes a venous sheath 410, a venous lumen 420, a venous port 430, an arterial shaft 460, and a hemostasis valve 450.

The venous sheath 410 can extend distally from the venous hub 400 and can be an example of the venous sheath 110. Notably, the venous lumen 420 can be coupled to the venous sheath 410 and allow oxygen-poor blood to flow from the patient through the venous port 430 further through optional tubing 440. Typically, the tubing 440 can direct the blood toward an oxygenator. In some examples, the tubing 440 is ⅜ inches in an inner or outer diameter. However, in other examples, the tubing 440 can be any feasible inner or outer diameter.

The hemostasis valve 450 may allow other lumens or shafts to pass through the venous hub 400. As shown, the hemostasis valve 450 may allow an arterial shaft 460 to pass therethrough.

Figure 5:
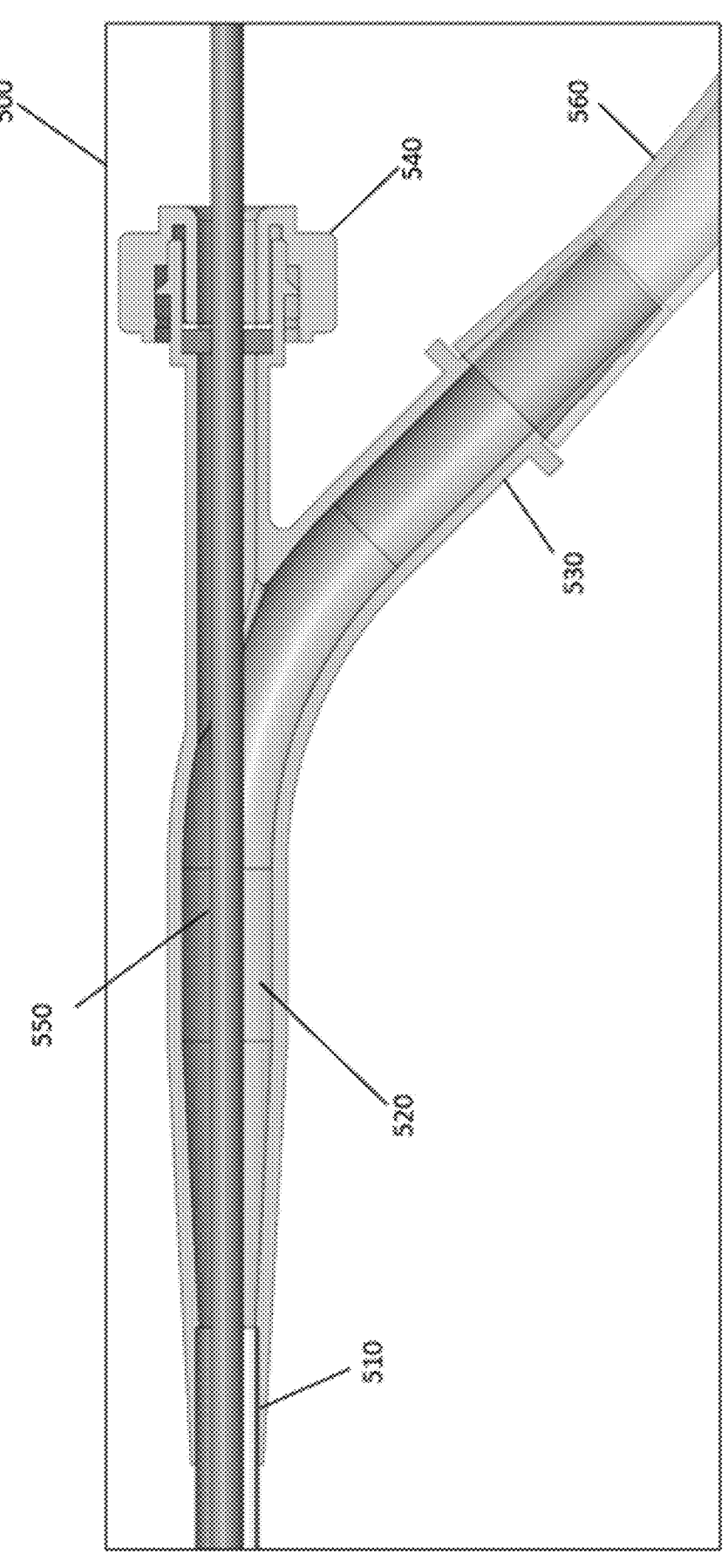
FIG. 5 shows an example arterial hub.

FIG. 5 shows an example arterial hub 500. The arterial hub 500 may be an example of the arterial hub 120 of FIG. 1. The arterial hub 500 may include an arterial sheath 510, an arterial lumen 520, an arterial port 530, and a hemostasis valve 540.

The arterial sheath 510 can extend distally from the arterial hub 500 toward a proximal end of the venous hub 400 of FIG. 4. The arterial lumen 520 can be coupled to the arterial sheath 510 can allow oxygenated blood to flow from an external oxygenator to the patient. The oxygenated blood may be received through optional tubing 560. The arterial hub 500 can include the hemostasis valve 540 that is liquid tight and allows an inner catheter shaft 550 to enter and pass through the arterial hub 500. Similar to the hemostasis valve 450, the hemostasis valve 540 can be liquid tight.

Figure 6:
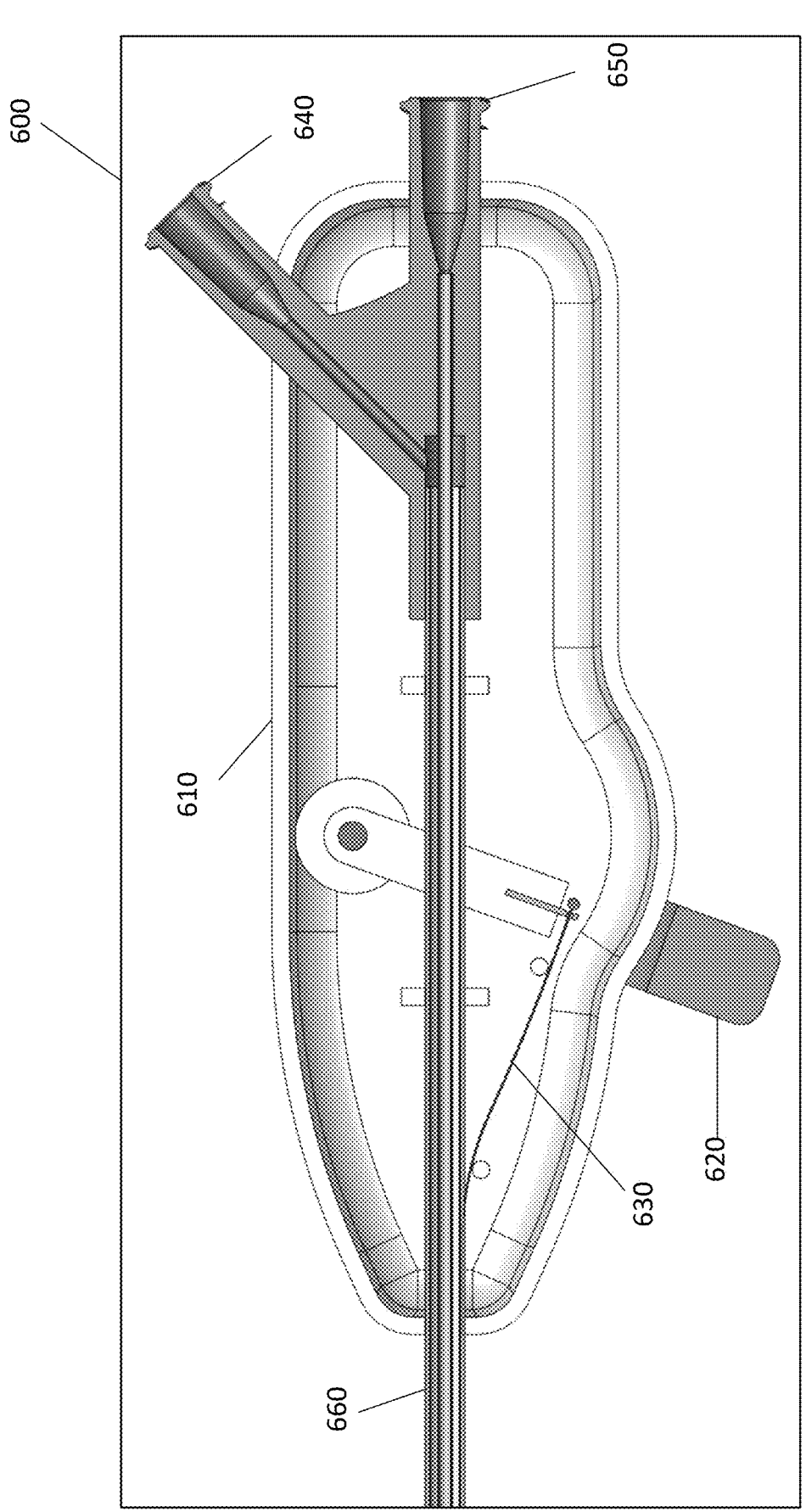
FIG. 6 shows a cutaway view of a handle.

FIG. 6 shows a cutaway view of a handle 600. The handle 600, can be another example of the handle 125 of FIG. 1. The handle 600 may include a body 610, a lever 620, a pull wire 630, a balloon inflation port 640, and a guidewire port 650. The handle 600 may be coupled to an arterial sheath inner catheter 660 which may be an example of the arterial sheath inner catheter 106.

The body 610 may function as a housing to contain any of the elements described herein. In particular, the body 610 may support, mount, and/or house the lever 620, the balloon inflation port 640, and the guidewire port 650. The lever 620 is coupled to the pull wire 630. Together, the lever 620 and the pull wire 630 and be used to deflect a distal end of the arterial sheath inner catheter 660. The balloon inflation port 640 (sometimes referred to as a luer port) may receive a gas or liquid (saline, CO2, or the like) to inflate a balloon distally located with respect to the handle 600. In a similar manner, the guidewire port 650 may receive a guidewire. The guidewire may be an example of the guidewire 107.

Figures 7A, 7B:
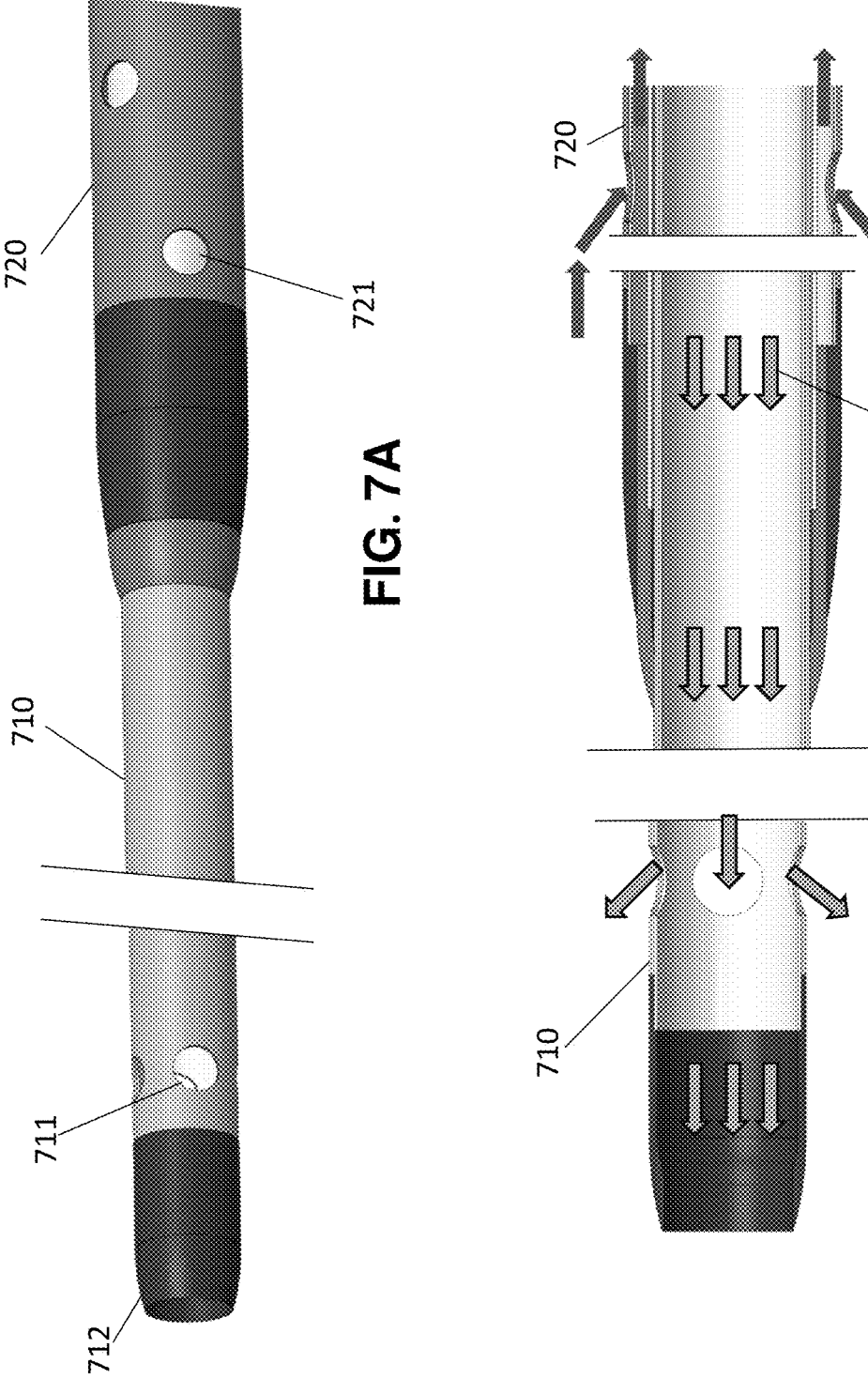
FIGS. 7A and 7B show a distal end of the catheter-based ECMO system of FIG. 1.

FIGS. 7A and 7B show a distal end of the catheter-based ECMO system 100 of FIG. 1. Both FIGS. 7A and 7B show the catheter-based ECMO system 100 with the arterial sheath inner catheter removed. FIG. 7A includes an arterial sheath 710 and a venous sheath 720. The arterial sheath 710 can be an example of the arterial sheath 105 and the venous sheath 720 can be an example of the venous sheath 110, both of FIG. 1.

The venous sheath 720 can include a plurality of inflow holes 721 that enable blood to be received to the venous sheath 720. The arterial sheath can include a plurality of infusion holes 711 as well as an infusion opening 712 located on a distal end of the arterial sheath 710. The infusion holes 711 and the infusion opening 712 allow blood to be returned to the patient.

FIG. 7B shows a detailed cross-sectional view of the distal end catheter-based ECMO system 100. For example, the arterial sheath 710 and the venous sheath 720 are shown in cross section. Oxygenated blood may flow out of the arterial sheath 710. Arrows 713 illustrate blood flow from the catheter-based ECMO system 100. Blood may be removed from the patient through the venous sheath 720. Arrows 722 illustrate blood flow from the patient and through the venous sheath 720.

Note that in any of the apparatuses described herein, the arterial sheath (e.g., including a plurality of infusion or "outflow" openings) and the venous sheath (e.g., including a plurality of inflow openings) may be reversed in the apparatus and method, depending on the direction of flow intended and the insertion technique used. For example, in some of the examples shown herein the arterial sheath is shown nested within (and extending distally of) the venous sheath so that outflow openings are distal to the inflow openings. Any of these methods and apparatuses may be configured so that the venous sheath is instead nested within (and extends distally of) the arterial sheath. Thus, the venous and arterial sheaths may be referred to as a "first" or outer sheath and a second or inner sheath that may be configured as descried herein; the venous or arterial nature of the particular sheaths may be determined by the posterior connections. The total opening area for the inflow openings may be equal to the total opening area for the outflow openings (e.g., the sum of the areas of the openings). Alternatively, in some examples, the total opening areas for the inflow openings may be smaller than the total opening area for the outflow openings. Alternatively, in some examples, the total opening areas for the outflow openings may be smaller than the total opening area for the inflow openings.

Figure 8:
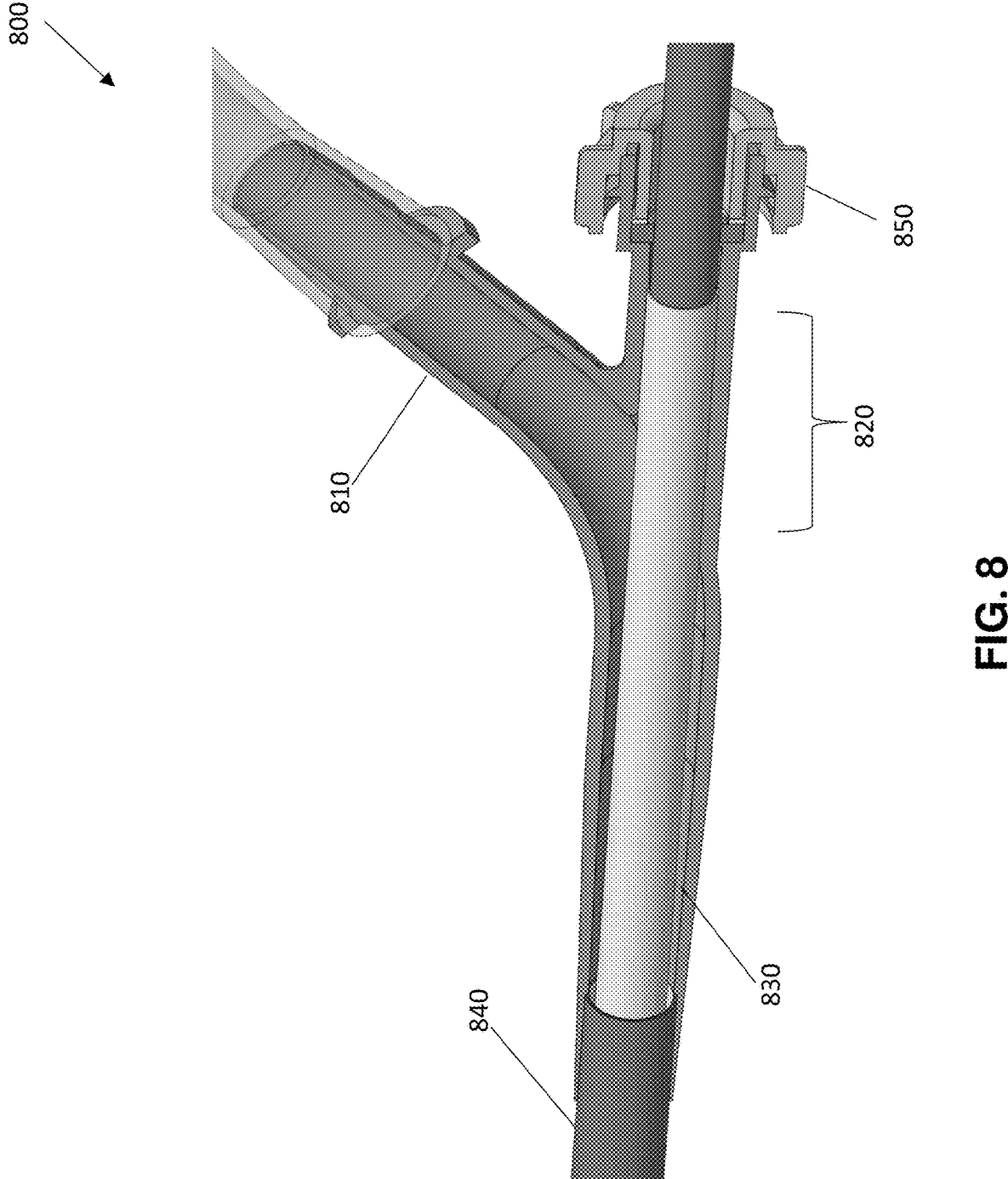
FIG. 8 shows a cross-sectional view of an example venous hub.

FIG. 8 shows a cross-sectional view of an example venous hub 800. The venous hub 800 may be an example of the venous hub 115 of FIG. 1. The venous hub 800 may include a venous port 810, a venous sheath inner liner 820, a venous sheath 840, and a venous sheath lumen 830. In some examples, the venous sheath lumen 830 may be separate or may be integral (combined) with the venous sheath 840.

Blood may be received from inflow holes (not shown) on the venous sheath 840, through the venous sheath inner liner 820, transported through the venous port 810 and directed to an oxygenator. An arterial sheath 850 may pass substantially through the venous hub 800 to an arterial hub (not shown).

FIG. 9 shows a cross-sectional view of an example arterial hub 900. The arterial hub 900 may be an example of the arterial hub 120 of FIG. 1. The arterial hub 900 may include an arterial port 910, an arterial sheath 920, and a hemostasis valve 930. Oxygenated blood may be received through the arterial port 910 and transported through the arterial sheath 920. In FIG. 9, the arterial sheath inner catheter is not shown (for example, may be removed) from the arterial hub 900. The hemostasis valve 930 is shown closed.

Figures 10A, 10B, 10C:
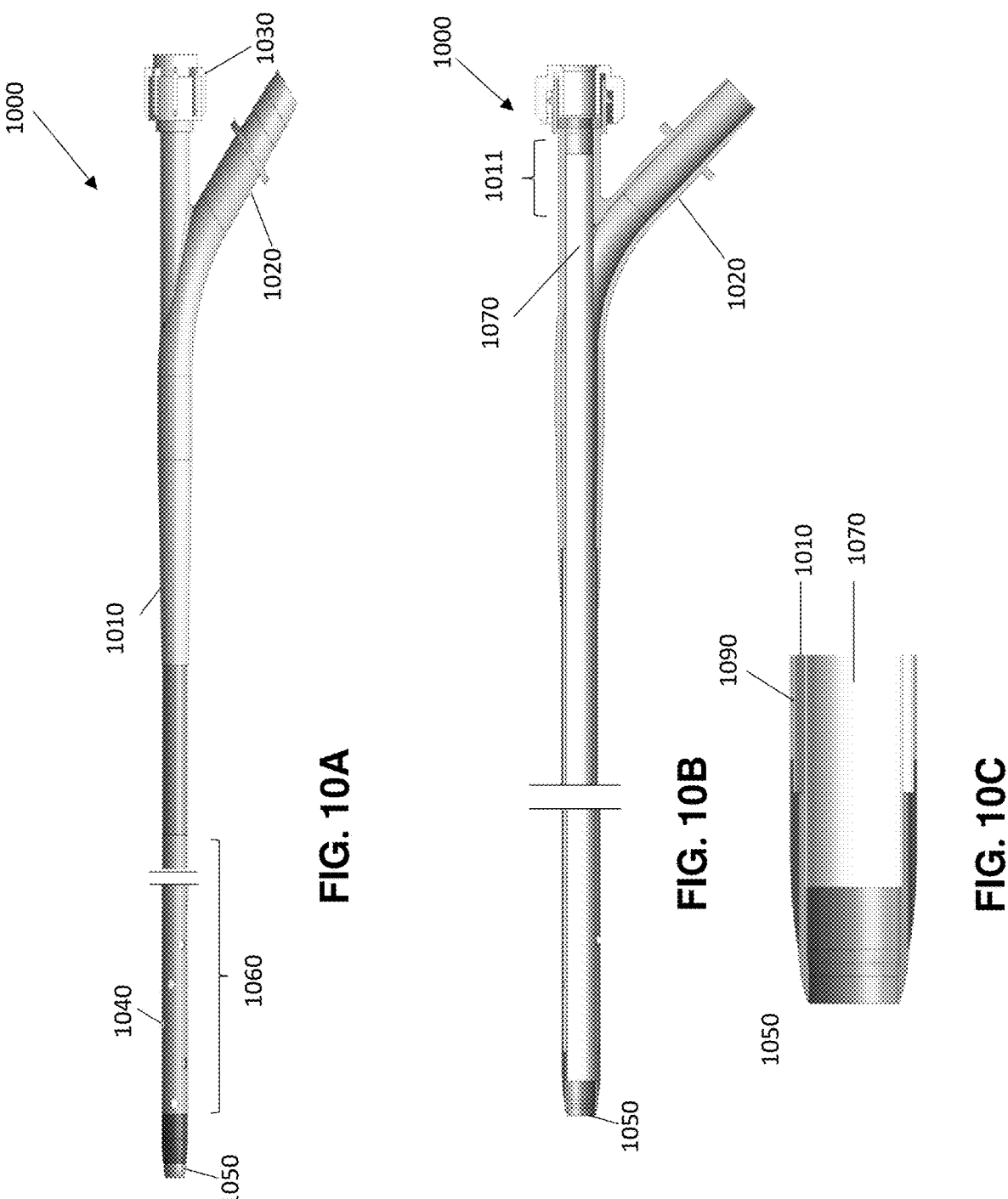
FIG. 10A shows a region of the catheter-based ECMO system 100 of FIG. 1.
FIG. 10B shows a cross-sectional view of the region shown in FIG. 10A.
FIG. 10C shows a cross-sectional detailed view of a tip of the region shown in FIG. 10A.

FIG. 10A shows a region 1000 of the catheter-based ECMO system 100 of FIG. 1. The region 1000 may include a venous sheath 1010, a venous hub 1020, a hemostasis valve 1030, and a tip 1050. The venous sheath 1010 may include a plurality of inflow holes 1040 to receive blood that may be directed through the venous hub 1020 to an oxygenator.

The tip 1050 may be positioned distally with respect to the venous hub 1020. In some examples, the tip 1050 may be formed from a radiopaque material (such as, but not limited to, a tungsten loaded pebax). A region 1060 of the venous sheath 1010 may have a variable stiffness (e.g., have a multi-durometer). For example, the stiffness or flexibility of the venous sheath 1010 may decrease as you move away from the hemostasis valve 1030 toward the tip 1050. The variable stiffness of region 1060 may assist in placement and positioning the catheter-based ECMO system within the patient. In some examples, an outer diameter of the venous sheath 1010 can be approximately 28 Fr.

FIG. 10B shows a cross-sectional view of the region 1000 of FIG. 10A. The cross-sectional view shows an inner liner 1070 that may be bonded to the venous sheath 1010. An example bonding region is shown as region 1011. The bond in region 1011 may seal blood from leaking at the venous hub 1020. The inner liner 1070 may provide lumen to receive a guidewire. In some examples, an inner diameter of the inner liner 1070 may be approximately 21 Fr.

FIG. 10C shows a detailed cross-sectional view of the tip 1050 of the region 1000. In some examples the tip 1050 may be a two-layer tip that may be bonded to an outer jacket 1090 of the venous sheath 1010 and the inner liner 1070. Furthermore, the inner diameter of the distal tip 1050 may be approximately 20 Fr. The outer jacket 1090 and the inner liner 1070 cooperatively form a lumen that can carry blood from the plurality of inflow holes 1040 to the venous hub 1020.

Figure 11A:
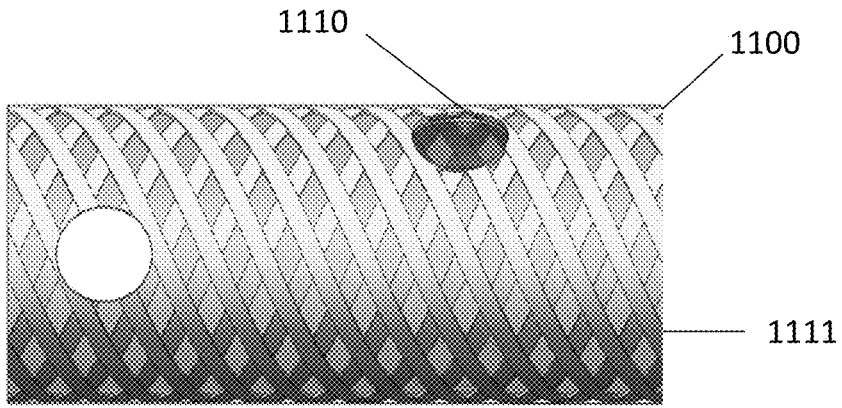
FIG. 11A shows an example braid-reinforced shaft.

FIG. 11A shows an example braid-reinforced shaft 1100. The braid-reinforced shaft 1100 may be included within the arterial sheath 105 or the venous sheath 110 of FIG. 1. As described herein, each of the arterial sheath 105 and the venous sheath 110 can include a plurality of holes 1110 disposed on the sides of the sheaths. In some examples, the holes 1110 may be laser ablated. The braid-reinforced shaft 1100 may include a polymer outer jacket 1111 bonded to a braided material. The braided material can be stainless steel, Nitinol, or any other feasible material.

Figure 11B:
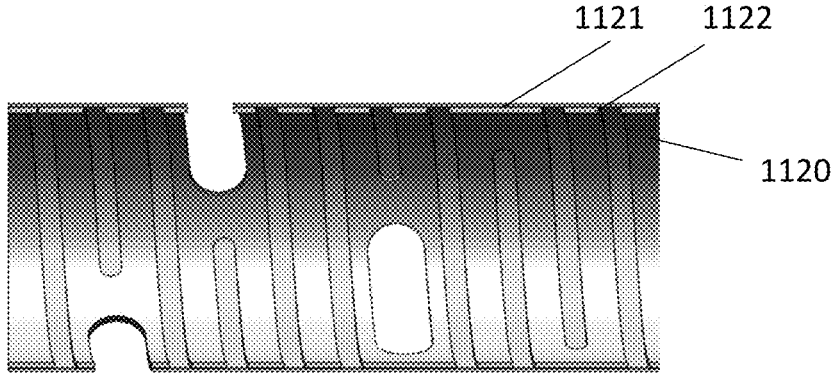
FIG. 11B shows a cross section of another reinforced shaft.
Figure 11C:
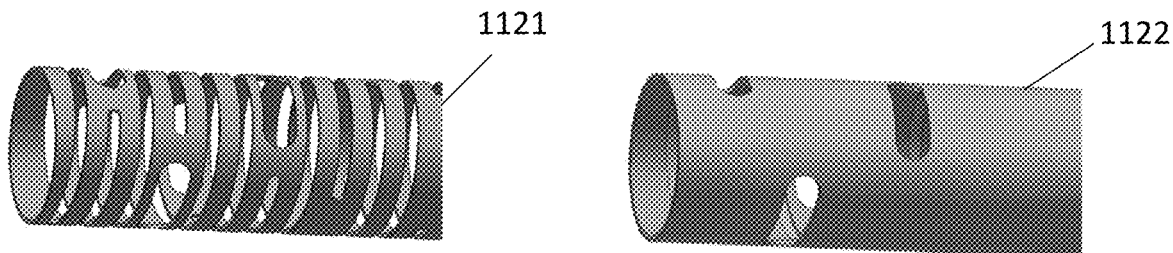
FIG. 11C shows separate views of the hypotube and the polymer jacket.

FIG. 11B shows a cross section of another reinforced shaft 1120. The reinforced shaft 1120 may include a laser cut hypotube 1121 and a polymer jacket 1122. In some examples, the polymer jacket 1122 may be bonded to the hypotube 1121. Furthermore, the reinforced shaft 1120 may be laser ablated such that holes may be formed in the polymer jacket 1122 and the hypotube 1121 simultaneously. FIG. 11C shows separate views of the hypotube 1121 and the polymer jacket 1122.

Figures 12A, 12B, 12C:
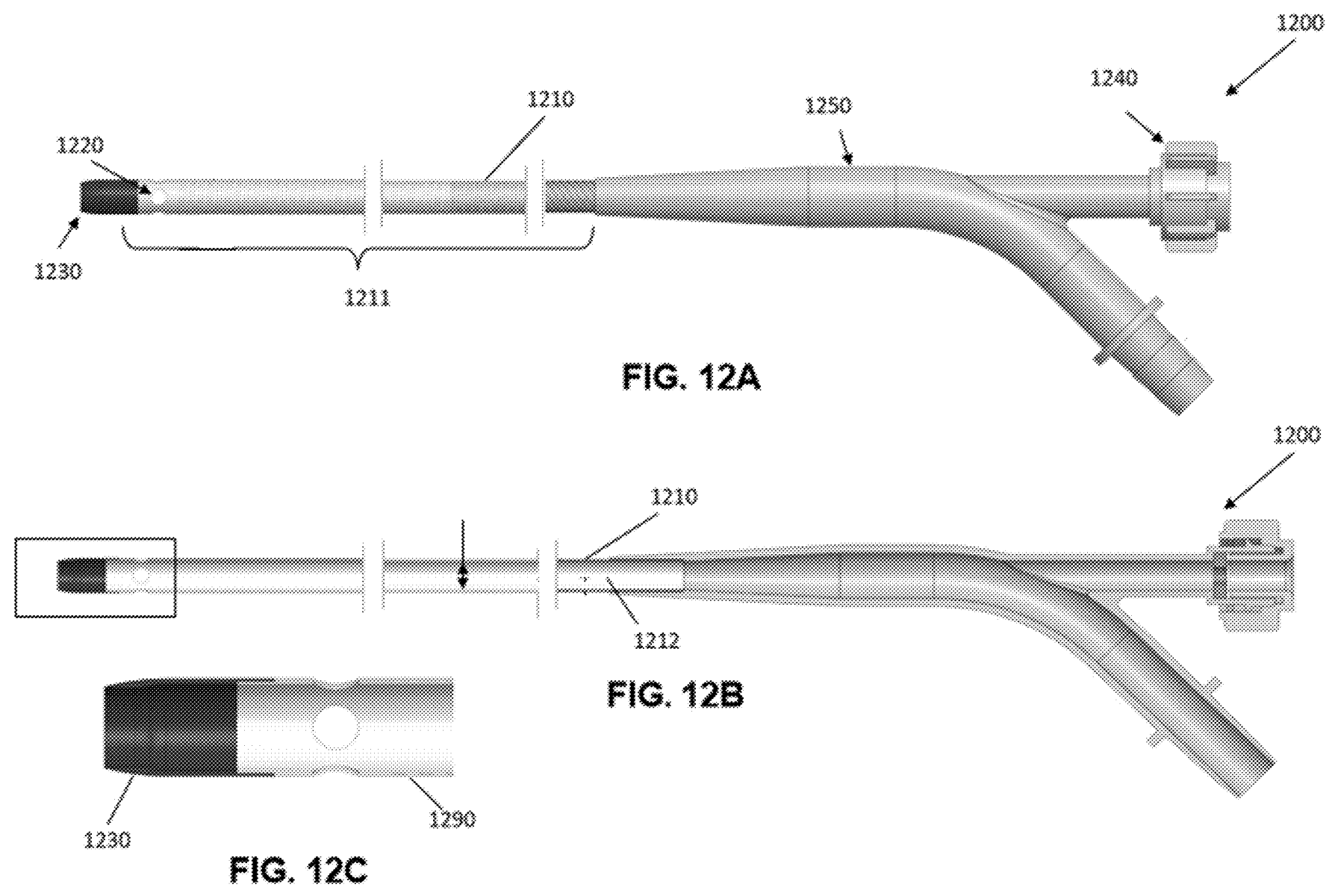

FIG. 12A shows a region 1200 of a catheter-based ECMO system 100 of FIG. 1. The region 1200 includes an arterial sheath 1210, a tip 1230, a hemostasis valve 1240, and an arterial hub 1250. The arterial sheath 1210 can include a region 1211 that has a variable stiffness. For example, the arterial sheath 1210 can be stiffer closer to the arterial hub 1250 and more flexible (less stiff) farther away from the arterial hub 1250. The varying stiffness may help position the catheter-based ECMO system 100 within the patient. In some examples, the region 1211 may include a braid-reinforced section closer to the arterial hub 1250 and a coil section further from the arterial hub 1250.

Infusion holes 1220 may be disposed on the side of the arterial sheath 1210. In some examples, the arterial sheath 1210 may include a tip 1230 which may be radiopaque. In some implementations, the tip 1230 may be formed from a tungsten loaded pebax, however, any other feasible material may be used. In some examples, an outer diameter of the arterial sheath 1210 can be approximately 20 Fr.

FIG. 12B shows a cross-sectional view of the region 1200 of the catheter-based ECMO system 100 of FIG. The arterial sheath 1210 may include an inner lumen 1212. In some examples, the inner lumen 1212 can have an inner diameter of approximately 18 Fr. In some examples, the inner lumen 1212 can be coated with a lubricious coating such as, but not limited to, a polytetrafluoroethylene (PTFE).

FIG. 12C shows a cross-sectional detailed view of the tip 1230 of the region 1200. In some examples the tip 1230 may be bonded to an outer jacket 1290 of the venous sheath 1010 and the inner liner. Furthermore, the inner diameter of the distal tip 1050 may be approximately 17 Fr.

Figures 13A, 13B:
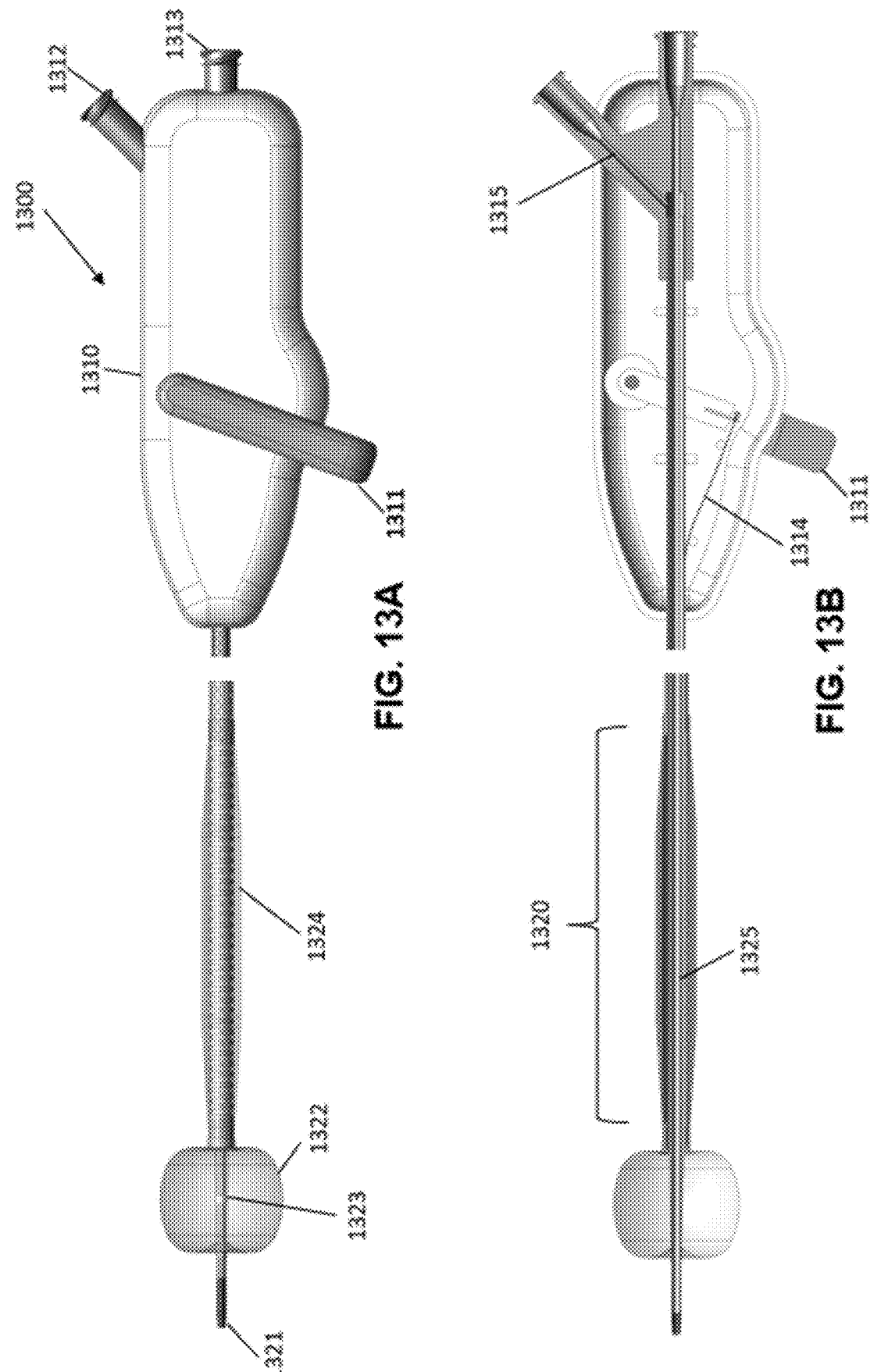
FIG. 13A shows a partial diagram of the catheter-based ECMO system of FIG. 1.
FIG. 13B shows a cross-sectional view of the catheter-based ECMO system of FIG. 1.

FIG. 13A shows a partial diagram 1300 of the catheter-based ECMO system 100 of FIG. 1. In particular, the diagram 1300 may show a portion of an arterial sheath inner catheter that includes a handle 1310 and a distal region 1320. The distal region 1320 may generally be a distal region of an arterial sheath, such as the arterial sheath 105 of FIG. 1. The diagram 1300 may include a tip 1321, a balloon 1322, a marker 1323, and a tapered element 1324.

The tip 1321 may be formed from any feasible material, such as a radiopaque material. In general, the tip 1321 is formed from a soft material. The balloon 1322 may be inflated to help center the arterial sheath inner catheter with respect to a mitral value. The use of catheter-based ECMO system 100 in general, and the balloon 1322 in particular is described in more detail below with respect to FIGS. 15A-15I and FIG. 18. A radiopaque marker 1323 may be surrounded by the balloon 1322. In some examples, the marker 1323 may be used to help locate at least the balloon 1322 as the catheter-based ECMO system 100 in the patient. The tapered element 1324 may surround a hypotube.

The handle 1310 may include a lever 1311, balloon inflation port 1312 and a guidewire port 1313. The balloon inflation port 1312 may be coupled with a lumen to the balloon 1322. The balloon 1322 may be inflated with the application of a liquid or gas through the balloon inflation port 1312. The guidewire port 1313 can receive a guidewire (such as the guidewire 107 of FIG. 1) to help guide and position the catheter-based ECMO system 100 within the patient. The lever 1311 may be used to move a pull wire (not shown) to deflect the tip 1321.

FIG. 13B shows a cross-sectional view of the catheter-based ECMO system 100 which can include a lumen 1325, a deflection pull wire 1314, a balloon inflation lumen 1315.

The lumen 1325 can be used by the guidewire. One end of the deflection pull wire 1314 is coupled to the lever 1311, while another end of the deflection pull wire 1314 may be coupled to the tip 1321.

Figures 14A, 14B:
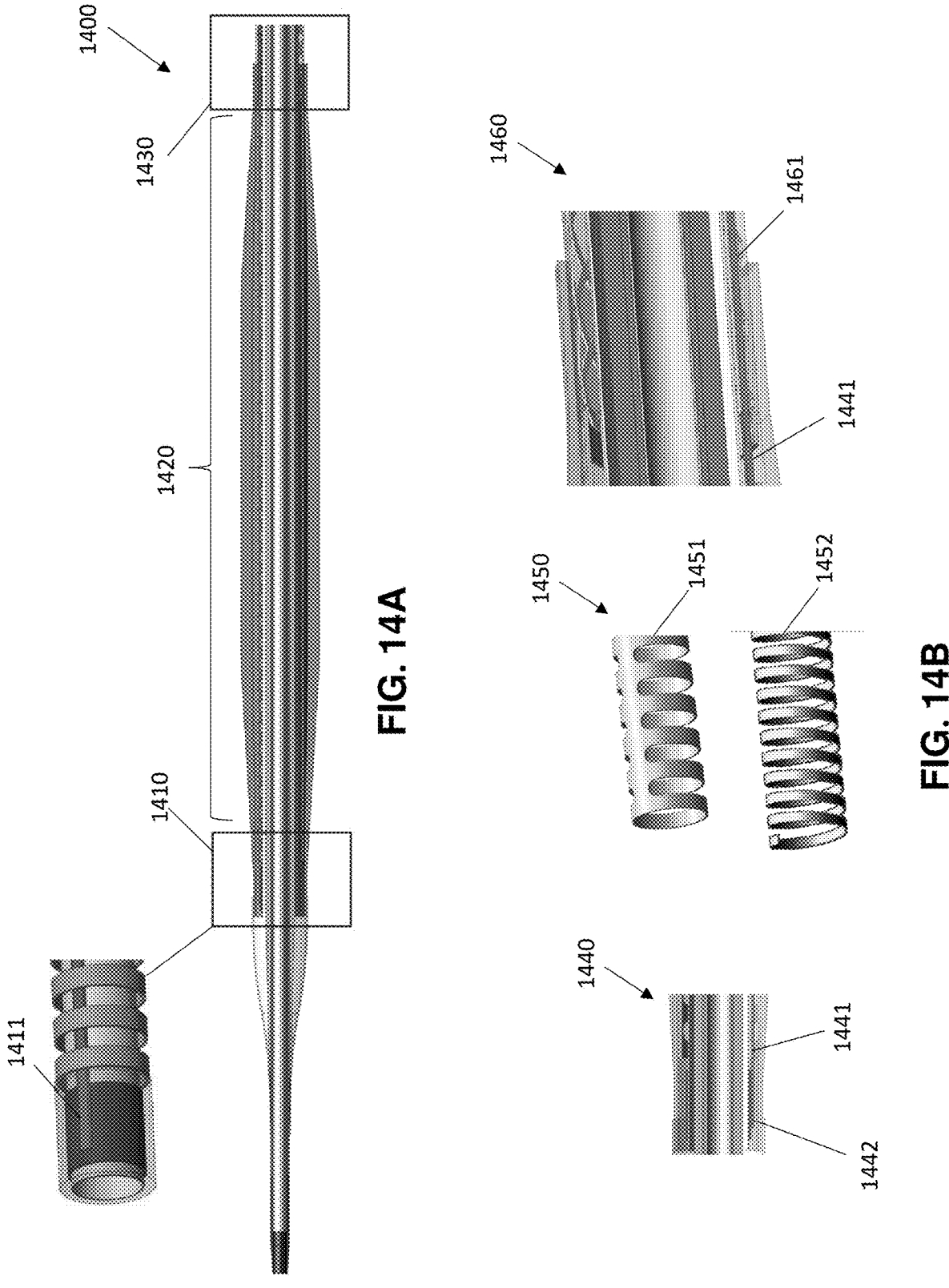
FIG. 14A shows a partial view of an arterial sheath inner catheter.
FIG. 14B shows some example elements of the arterial sheath inner catheter.

FIG. 14A shows a partial view of an arterial sheath inner catheter 1400. The arterial sheath inner catheter 1400 can be an example of the arterial sheath inner catheter 106 of FIG. 1. The arterial sheath inner catheter 1400 can include a first fused region 1410, an unfused region 1420, and a second fused region 1430. The first and second fused regions 1410, 1430 can be regions of the arterial sheath inner catheter 1400 where various layers and elements are fused together. In contrast, the unfused region 1420 may include those same or similar elements, but they may not be fused together. The unfused region 1420 may enable the arterial sheath inner catheter 1400 to more easily bend in response to a pull wire, such as pull wire 1411. In some examples, the unfused region 1420 may be between approximately 7-9 centimeters. In other examples, the unfused region 1420 can be any feasible length.

FIG. 14B shows some elements of the arterial sheath inner catheter 1400. Region 1440 can correspond to the first fused region 1410 and include a pull wire 1441 fused to a distal band 1442. Region 1450 shows various hypotube constructions that may be included within the unfused region 1420. Such constructions may enable the arterial sheath inner catheter 1400 to bend in response to a force provided through the pull wire 1441. For example, the hypotube may be a laser cut hypotube 1451 with a spine to control planar deflection. In another example, the hypotube can be a coil hypotube 1452. The coil hypotube 1452 can also be a spring hypotube.

Region 1460 can correspond to the second fused region 1430. The region 1460 shows the pull wire 1441 along with a lubricious lumen 1461 for the pull wire 1441. The lumen 1461 can allow the pull wire 1441 to move freely within the catheter-based ECMO system 100.

FIGS. 15A-15I show example steps of using the catheter-based ECMO system 100 of FIG. 1. The steps described herein are merely exemplary and are not meant to be limiting. Other steps may be used, and in some cases, these steps may be performed in a different order.

Figure 15C:
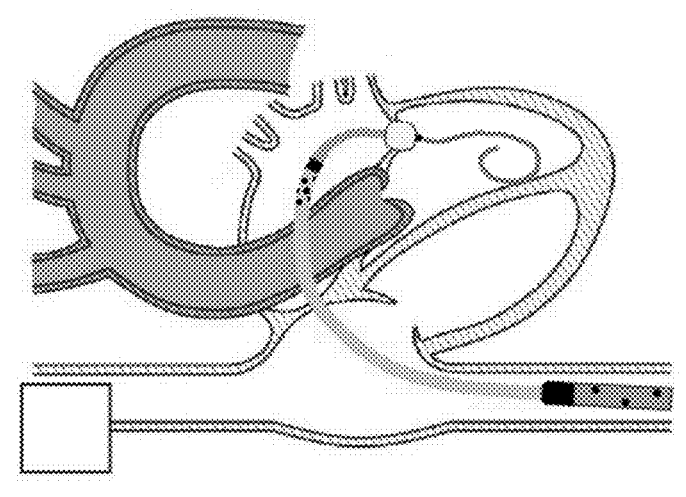
FIGS. 15A-15I show example steps of using the catheter-based ECMO system of FIG. 1.
Figure 15B:
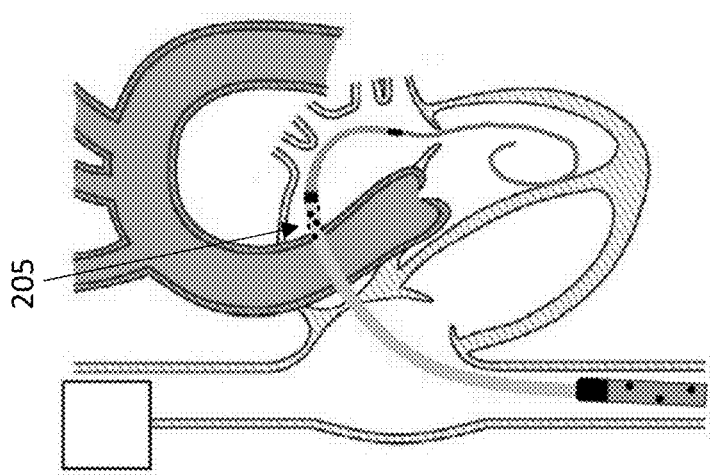
Figure 15A:
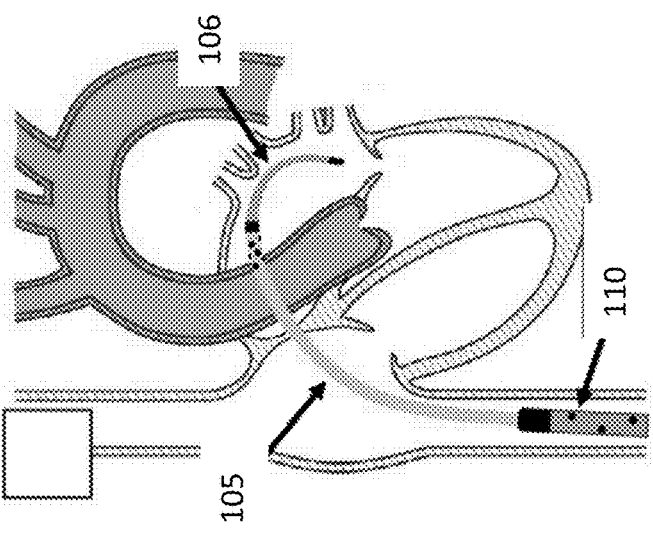

In FIG. 15A, the catheter-based ECMO system 100 is advanced through the atrial septum. In some examples, a 0.035 inch guidewire may be used to help position the catheter-based ECMO system 100. As shown, the venous sheath 110 may be within the inferior vena cava while the arterial sheath 105 and the arterial sheath inner catheter 106 may puncture the septum. The arterial sheath inner catheter 106 may be turned/bent/deflected (through a pull wire, for example) into the left atrium.

Next, in FIG. 15B, the guidewire may be advanced into the left ventricle. For example, the surgeon can guide the guidewire through the mitral valve. In some examples, the guidewire can be a relatively compliant (floppy) guidewire.

Next, in FIG. 15C, the arterial sheath 105, including one or more infusion holes 205 and arterial sheath inner catheter 106 can be advanced toward the mitral valve. In some cases, the surgeon may adjust deflection of the inner catheter to position a deflector (such as balloon 201 of FIG. 2) across the mitral valve. After positioning the balloon, the balloon can be inflated. In some examples, the balloon may be inflated by saline or gas. Inflation of the balloon helps to center the arterial sheath inner catheter with respect to the mitral valve and prevent the passage of the catheter between the mitral valve chordae tendinae. Note that advancement of the arterial sheath 105 and the arterial sheath inner catheter 106 can be independent of the venous sheath 110. Thus, the venous sheath 110 can remain in the inferior vena cava.

Figure 15F:
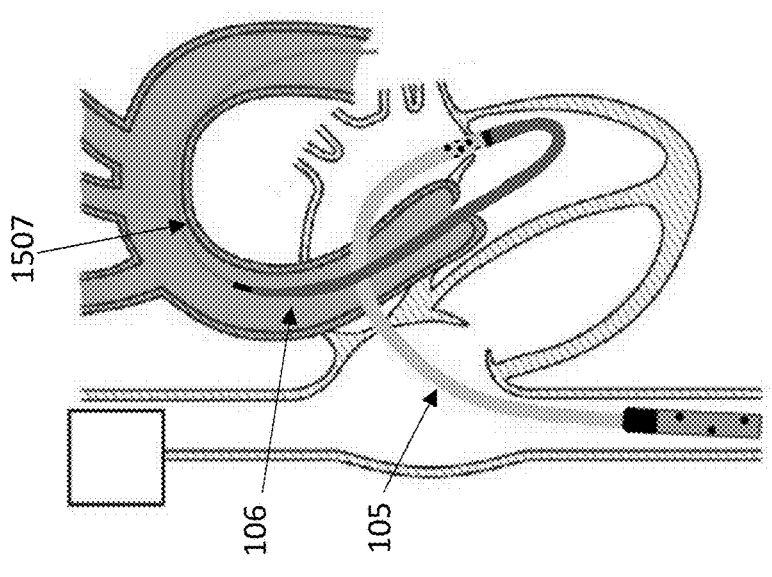
Figure 15E:
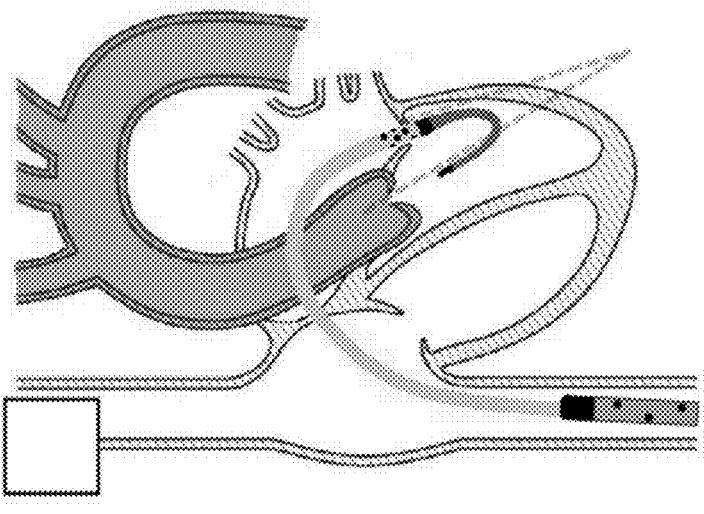
Figure 15D:
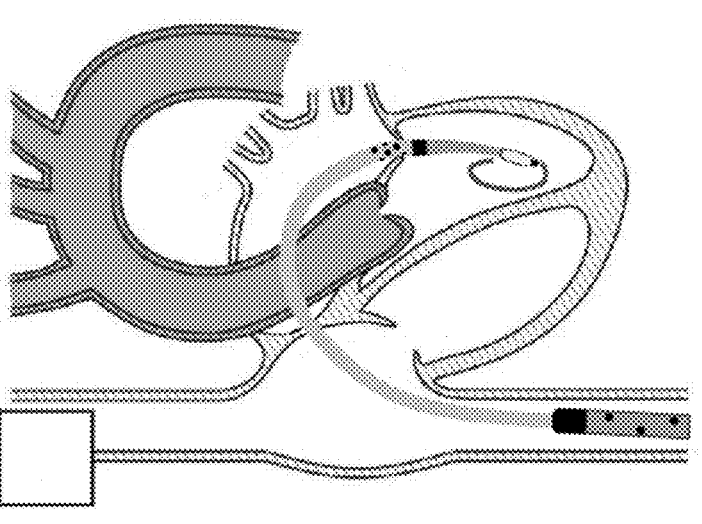

Next, in FIG. 15D after crossing through the mitral valve apparatus, the balloon may be deflated or left fully or partially inflated, and the arterial sheath 105 and the arterial sheath inner catheter 106 can be advanced across into the left ventricle. Generally, the surgeon can take care to position the arterial sheath inner catheter 106 and/or the guidewire using the inflated balloon to avoid any chordae tendineae.

Next, in FIG. 15E the distal tip of the arterial sheath inner catheter 106 is deflected until the distal tip of the arterial sheath inner catheter 106 is approximately centered with respect to the aortic valve. In some examples, the arterial sheath inner catheter 106 may be deflected more than about 140 degrees (e.g., more than 150 degrees, more than 160 degrees, more than 170 degrees, etc.). In other examples, the arterial sheath inner catheter 106 may be deflected by more than or less than 170 degrees. Deflection of the distal tip of the arterial sheath inner catheter 106 may be performed by moving a pull wire with a lever on a handle, as described herein. Alternatively or additionally, the inner catheter (daughter catheter) may be deflected by a wire (e.g., J-wire).

Next, in FIG. 15F, a relatively stiff guidewire 1507 may be introduced into the catheter-based ECMO system 100 and advanced antegrade through the left ventricle output tract and across the aortic valve, in some examples at least partially up the ascending aorta, and down the descending aorta. In some examples, the guidewire can be stiffer than the guidewire used earlier in FIGS. 15A-15D.

Figure 15I:
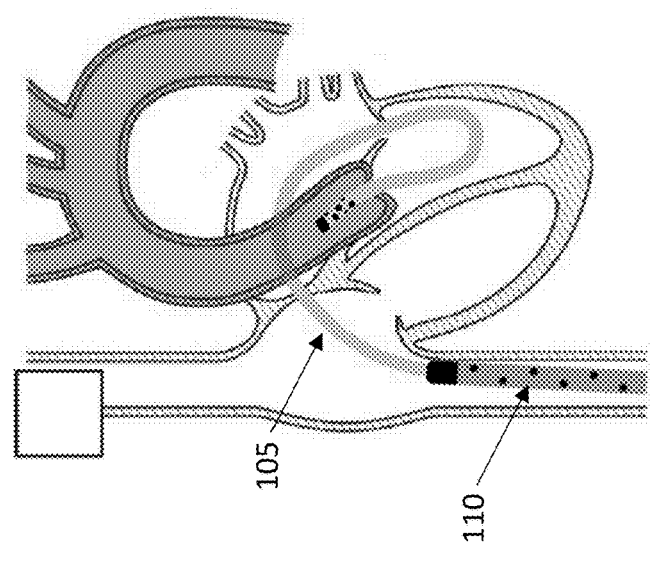
Figure 15H:
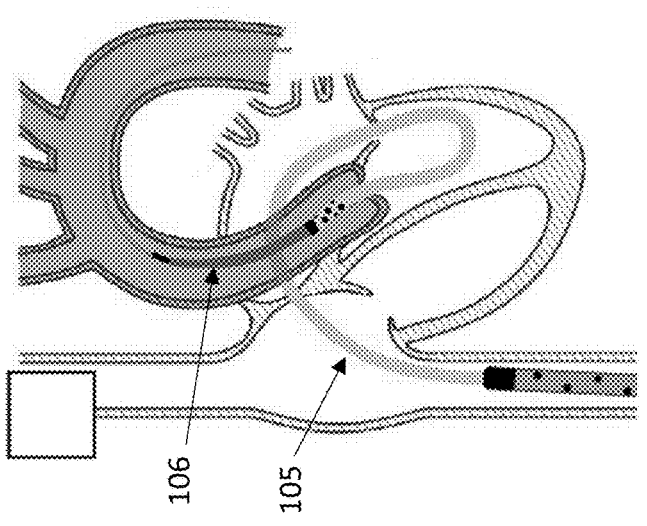
Figure 15G:
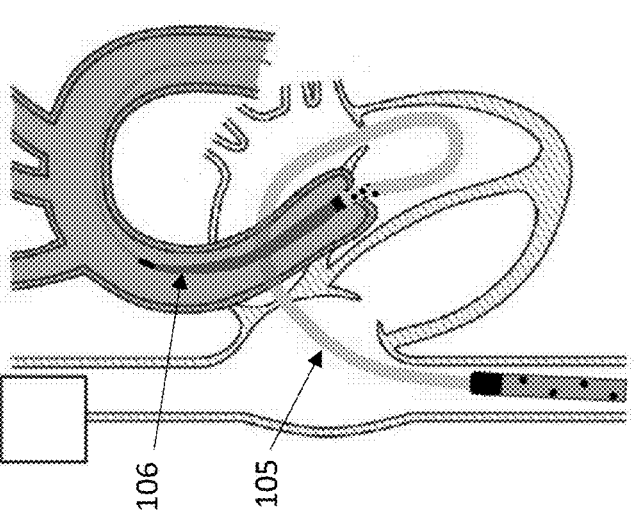

Next, in FIG. 15G, the arterial sheath 105 and the arterial sheath inner catheter 106 can be advanced over the guidewire until the distal end region (including the tip) of the arterial sheath 105 crosses the aortic valve and is positioned within the ascending aorta. In any of these methods, the distal end region (e.g., the tip) may be positioned in the aorta. It may be particularly advantageous to position the tip at least 3-7 cm (e.g., between 4-7 cm, between 5-6 cm, etc.), or so that the distal tip of the arterial sheath is at least about 1 cm above (distal to) the arterial valve within the aorta. This may prevent the tip from being propelled back into the ventricle when delivering blood through the aortic sheath. Thus, in any of these examples the tip of arterial sheath may be at least 1 cm above aortic valve, as shown in FIG. 15H.

The arterial sheath inner catheter 106 and/or the guidewire may then be completely withdrawn from the arterial sheath of the catheter-based ECMO system. In FIG. 15I the guidewire and inner (daughter) catheter have been removed. The catheter-based ECMO system 100 is now in position to remove oxygen-poor blood through the venous sheath 110 and return blood through the arterial sheath 105.

Figure 16B:
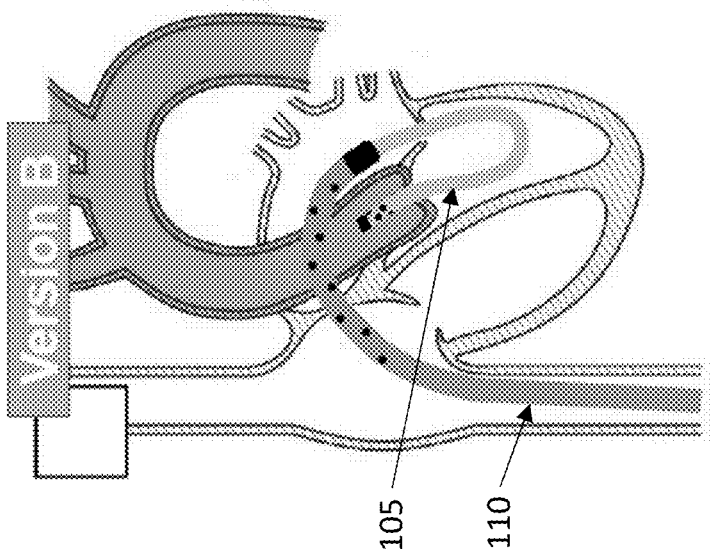
FIGS. 16A and 16B show possible configurations of a venous sheath and an arterial sheath for performing ECMO.
Figure 16A:
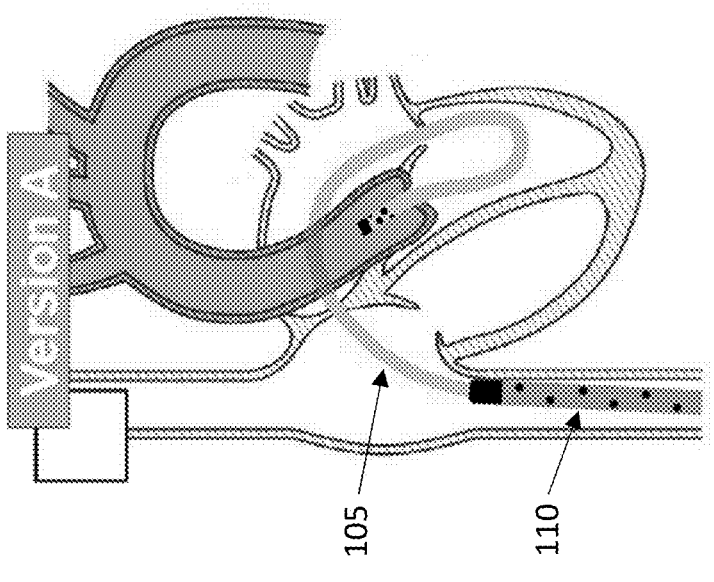

FIGS. 16A and 16B show possible configurations of the venous sheath 110 and the arterial sheath 105 for performing ECMO (or in FIG. 16B, ECMO and LAVA). In FIG. 16A, the venous sheath 110 is positioned within the inferior vena cava with the arterial sheath 105 positioned across the aortic valve. FIG. 16B shows an alternative configuration where the venous sheath may be positioned across the septum and side-holes are within the left atrium and the right atrium to allow "decompression" and volume reduction for the heart left and/or right sided chambers. In either configuration, oxygenated blood may easily be exchanged for oxygen poor blood in a percutaneous manner with a single-entry point into the patient.

In some cases, a slightly different approach may be used to perform ECMO for a patient. For example, a catheter-based ECMO system may include two separate catheters: a venous sheath to remove blood and an arterial sheath to return blood. In general, the arterial sheath can include the arterial sheath 105 and the arterial sheath inner catheter 106 of the catheter-based catheter system 100. The venous sheath can be a single catheter that simply includes the venous sheath 110 of FIG. 1. This approach may allow larger (bigger cross-sectional catheter areas) to allow greater blood flow from the pump. In this manner, a first catheter can be used for removing blood and a second (separate) catheter can be used to return blood to the patient. Example steps for using this alternative catheter-based ECMO system are described with respect to FIGS. 17A-17I.

FIGS. 17A-17I show example steps of using a two catheter-based ECMO system. The steps described herein are merely exemplary and are not meant to be limiting. Other steps may be used, and in some cases, these steps may be performed in a different order. A first catheter can be a catheter that supports venous sheath functionality (performs operations of the venous sheath 110 of FIG. 1). A second catheter 106 can be a catheter that supports arterial sheath 105 and arterial sheath inner catheter functionality (performs operations of the arterial sheath 105 and the arterial sheath 105 of FIG. 1.)

Figure 17C:
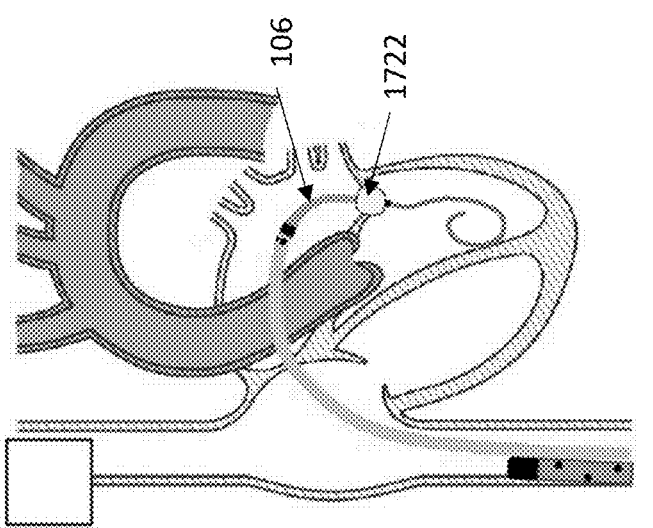
FIGS. 17A-17I show example steps of using a two catheter-based ECMO system.
Figure 17B:
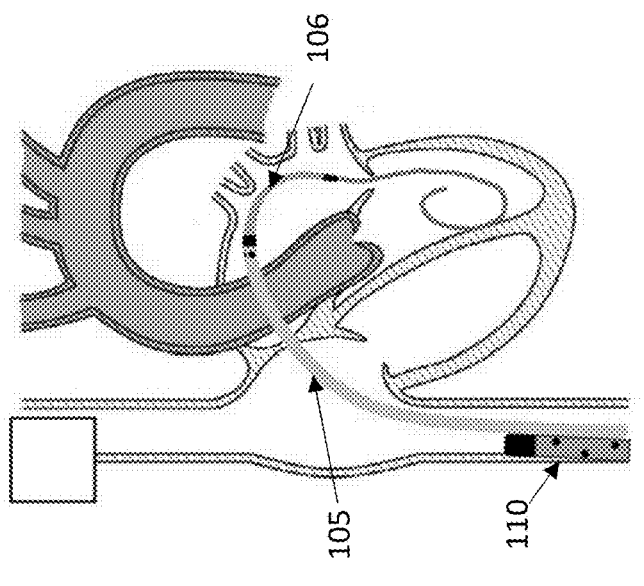
Figure 17A:
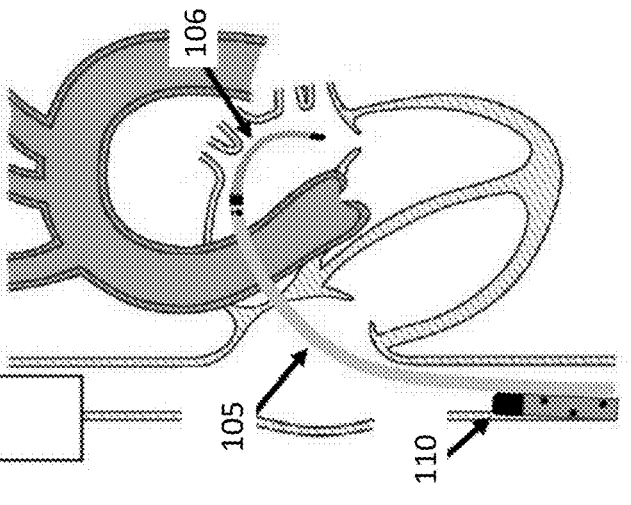

First, in FIG. 17A the arterial sheath 105 and the arterial sheath inner catheter 106 are advanced over a guidewire and through the atrial septum. Also, a separate venous sheath 110 is advanced to the inferior vena cava. Next, in FIG. 17B a floppy guidewire may be advanced into the left ventricle. Next, in FIG. 17C, the arterial sheath 105 and the arterial sheath inner catheter may be advanced toward the mitral valve. The expander (e.g., balloon 1722) on the inner catheter 106 may be positioned across the mitral valve and inflated. In this manner, the arterial sheath inner catheter 106 may be advanced across the mitral valve.

Figures 17D, 17E, 17F:
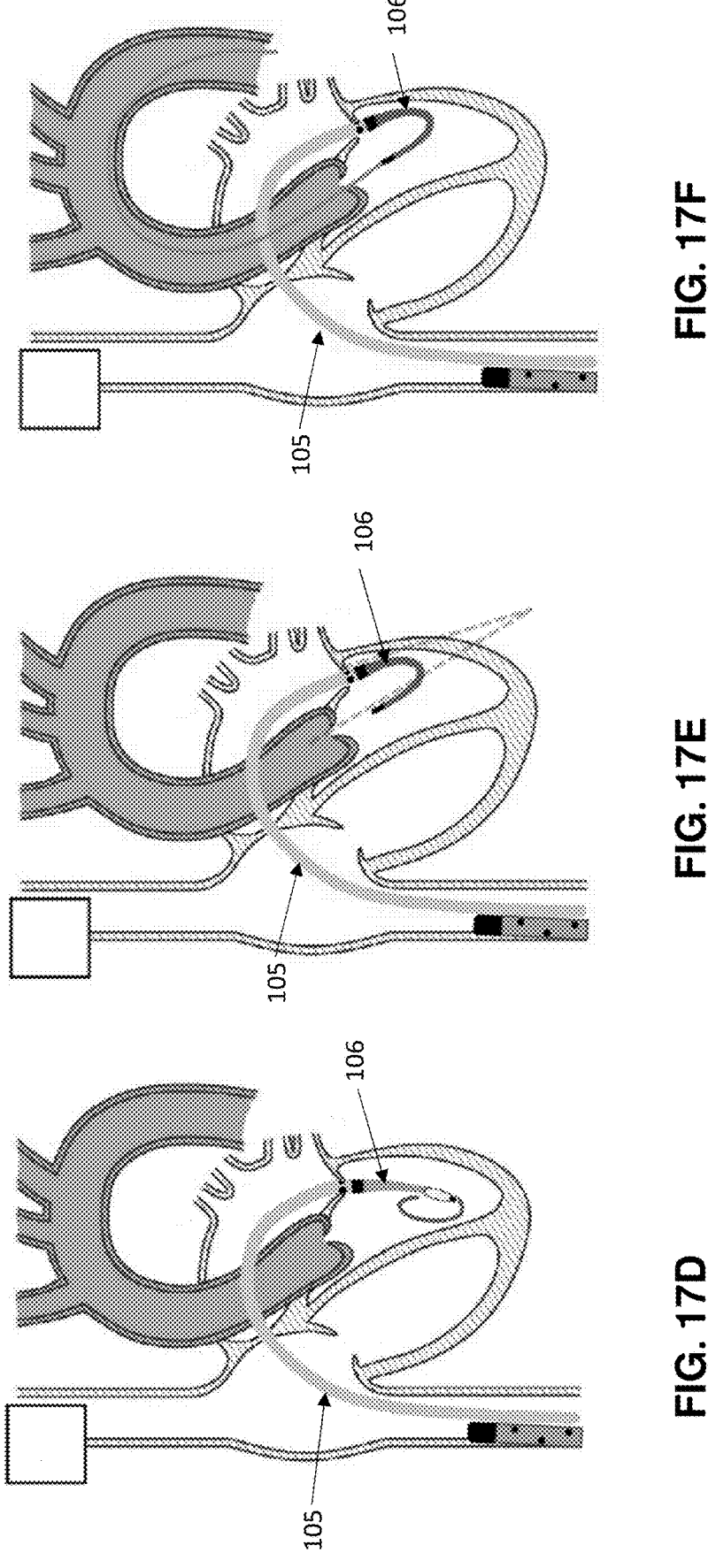

Next, in FIG. 17D, the arterial sheath 105 and the arterial sheath inner catheter 106 are advanced across the mitral valve into the left ventricle. The balloon may be left inflated, or semi-inflated, as the inner (daughter) catheter is advanced into the ventricle and to the aortic valve. For example, in FIG. 17E the distal tip of the arterial sheath inner catheter is deflected until approximately centered with respect to the aortic valve. In some examples, the arterial sheath inner catheter may be deflected between about 140-190 degrees (e.g., 170 degrees).

Figures 17G, 17H, 17I:
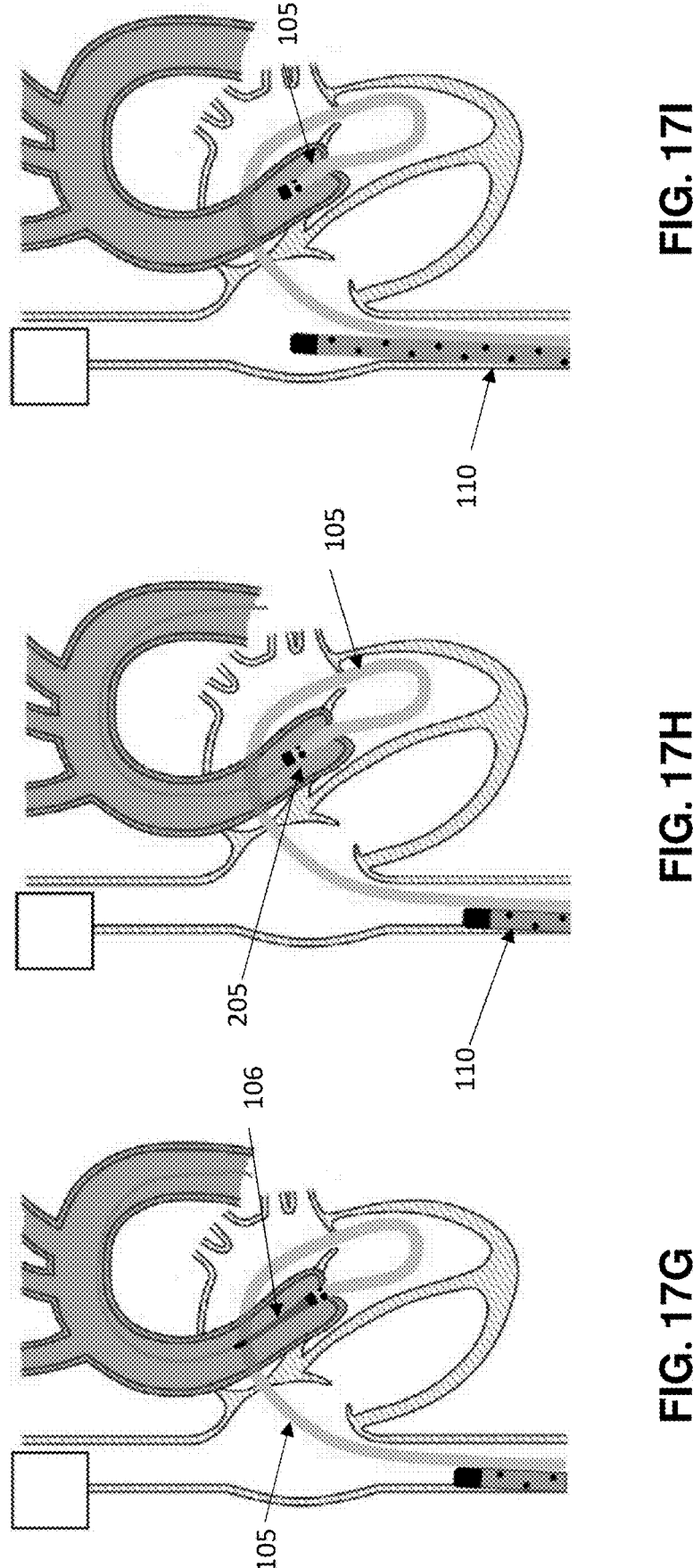

Next, in FIG. 17F, a stiff guidewire may be introduced into the catheter-based ECMO system and advanced antegrade through the left ventricle output tract and across the aortic valve, up the ascending aorta and optionally down the descending aorta. In FIG. 17G the arterial sheath 105 and the arterial sheath inner catheter 106 can be advanced over the guidewire (separately, e.g., advancing the inner catheter first, then the arterial sheath over the inner catheter and stiffer guidewire) until the tip of the arterial sheath crosses the aortic valve and is positioned within the ascending aorta, e.g., at least 1 cm distal to the valve, as shown in FIG. 17H.

The arterial sheath inner catheter and guidewire may then be completely withdrawn, as shown in FIG. 17I. Thus, the venous sheath can be positioned within the inferior vena cava. The example steps of FIG. 17A-FIG. 17I may be similar to steps described with respect to FIG. 15A-FIG. 15I, particularly due to the similarly of the functions of the arterial sheaths and the arterial sheath inner catheters used in both examples.

FIG. 18 is a flowchart showing an example method 1800 for performing ECMO with a catheter-based ECMO system. Some examples may perform the operations described herein with additional operations, fewer operations, operations in a different order, operations in parallel, and some operations differently. The method 1800 is described below with respect to the catheter-based ECMO system 100 of FIG. 1, however, the method 1800 may be performed by any other suitable system or device.

The method 1800 begins in block 1802 as a transeptal puncture is performed. In some examples, this operation may be optional, as indicated here by dashed lines. The transeptal puncture may be performed by a distal end of the catheter-based ECMO system 100, or any other feasible device.

Next, in block 1804 a catheter-based ECMO system is advanced into the patient. For example, the catheter-based ECMO system 100 may be inserted percutaneously into a femoral vein of the patient. The catheter-based ECMO system 100 may include a venous sheath 110, an arterial sheath 105, and an arterial sheath inner catheter 106.

Next, in block 1806, the arterial sheath inner catheter and the arterial sheath is advanced across the atrial septum. In addition, the arterial sheath inner catheter 106 is deflected within the left atrium. In some examples, the venous sheath 110 may be positioned within the inferior vena cava. Operations of block 1806 may be further described above with respect to FIG. 15A and FIG. 15B. Any of these apparatuses may include an outer member 110, e.g., sheath or venous sheath, that includes a plurality of openings (holes, gaps, windows, etc.) to allow inflow of un-oxygenated blood that may be removed, oxygenated, and returned through an inner catheter that is placed with a distal end in the ascending aortic arch, as described herein.

Next, in block 1808, an expander (e.g., a balloon on the inner/daughter catheter) is inflated and advanced within the mitral valve to center the catheter. For example, the balloon 201 of FIG. 2, may be inflated through the handle 125. Operations of block 1808 may be further described above with respect to FIG. 15C.

The arterial sheath inner catheter may be advanced 1810 into the left ventricle. For example, the arterial sheath inner catheter 106 may be advanced into the left ventricle over the guidewire. The operations of block 1810 may be further described above with respect to FIG. 15D. In some examples, the arterial sheath may be at least partially advanced over the arterial inner catheter, e.g., into the ventricle.

The arterial sheath inner catheter may then be deflected until the distal end is centered with respect to (and points towards) the aortic valve 1812. For example, the arterial sheath inner catheter 106 of the catheter-based ECMO system 100 may be deflected until a distal tip of the arterial sheath inner catheter 106 is pointed toward the center of the aortic valve. The operations of block 1812 may be further described above with respect to FIG. 15E. A guidewire (relatively stiff guidewire) may be advanced distally through the valve and into the aortic arch.

The arterial sheath inner catheter may then be advanced 1814 across the aortic valve, e.g., over a guidewire that was previously advanced. Once the arterial sheath inner catheter is in positioned in the aortic arch, the aortic sheath may be advanced distally over the supporting inner catheter and guidewire 1816, e.g., so that the distal end (distal tip) of the arterial sheath is at least 1 cm from the aortic valve 1816. Once the arterial sheath is in position sufficiently distal to the valve so that it will not be kicked back into the ventricle, the arterial sheath inner catheter and guidewire may be withdrawn (either together or separately). For example, the arterial sheath 105 may be advanced over the arterial sheath inner catheter 106 and guidewire across the aortic valve. After this advancement, the arterial sheath inner catheter 106 can be withdrawn from at least the arterial sheath 105. The operations of block 1814 may be further described with respect to FIGS. 15F-15I. Thereafter, the arterial sheath and venous sheath may then be coupled to an ECMO pump apparatus and ECMO performed 1816.

FIG. 19 is a flowchart showing an example method 1900 for performing ECMO with a two catheter-based ECMO system. Such a system may include a first catheter that removes blood from the patient and a second catheter that returns blood to the patient. The first catheter can include a venous sheath, similar to the venous sheath 110 of FIG. 1. The second catheter can include an arterial sheath and an arterial sheath inner catheter, similar to the arterial sheath 105 and the arterial sheath inner catheter 106 of FIG. 1. These catheters may releasably (and sealingly) engage with each other as described herein.

The method 1900 may include performing a transeptal puncture 1902. In some examples, this operation may be optional, as indicated here by dashed lines. A venous sheath may be advanced into the patient 1904. Also, an arterial sheath inner catheter may be advanced into the patient. In some examples, the venous sheath may be advanced through a first femoral artery while the arterial sheath and arterial sheath inner catheter may be advanced through a second femoral artery while arranged concentrically (see, e.g., FIGS. 16A-16B).

The arterial sheath inner catheter may be advanced across the atrial septum 1906. Optionally, the venous sheath may be positioned in the inferior vena cava. Operations of block 1906 may be further described above with respect to FIG. 17A and FIG. 17B.

In some examples, the balloon (e.g., expander) may be inflated 1908 within the mitral valve to center the catheter. Operations of block 1908 may be further described above with respect to FIG. 17C.

Next, in block 1910 the arterial sheath inner catheter (with the balloon fully or partially inflated) may be advanced into the left ventricle. The arterial sheath inner catheter may be deflected 1912 until the distal tip of it is centered with respect to the aortic valve. For example, the arterial sheath inner catheter may be deflected until a distal tip of the arterial sheath inner catheter is pointed toward the center of the aortic valve. Optionally a second guidewire, which may be heavier that the first guidewire, may be advanced distally into the aortic arch.

The arterial sheath inner catheter and may then be advanced (e.g., over the guidewire) across the aortic valve so that the distal tip extends distally into the aortic arch 1914. Once the distal end of the aortic is positioned, e.g., greater than about 1 cm distal to the valve, then the arterial sheath may be advanced 1914. After this advancement, the arterial sheath inner catheter and guidewire can be withdrawn from the arterial sheath, the arterial sheath and venous sheath may be coupled to the ECMO pump and ECMO may be performed 1916.

Also described herein are methods in which the inner catheter is advanced across the mitral valve around the apex and into the ascending aorta, as described above, but without advancing the outer catheter (e.g., arterial sheath) until the inner catheter is positioned within the ascending aorta. The method may be performed without individual arterial sheath and arterial sheath inner catheters; in some cases a single arterial sheath/catheter may be used, which may include features of either or both the arterial sheath and arterial sheath inner catheters described above. Sequentially, the outer catheter may then be advanced over the inner catheter and advanced all the way past the mitral valve around the apex and into the aorta.

In any of these examples the venous sheath/catheter, which may include a plurality of inflow holes, may be coaxially (or optionally separately) positionable relative to the arterial sheath/catheter(s). In some cases the venous sheath/catheter may be coaxially (and sealing) arranged to move over the arterial sheath/catheter(s). Although in many of these examples the venous sheath/catheter is configured to be positioned within the inferior vena cava, e.g., so that the inflow openings (inflow holes) are positioned within the inferior vena cava, in some cases, the venous sheath/catheter may be configured to be positioned within the heart, e.g., near the aortic valve, or in the atria (e.g., for LAVA).

In any of the apparatuses described herein, the balloon may be highly compliant. For example the balloon may be formed of a highly complaint material such as a synthetic silicone that is biocompatible. In some cases the synthetic silicone material comprises a cross-linked polymer which is reinforced with silica.

In any of the methods and apparatuses described herein the inner and/or outer surfaces of any of the catheters/sheaths described (e.g., first and/or second arterial sheath, venous sheath, etc.) may be coated with a heparin coating to an inner and/or outer surface. This may be particularly beneficial for those catheters that may remain in the body for several days. Any appropriate coating may be used, including a covalently bound heparin. For example, heparin can be covalently bound to the outer and/or inner surface by crosslinking heparin to the surface or to an intermediate (e.g., collagen) that is bound to the surface(s) of the catheter. Other examples of covalently bound coatings of heparin include CARMEDA® BioActive surface treatments.

Figure 20:
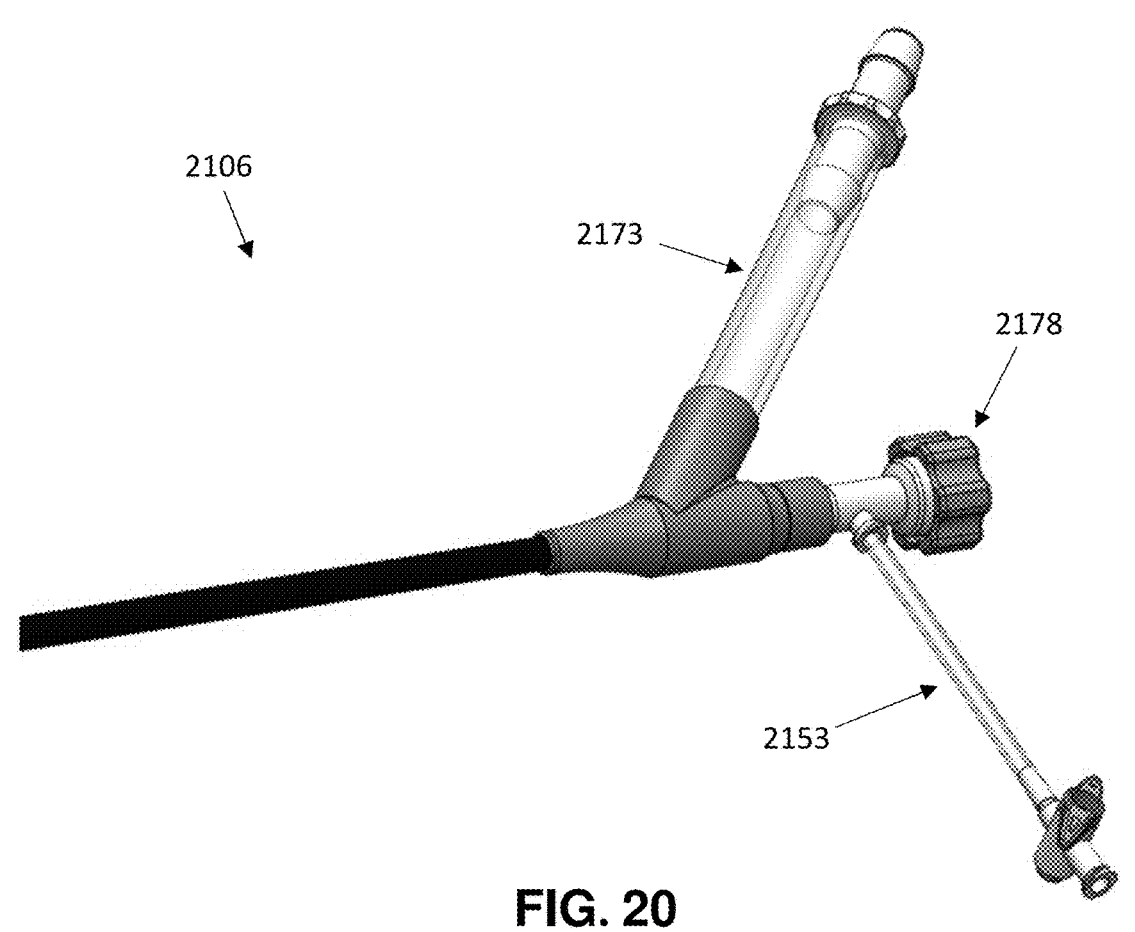
FIG. 20 shows an example of a proximal end region of an inner catheter of an ECMO system as described herein.
Figure 21:
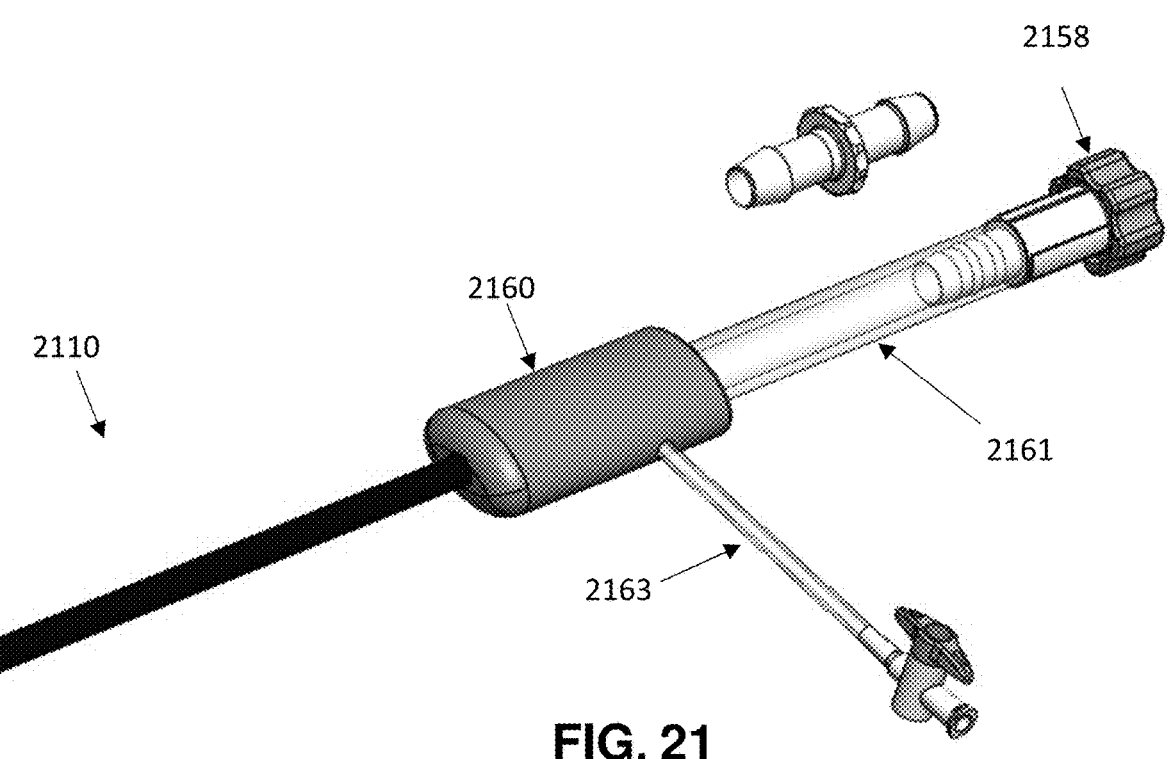
FIG. 21 shows an example of a proximal end region of an outer catheter of an ECMO system as described herein.

FIGS. 20 and 21 illustrate examples of proximal regions of an inner (e.g., aortic) sheath and/or outer (e.g., venous) sheath, respectively. In general, the inner arterial catheter and/or arterial sheath may be configured to be advanced distally and steered, using pre-bent regions and/or one or more guidewires, as described herein. The outer (e.g., venous) sheath may be more passively configured to track over the arterial sheath and/or catheter. Thus, in general, any of the inner arterial catheter (e.g., inner sheath) and/or arterial sheaths described herein may be configured to be significantly longer than the outer venous sheath (e.g., outer sheath), by at least some minimum distance, such as 20 cm, 25 cm, 30 cm, 35 cm, 40 cm, 45 cm, 50 cm, 55 cm, 60 cm, 65 cm, etc. or longer. In some cases the inner arterial catheter and/or arterial sheath is configured to be at least 60 cm longer than the outer venous sheath. The inner arterial catheter and/or arterial sheath typically advances through heart ahead of the outer venous sheath, and the inner arterial catheter and/or arterial sheath may advance through a one-way valve (such as, but not limited to, a Tuohy-Borst valve 2158) at a proximal end region of the venous sheath (sec, e.g., FIG. 21). The inner arterial sheath (and/or first inner arterial catheter) may be advanced through this valve to prevent bleeding as the catheters are advanced/retracted independently of each other.

FIG. 21 illustrates one example of a proximal end region of a venous sheath 2110 that includes a gripping or handle region 2160 that connects proximally to a short length of hemostatic valve compliant tubing 2161 and terminates in a one-way valve 2158. The proximal end also includes a connection to the blood removal port 2163 for connecting to an ECMO system, as described above.

The inner arterial sheath and/or first arterial catheter may be tapered at the distal end region, as described above. In any of these examples the distal tip region may be tapered to a narrowing of, e.g., between 5 F and 18 F (e.g., 5 F, 5.5 F, 6 F, 7 F, 8 F, 9 F, 10 F, 11 F, 12 F, etc.) and may be slightly larger (e.g., 15 F, 16 F, etc., such as between about 14 F and 20 F, between 14 F-18 F, between 15 F-16 F, etc.) more proximally. The distal taper does not need to be linear, e.g., from the tip to the body of the sheath/catheter). As described above, either or both the inner arterial sheath and/or first arterial catheter may include a balloon that is inflatable near the distal end region. In any of these methods and apparatuses, the balloon may be inflated to help position the distal end of the inner arterial sheath and/or first arterial catheter, by acting as a 'sail' to provide flow-directed positioning through the heart, taking advantage of blood flow through the heart. In some cases the inner arterial sheath and/or first arterial catheter may be deflectable to extend to greater than sixty degrees (e.g., greater than 80, 90, 100, 110, 120, 130, 140, 150, 160, 170, 180, 190, 200 degrees) over at least the distal-most 5 cm (e.g., 3-4 cm.

Any of these sheaths/catheters (e.g., the venous sheath, inner arterial sheath and/or first arterial catheter) may include one or more radiopaque markers, e.g., for visualization under fluoroscopy. For example, the outer catheter may include a metal marker (e.g., barium tungsten, etc.) at the distal end region. In some cases one or more regions of the venous sheath, inner arterial sheath and/or first arterial catheter may be reinforced, e.g., with a coil region. For example the venous sheath may be formed of a low-durometer PEBAX material over much of its length but may be reinforced with a coil and/or braided material to prevent kinking and/or to allow maximum flexibility, particularly at the distal end region (e.g., the distal-most 60-100 cm, e.g., 60-80 cm, etc.). The more proximal region (e.g., the proximal 110 cm, proximal 80-140 cm, etc.) may be formed of a higher durometer construction.

Thus, in general, in any of these methods and apparatuses, the inner arterial sheath (e.g., inner sheath) and/or first arterial catheter may be much longer and significantly more flexible than the outer venous sheath (e.g., outer sheath). This is true in systems including just a single inner arterial sheath (rather than an inner arterial sheath and a first arterial catheter) in addition to a venous sheath. More flexible may refer to the overall flexibility of the catheter/sheath or may refer to the flexibility of the distal end regions (e.g., the distal-most x cm, such as 5 cm, 7.5 cm, 10 cm, 12.5 cm, 15 cm, 20 cm, 25 cm, etc. or more). Flexibility may be measured by any appropriate manner, including determining the flexural modulus or bending modulus (e.g., in pascal (Pa), megapascals (MPa), pounds per square inch (psi), etc.). In some cases flexibility may be measured by flexural rigidity (e.g., in force per unit length, such as N/mm). For example, the outer sheath may have a flexural rigidity that is greater than 5% (e.g., 8% or more, 10% or more, 13% or more, 15% or more, 20% or more, 25% or more, 30% or more, etc.) of the flexural rigidity of the inner sheath or first arterial catheter. In some cases, the flexibility may be estimated based on the minimum bending radius (e.g., the smallest radius of curvature the catheter can bend into without kinking or significantly changing its shape), which may be measured in mm. Thus the inner arterial sheath (e.g., inner sheath) and/or first arterial catheter may have a minimum bend radius that is less than about 5% or less of the minimum bend radius (e.g., 6% or less, 7% or less, 8% or less, 9% or less, 10% or less, 12% or less, 15% or less, 20% or less, 30% or less, 40% or less, 50% or less, etc.) than the minimum bend radius of the outer venous sheath (e.g., outer sheath).

FIG. 20 shows an example of a proximal end region of an inner arterial sheath (in some examples, a second inner arterial sheath/catheter) 2106. This proximal end region also includes a one-way valve 2178 for receiving a guidewire. The proximal end region also includes a connection to an oxygenated blood input 2173 (e.g., coupling to an ECMO apparatus, as described above). In some cases the proximal end region may also include a connection to an inflation (e.g., saline inflation) port 2153.

The proximal connections shown in FIGS. 20-21 may allow the user to change from a hemostatic valve to the barbed connector to hook up to the arterial output from the ECMO machine.

FIGS. 22A-22G illustrate another example of a method of using a system for performing ECMO as described herein, similar to that shown in FIGS. 17A-17I, in which a separate venous input catheter (not shown) is used, e.g., and may be positioned within the heart, within the inferior vena cava, etc., including in tandem with the second inner arterial sheath/catheter and/or first inner arterial catheter. In some cases the venous sheath (venous input catheter) may be concentric over the arterial sheath.

In FIG. 22A, the septum 2281 may be dilated, as described above, and the first inner arterial catheter 2205 may be delivered to the left atrium; the arterial sheath 2206 may be passed over the first inner arterial catheter and parked in the left atrium, as shown in FIGS. 22A-22B, while the first inner arterial catheter 2205 is advanced through the heart. In later steps the arterial sheath 2206 may be advanced over the first inner catheter 2205 and/or over a guidewire 2216. In some examples the balloon 2222 may be at least partially inflated and a minimal length of guide wire 2216 may be extended in front of the first inner arterial catheter 2205, so that the balloon crosses completely through the mitral apparatus to the apex of the left ventricle. The balloon itself may crosse through the mitral valve and the chordae tendinea and may prevent damage to the structures within the heart. In some examples the diameter of the balloon may be about half the size of the orifice of the mitral orifice/annulus.

In FIG. 22C the first inner arterial catheter 2205 with the inflated (or partially inflated) balloon 2222 is advanced distally into the apex and deflected very sharply, as shown in FIG. 22D. Once the first inner arterial catheter 2205 is oriented towards the aortic valve, the guidewire 2216' (which may be the same guidewire or a different guidewire) may be advanced through the aortic valve and into the ascending aorta, aortic arch, and/or the descending aorta. The first inner arterial catheter 2205 may be advanced over the guidewire 2216', as shown in FIG. 22E. Once in position the arterial sheath 2206 may then be advanced over the first inner arterial catheter 2205 to position the infusion holes 2228 (and distal end opening) within a target region of the ascending aorta (e.g., between the aortic valve and the innominate artery), the aortic arch (e.g., lateral to the left carotid artery and/or left subclavian artery), or within the descending aorta. Once in position, as shown in FIG. 22G, the first inner arterial catheter 2205 and/or guidewire 2216' may be withdrawn proximally and removed from the lumen of the second arterial catheter 2206. As mentioned, a venous sheath (not shown in FIGS. 22A-22G) may be included for a venous supply into the ECMO system. Both venous sheath and arterial sheath may be connected to the external ECMO pump and arterial/oxygenated blood may be pumped into the ascending aorta from the openings 2228' in the second arterial catheter 2206. In some cases the venous sheath (not shown) may be present, e.g., in the inferior vena cava.

The example shown in FIGS. 23A-23G is similar to that shown in FIGS. 22A-22G, except that a venous sheath 2310 may be positioned coaxially over the second arterial catheter 2306, as shown in FIG. 23F-23G. For example, In FIG. 23A, the septum is dilated and the first inner arterial catheter 2305 is advanced into the left atrium; the arterial sheath 2306 may be coaxially over the first inner arterial catheter 2305 and may be parked at the left atrium, as shown in FIGS. 23A-23B, while the first inner arterial catheter 2305 (also referred to herein as simply the inner arterial catheter 2305) is advanced through the heart. In later steps the arterial sheath 2306 may be advanced over the first inner catheter 2305 and/or over a guidewire 2316. The balloon 2322 may be at least partially inflated and a minimal length of guide wire 2316 may be extended in front of the first inner arterial catheter 2305, so that the balloon crosses completely through the mitral apparatus to the apex of the left ventricle. The balloon may cross through the mitral valve and the chordae tendinea and may prevent damage to the structures within the heart. In some examples the diameter of the balloon may be about half the size of the orifice of the mitral orifice/annulus.

In FIG. 23C the first inner arterial catheter 2305 with the inflated (or partially inflated) balloon 2322 is advanced distally into the apex and deflected very sharply, as shown in FIG. 23D. This deflection may be performed as described herein. For example, a guidewire (pre-bent/J-wire) may be used, the distal end region may be steered (e.g., by a pull wire), the guidewire may be steerable, etc. Once the first inner arterial catheter 2305 is oriented towards the aortic valve, the guidewire 2316' (which may be the same guidewire or a different guidewire) may be advanced through the aortic valve and into the ascending aorta, aortic arch, and/or the descending aorta. The first inner arterial catheter 2305 may be advanced over the guidewire 2316', as shown in FIG. 23E. Once in position, the arterial sheath 2306 may then be advanced over the first inner arterial catheter 2305 to position the infusion holes 2328 (and distal end opening) of the arterial sheath 2306 within a target region of: the ascending aorta (e.g., between the aortic valve and the innominate artery), the aortic arch (e.g., lateral to the left carotid artery and/or left subclavian artery), or the descending aorta. Once in position, as shown in FIGS. 23F-23G, the first inner arterial catheter 2305 and/or guidewire 2316' may be withdrawn proximally and removed from the lumen of the second arterial catheter 2306. An outer venous sheath 2310 may be coaxially advanced over the arterial sheath 2306, as shown in FIGS. 23F-23G, to provide inflow into the ECMO system. In some examples the venous sheath 2310 is fixed to the arterial sheath 2306. In some cases the venous sheath 2310 is slidable over the arterial sheath 2306 but may sealingly engage with an outer surface of the arterial sheath.

Outflow for the ECMO system may be from the arterial sheath 2306. Thus, arterial/oxygenated blood may be pumped into the ascending aorta from the openings 2328' in the second arterial catheter (arterial sheath) 2306, including the distal end opening. In FIG. 23F the venous sheath 2306 is shown being advanced distally over outside of the second arterial sheath/catheter 2306 and positioned with the inflow holes within the inferior vena cava. For example, the larger French outer venous return catheter (venous sheath) 2310 may be positioned so that the inflow holes 2321 are within the inferior vena cava, in some cases as across from the septum with the distal portion of the outer venous return catheter 2310 sitting in the left atrium and the proximal portion in the right atrium. In some examples the outer venous return catheter (venous sheath) 2310, including the side holes 2321 may be positioned in the right atrium. For example, the side holes (inflow holes) shown in FIGS. 23F and 23G may traverse the atrial septum and/or may be in the left atrium to remove both left atrial and right atrial blood as the "venous/atrial" return. In some examples the side holes may be positioned in the right atrium and/or the inferior vena cava and/or the ascending aorta. In any of these examples the venous sheath may be configured to perform Left Atrial Veno-Arterial Extracorporeal Membrane Oxygenation (LAVA), as shown in FIG. 23G. For example, the inflow holes 2321 in the venous sheath 2310 may be positioned in the right atrium, the left atrium, or both the right and left atria. This may be referred to as a LAVA-ECMO configuration. The venous sheath may be configured so that the inflow holes extend sufficiently down the length of the distal end region of the venous sheath so as to span either just the right atrium, the left atrium, or both the left and right atrium when used (e.g., guided by visualization markers).

Arterial Sheath Sets

Also described herein are systems including sets of interlocking/engaging venous sets (e.g., venous sheath and catheters, such as dilator catheters) and arterial sets (e.g., arterial sheath and catheters, such as dilators, steering catheters, etc.) for performing venous ECMO. In some cases these apparatuses may be part of a system for performing ECMO, and in some cases may be adapted specifically for performing Left Atrial Veno-Arterial Extracorporeal Membrane Oxygenation (LAVA-ECMO). LAVA-ECMO is a type of ECMO that provides circulatory support and simultaneous left ventricular unloading. Examples of the particular type of LAVA-ECMO described herein are illustrated and described below, as well as in FIGS. This method may include pacing the inlet openings for the venous sheath (e.g., outer venous sheath) in the left atrium to drain blood and the arterial sheath in the ascending aorta and/or aortic arch.

Figure 24:
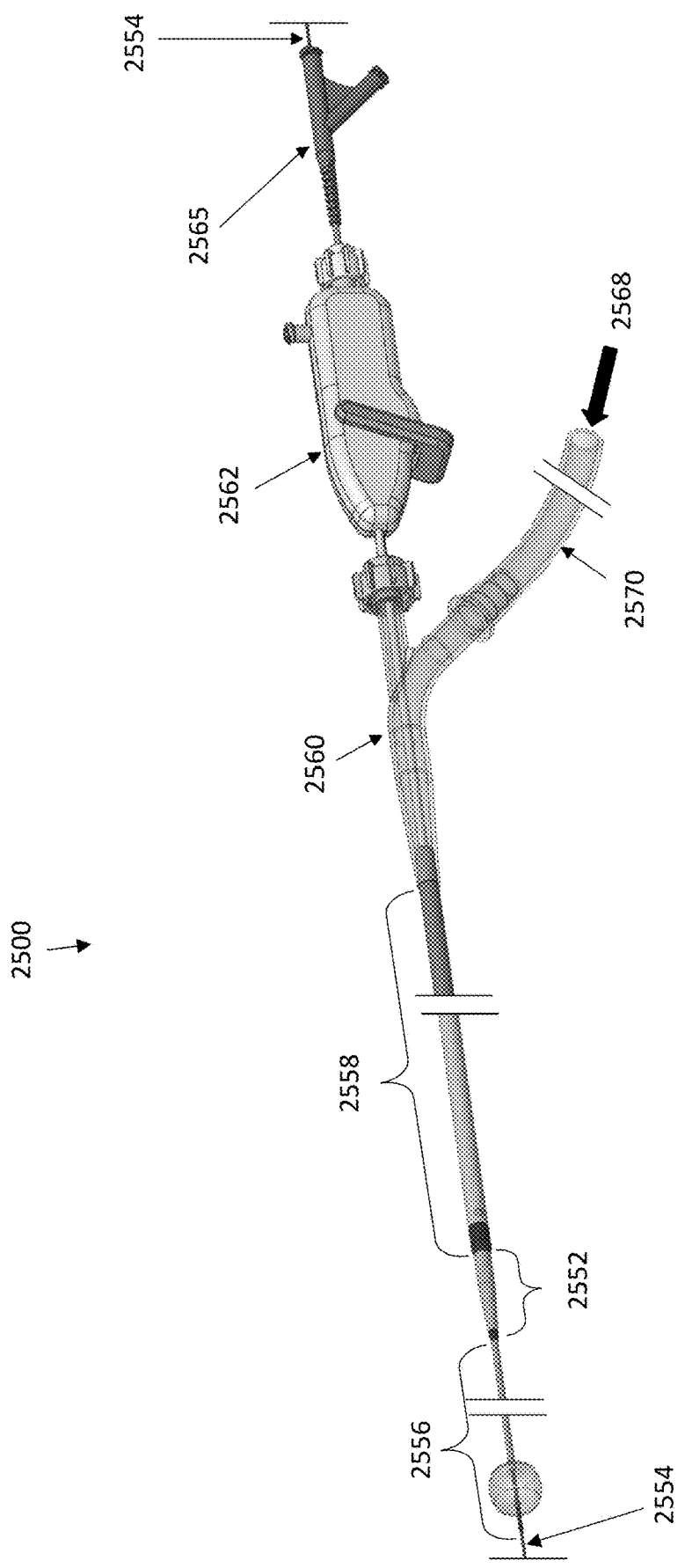
FIG. 24 shows an example of a catheter-based ECMO system including child, mother and granddaughter nested components (e.g., an arterial sheath set).

FIG. 24 illustrates one example of a portion of an ECMO apparatus including an arterial sheath set of communicating and arterial catheters that may be used with (and may engage with) a venous sheath set. An arterial sheath set such as the one shown in FIG. 24 may include an arterial sheath (referred to herein as a "mother" catheter), and one or more inner catheters for dilating (e.g., including an expandable balloon) and/or deflecting (e.g., steering, including one or more controllable bending axis). Any of these sets (arterial sheath sets and/or venous sheath sets) may be used with one or more guidewires.

For example, FIG. 24 shows an assembled example of one arterial sheath set 2500. This example includes an arterial sheath 2558 ("mother catheter") that includes a hub region 2560. The arterial sheath 2558 is configured to infuse arterial blood from a distal opening and/or one or more openings through the outer surface of distal end region of the flexible elongate body of the mother catheter 2558. The hub 2560 of the arterial sheath may include connection to a tubing 2570 (e.g., between ¼" and ½" tubing, ⅜" tubing, etc.) for coupling 2568 to an arterial flow portion of an ECMO oxygenator (not shown). The hub of the arterial sheath may also couple to a valve (e.g., a hemostasis valve) in-line with the long axis of the arterial sheath, through which the other arterial sheath set catheters (e.g., inner catheters) may be inserted. In FIG. 24 the arterial sheath set 2500 includes a first inner catheter (referred to herein as a first arterial sheath inner catheter, or a daughter catheter) and a second inner catheter (referred to herein as a second arterial sheath inner catheter, or a granddaughter catheter). In this example the first inner catheter is configured as a first daughter catheter that is steerable and include a tendon-controllable deflection region at the distal end, as described in greater detail in FIGS. 30A-30B and 31A-31G. In FIG. 24, the first inner catheter includes a proximal handle 2562 that include a control to adjust the amount of deflection of the distal end region (e.g., between 0 degrees/undeflected and 180 degrees, retroflexed, such as between 0-170 degrees, between 0-165 degrees, between 0-160 degrees, between 0-150 degrees, between 1-155 degrees, between 0-140 degrees, between 0-145 degrees, etc.). Thus, the distal end region of the first arterial sheath inner catheter (e.g., daughter catheter) may be highly compliant and controllably steerable. The first arterial inner sheath catheter is nested within the mother catheter and may be configured so that the inner surface of the distal end region of the mother catheter releasably engages against the outer surface of the distal end region 2552 of the first arterial sheath inner catheter, as described above. For example, the distal end region of the first arterial sheath inner catheter may have an outer diameter that is approximately the same as the inner diameter of the distal end region (which may include a distal tapering region) of the mother catheter. This releasably engagement may provide a friction fit that may seal the two at the distal end region of the mother catheter. In some cases the distal end region (proximal to the distal end) of the first arterial sheath inner catheter may include an engagement region, such as a protrusion, which may be a ring, bump, etc., extending slightly proud of the outer surface of the distal end region of the first arterial sheath inner catheter that may releasably engage with an inner region at the tip of the mother catheter; in some cases the mother catheter may include a recessed region to engage with this engagement region. Either or both the distal tip region of the mother catheter (arterial sheath) and the engagement region of the first arterial sheath inner catheter (daughter catheter) may be formed of a low-durometer material that may compress and/or stretch to engage and form a temporary seal when engaged.

The second arterial sheath inner catheter is shown nested within the first arterial sheath inner catheter. In this example the second arterial sheath inner catheter (e.g., granddaughter catheter) may be configured as a highly compliant catheter including an expandable displacement element (e.g., balloon, basket, etc.) on the distal end region. In FIG. 24 the granddaughter catheter is shown with the distal end region 2556 extending distally from, and engaged with (e.g., sealingly with) the distal end of the daughter catheter 2552. The second arterial inner sheath catheter (the granddaughter catheter) is nested within the daughter catheter and may be configured so that the inner surface of the distal end region of the daughter catheter releasably engages against the outer surface of the distal end region 2552 of the second arterial sheath inner catheter (granddaughter catheter). This releasably engagement may provide a friction fit that may seal the two at the distal end region of the daughter catheter. For example, the distal end region of the second arterial sheath inner catheter (granddaughter catheter) may have an outer diameter that is approximately the same as the inner diameter of the distal end region (which may include a distal tapering region) of the daughter catheter. In some cases the distal end region of the second arterial sheath inner catheter may include an engagement region, such as a protrusion, which may be a ring, bump, etc., extending slightly proud of the outer surface of the distal end region (proximal to the distal end) of the second arterial sheath inner catheter that may releasably engage with an inner region at the tip of the daughter catheter; in some cases the daughter catheter may include a recessed region near the distal tip of the daughter catheter to engage with this engagement region. Either or both the distal tip region of the daughter catheter and the engagement region of the second arterial sheath inner catheter (granddaughter catheter) may be formed of a low-durometer material that may compress and/or stretch to engage and form a temporary seal when engaged. The granddaughter catheter may also include a proximal hub and/or handle 2565 that may include an in-line passage connecting to a lumen (e.g., for passing guidewire 2554) and a connection to an inflation fluid to inflate/deflate the balloon at the distal end.

In FIG. 24 the apparatus is shown with a guidewire 2554 (such as, but not limited to, a 0.035" guidewire).

Figures 25, 26:
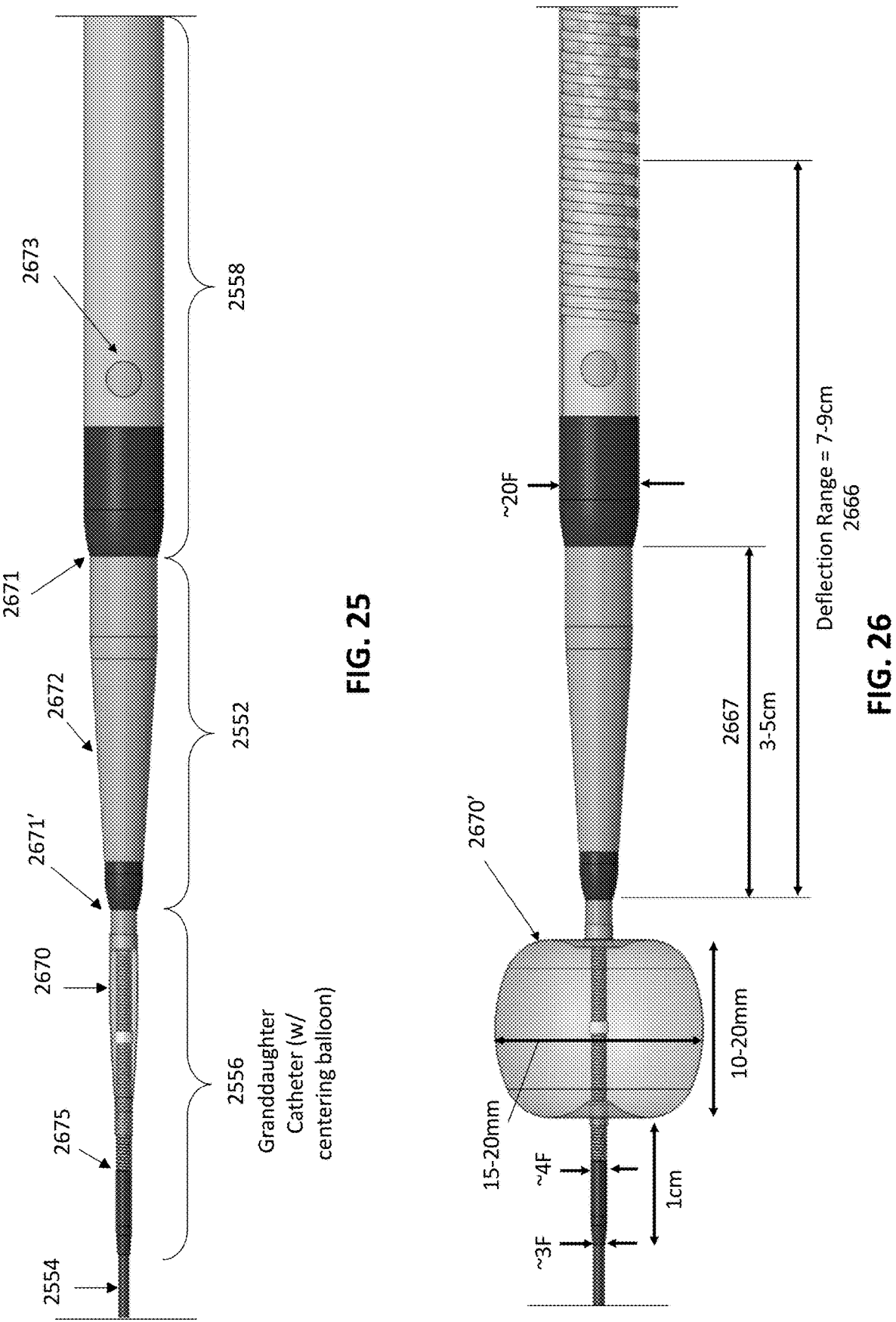
FIGS. 25 and 26 illustrate an example of a distal end region the system shown in FIG. 24, including an arterial sheath (mother catheter), a first inner catheter (daughter catheter with a steering/deflection region), and a second inner catheter (granddaughter with an expander, shown as a balloon).

FIGS. 25-26 illustrate one example of a distal end region an apparatus such as that shown in FIG. 24 in greater detail. FIG. 25 shows the distal end region of the apparatus of FIG. 24 with the distal balloon 2670 (deflection balloon) on the distal end region of the granddaughter 2556 uninflated; FIG. 26 show the same apparatus with the balloon 2670' inflated. In FIG. 26 the distal end region of the mother catheter 2558 is also shown as partially transparent. The mother catheter includes one or more (e.g. a plurality of) infusion side holes 2673 for infusion of arterial blood. As mentioned above, the distal end of the mother catheter is configured to releasably engage with the distal end region of the daughter catheter 2552. The distal end region of the daughter catheter may include a deflection region 2666 that is configured to bend as it is actuated by a proximal control (e.g., on a proximal handle). In FIG. 26 an example of a deflection range of between 7-9 cm is shown or illustration only; the daughter catheter may have deflection range that is greater or smaller than 2-9 cm (e.g., 1-10 cm, 1-5 cm, 2-8 cm, 1-8 cm, 3-7 cm, 3-10 cm, etc.).

When the mother catheter is releasably coupled at its distal end to the outer diameter of the daughter catheter, as shown in FIGS. 25-26, at least a portion of the distal end region 2667 of the daughter catheter may extend distal to the distal end of the mother catheter. In FIG. 26 an example of this distance is shown to be between about 3-5 cm (e.g., between 1-10 cm, between 2-8 cm, between 3-6 cm, between 3-10 cm, between 3-8 cm, etc.). the distal end region of the mother catheter may be configured to provide a seamless transition 2671 when engaged with the distal end region of the daughter catheter. In FIGS. 25-26 at least part of this distal end region of the daughter catheter 2552 may be configured to deflect, as mentioned above, and may be tapered over at least a portion of its length 2672. For example, the distal end region of the mother catheter may be tapered, and/or may be formed of a low-durometer material. The distal end the daughter catheter may also be configured to form a seamless transition 2671' when releasably engaging with the distal end region of the granddaughter 2556, in some cases just proximal to the expandable balloon 2670. The expandable balloon may also be referred to as a deflection balloon, which may be configured to assist in crossing the heart valve, as will be described in greater detail below. FIG. 26 illustrates an example of the balloon 2670' in an inflated configuration showing exemplary dimensions, e.g., between about 15-20 mm in diameter, such as between about 10-30 mm, between about 15-25 mm, between about 15-20 mm, etc., and/or between about 5-30 mm long (e.g., between about 5-35 mm long, between 10-35 mm long, and/or between about 10-20 mm long, etc.).

In general, the dimensions shown in any of these figures, including FIGS. 25-26 are for illustrative purposes only, and may be varied (e.g., +/−1%, 2%, 5%, 10%, 15%, 20%, 30%, 40%, 50%, 75%, 100%, etc.), unless the context indicates otherwise. In FIG. 26 the distal end region of the granddaughter catheter may have an outer diameter of about 4 F while the distal tip region may be, e.g., 3 F. In general, the distal end region of the granddaughter catheter may be configured as a microcatheter distal tip having a low crossing profile 2675. This low-crossing-profile tip may be highly flexible (and may include one or more coils, as shown in FIG. 25-26).

The apparatus is also shown over a guidewire 2554, e.g., a 0.035" guidewire.

Figures 27A, 27B:
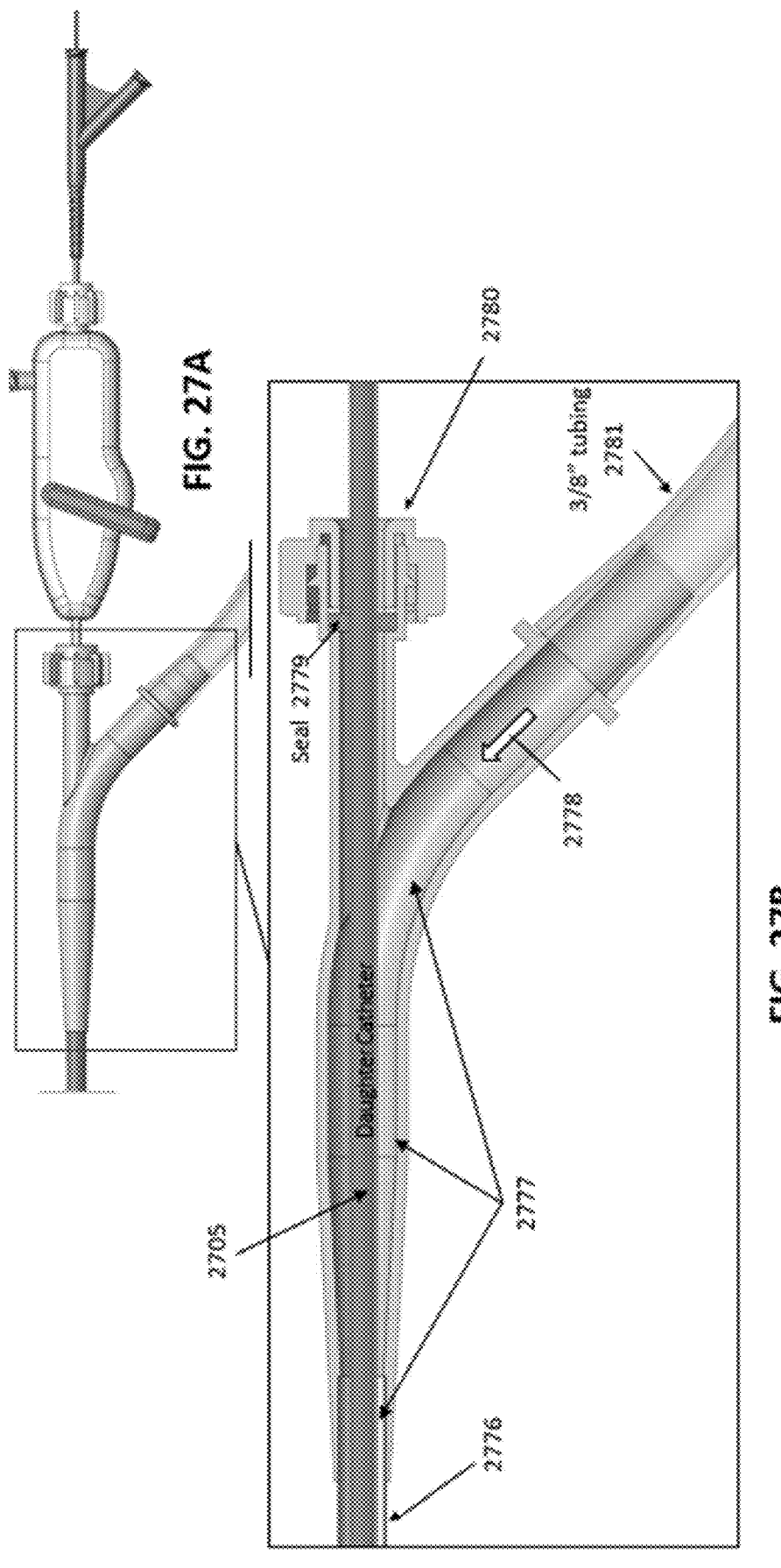
FIGS. 27A and 27B illustrate one example of a proximal end of the system of FIG. 24 (arterial sheath set) including approximal region of an arterial sheath (mother catheter), receiving the first inner catheter (daughter catheter) and the second inner catheter (granddaughter catheter).

FIGS. 27A and 27B illustrate a proximal end region of the mother catheter, daughter catheter and granddaughter catheter (FIG. 27A). FIG. 27B shows details of the proximal hub of the mother catheter similar to that shown in FIG. 24. In this example the proximal hub of the mother catheter includes a central lumen 2777 for passing arterial blood (e.g., from the tubing 2781) to be released into the vasculature from the distal end region of the mother catheter in the distal direction 2778. The arterial blood lumen 2777 is fluidly continuous with the shaft 2776 of the arterial sheath. This lumen is in fluid communication with an in-line seal 2779, e.g., within a hemostasis valve 2780 at the proximal end of the hub. In this example the hemostasis valve is configured as a rotating hemostasis valve, which is shown closed over the daughter catheter 2705.

Figures 28A, 28B:
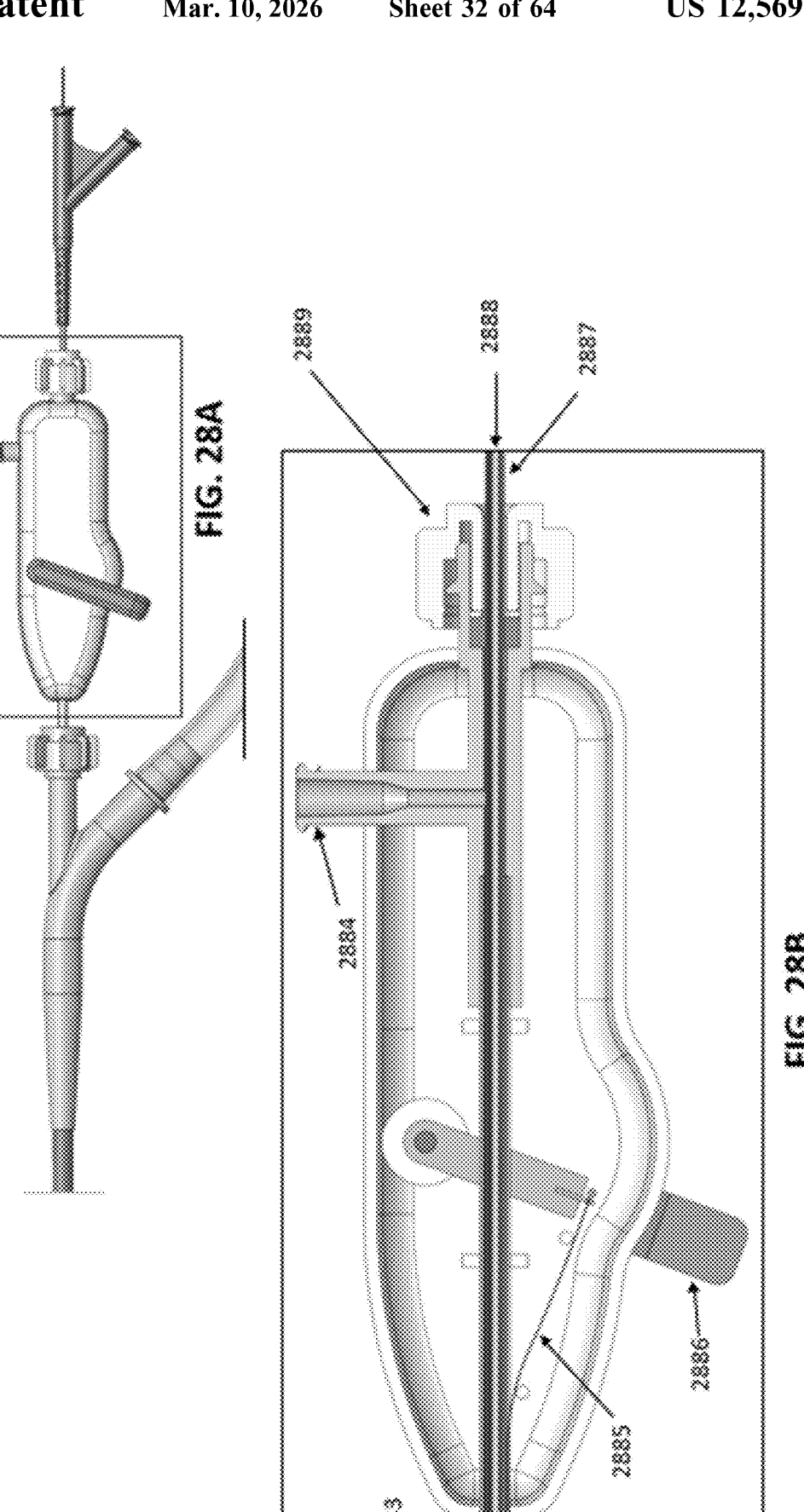
FIG. 28A is similar to FIG. 27A, highlighting the proximal end of the first inner catheter (a first daughter catheter).
FIG. 28B shows a section through the proximal end of the first inner catheter of FIG. 28A.

FIG. 28A is similar to FIG. 27A, showing the proximal end region of the mother catheter, daughter catheter and granddaughter catheter. FIG. 28B shows an enlarged detail on the proximal handle of the daughter catheter. In this example the proximal handle includes a control 2886 (e.g., lever, button, slider, etc.) to control bending of the distal end region of the daughter catheter. The control may apply tension to a pull wire (e.g., a deflection pull wire 2885) coupling the control to the deflection region of the distal end region of the daughter catheter, which is described in greater detail below. The handle may be coupled to the daughter catheter shaft 2883 and may include one or more ports 2884, such as a flush port (shown in this example as a luer port). The proximal handle of the daughter catheter may also include a hemostasis valve 2889 (e.g., a rotating hemostasis valve) to allow passage of the granddaughter catheter 2887 and/or guidewire e.g., through a guidewire lumen 2888 within the granddaughter catheter 2887 or a lumen of the daughter catheter.

Figures 29A, 29B, 29C:
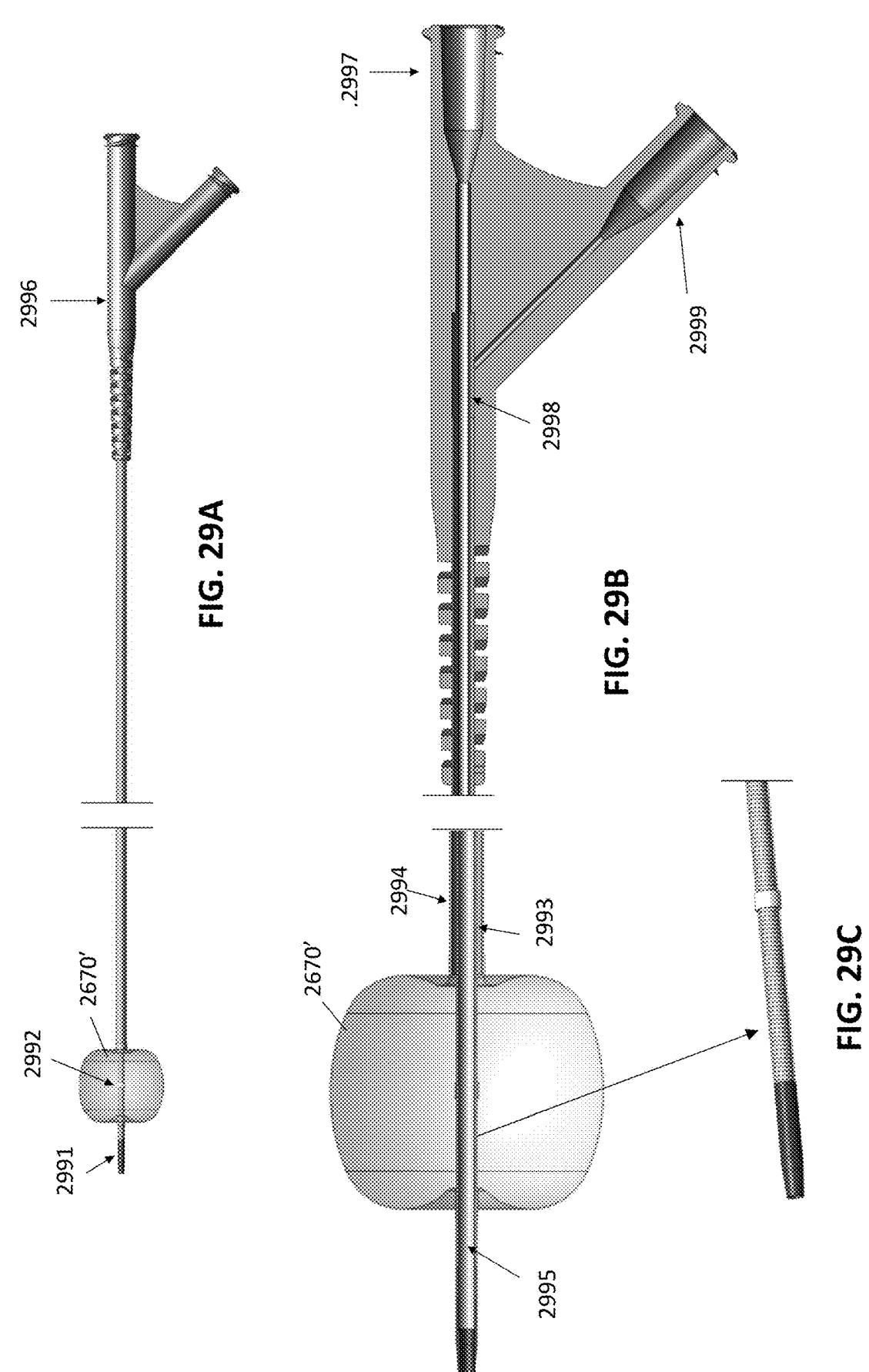
FIGS. 29A and 29B show a second inner catheter (granddaughter catheter).
FIG. 29C shows an enlarged view of the distal tip region of the second inner catheter of FIG. 29A.

FIGS. 29A-29C illustrate one example of a granddaughter catheter (e.g., second inner catheter) described herein. In general the granddaughter may be highly flexible along its length and may include a distal tip that is formed of a low-durometer material; in some cases the distal tip may be radiopaque (RO), such as a Tungsten-loaded Pebax 2991. In some cases the distal expandable member (e.g., balloon 2670') may also include one or more radiopaque markings, such as a RO marker band 2992.

The proximal end of the granddaughter catheter may include a hub or handle 2996 and may include an inflation port 2999 in fluid communication with an inflation lumen 2998 to expand the balloon and/or collapse the ballon 2670'. The granddaughter catheter may include an outer shaft 2994 that is flexible and that encloses an inflation lumen 2993 in fluid communication with the expandable member (balloon 2670') and the inflation port 2999. The outer shaft 2994 may also enclose a guidewire lumen 2995 that may be lubricous and may include a proximal port or opening 2997 (for example, the guidewire lumen may include a lubricious layer or coating, such as a PTFE layer, coating, etc.). FIG. 29C shows detail on the inner shaft of the distal end region of the granddaughter catheter, which may optionally include coils and/or a reinforcement braid. The distal tip of any of these catheters may be soft (e.g., low durometer, such as less than 70 Shore A, less than 60 Shore A, less than 55 Shore A, less than 50 Shore A, less than 45 Shore A, less than 40 Shore A, less than 35 Shore A, etc.).

Figures 30A, 30B:
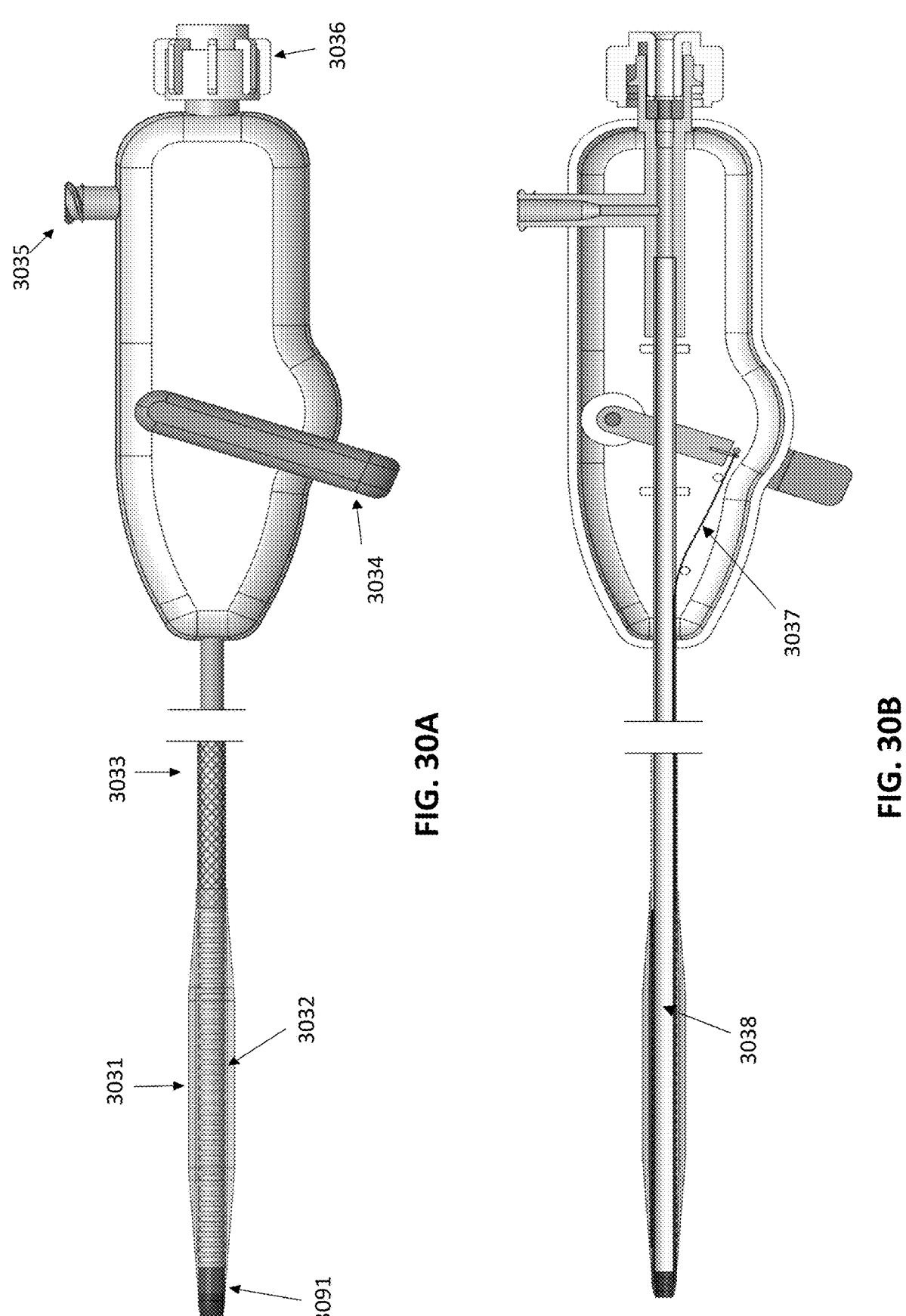
FIG. 30A shows a perspective view of the first inner catheter, including a deflecting/steerable distal region.
FIG. 30B shows a section through the first inner catheter of FIG. 30A.
Figures 38A, 38B, 38C:
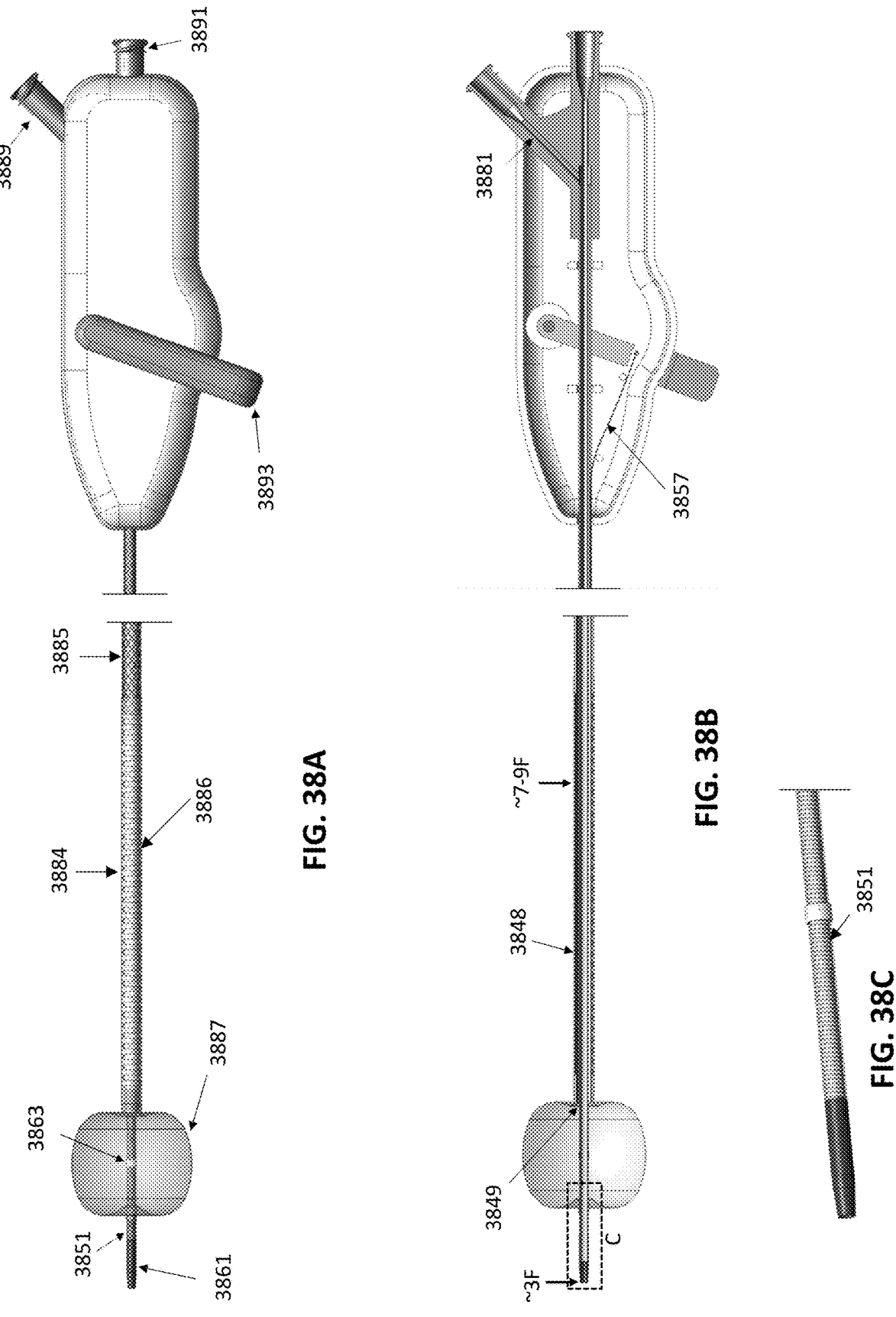
FIGS. 38A-38B show an example of an inner catheter (e.g., a granddaughter/daughter hybrid catheter) having both a distal expander and a steerable region in the distal end region (e.g., proximal to the expander) for an arterial sheath set as described herein.
FIG. 38C shows an enlarged view of the distal tip region of the inner catheter shown in FIG. 38A.

FIGS. 30A-30B illustrate an example of a daughter catheter (e.g., a first inner catheter) similar to that shown in FIGS. 24, 25-26 and 28A-28B. In FIG. 30A the steerable distal end of the daughter catheter is shown formed of a laser cut hypotube 3032 that is cut along one side to form a single plane of deflection. This hypotube is covered with a low-durometer flexible material 3031 and may be tapered distally and proximally, as shown in FIG. 30A. The distal end region 3091 may be formed of a radiopaque (RO) material, such as a Tungsten loaded PEBAX. The elongate shaft of the daughter catheter may be configured as a braided outer shaft 3033 providing proximal support, while allowing it to remain highly flexible. As shown in FIG. 38B, the proximal handle or hub may include a control 3034 (e.g., deflection lever); the control may apply or release tension on a deflection pull wire 3037 that may cause the distal end region to deflect. The handle may also include one or more ports, such as a hemostasis valve 3036 and a lumen flush port 3035. The lumen fluish port may be in fluid communication with the catheter lumen 3038. In some cases this lumen may be lubricious. For example, the catheter lumen may be formed of a PTFE that allows the granddaughter to slide freely through the lumen.

Figures 31A, 31B, 31C, 31D, 31E, 31F, 31G:
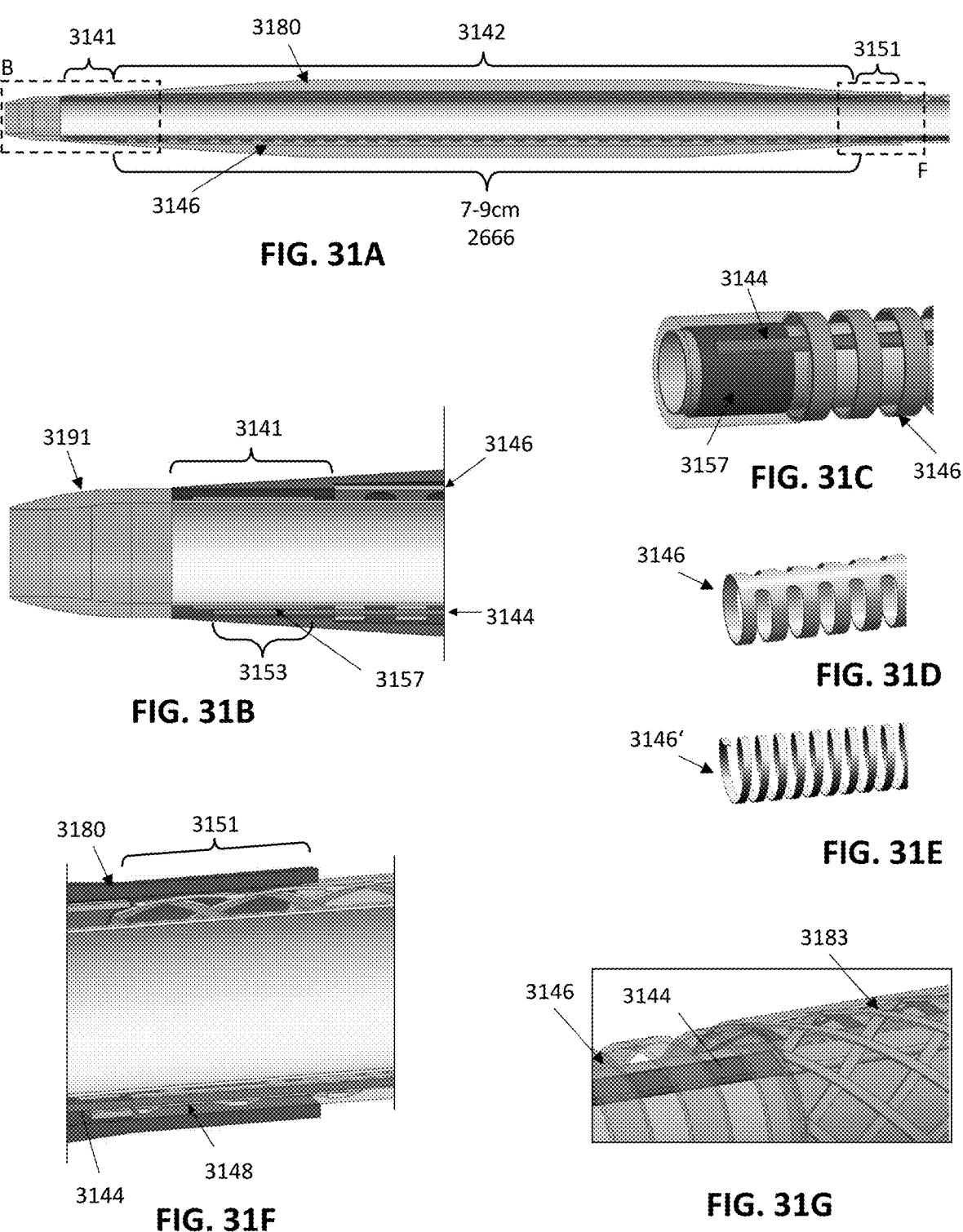
FIGS. 31A-31G illustrate details of regions of the first inner catheter shown in FIGS. 30A-30B.

FIGS. 31A-31G show details for the construction of one example of a daughter catheter. For example, FIG. 31A shows an enlarged view of a distal end region of the daughter catheter of FIGS. 30A-30B. In this example the deflection region 2666 is configured to have a length of the deflectable region of between about 5-15 cm (e.g., between 7-9 cm, between 5-10 cm, between 7-12 cm, etc.). The steering region 3142 in any of these catheters may be formed by a deflection element having a relatively high column strength so that it does not foreshorten when force is applied from the proximal end, e.g., by pulling a tendon (e.g., pull wire 3144) or lengthen when pushing, but will instead bend in a predictable bending plane. The deflection element may generally be a deflection spine. FIGS. 31D and 31E illustrate examples of deflection spine that may be used and included in the deflection region. In FIG. 31D the deflection spine 3146 is formed from a laser-cut metal hypotube (e.g., nickel titanium, stainless steel, etc.) having radial cut-out regions, e.g., semi-circular radial cut-out regions, arranged along one side, so that it preferentially bends in one direction. In FIG. 31E the deflection spine 3146' is a coil or spring. The deflection spine may be formed of metal or a polymeric material. Other deflection spines may be formed by pivotally connected segments.

As shown in FIG. 31A the deflection spine 3146 is shown in cross-section and extends along the length of the deflection region 2666 (e.g., between 7-9 cm in this example), outside of the central lumen formed by the (e.g., polymeric) tube of the elongate body. The deflection spine may be fused to the elongate body or may be attached at just the ends. The deflection region 2666 also includes a deflection jacket 3180 that covers the deflection region. In any of these apparatuses the deflection jacket may be attached just at the proximal and distal ends, as shown by boxed regions B and F (shown in greater detail in FIGS. 31B and 31F, respectively). The deflection jacket 3180 may be un-fused over most of the length of the deflection region, allowing the inner shaft to compress on one side as the deflection region 2666 is bent by pulling on the pull wire 3144. The ends of the deflection region (the distal end and proximal end regions) may be tapered.

For example, FIG. 31B shows the tapered distal region 3141 of the jacked at the distal end region of the daughter catheter. The tapered jacket is fused (bonded) over the distal soft tip 3191. The distal end of the pull wire 3144 (e.g., tendon) may be attached to one side of the distal end (or distal end region) of the deflection spine 3146 and secured in place; in FIGS. 31B and 31C the pull wire 3144 is secured to the deflection spine 3146 using a pull wire band 3157, but it may also or alternatively be bonded (e.g., welded, adhesively attached, etc.) to the deflection spine either directly or indirectly over a bonding region 3153. FIG. 31C shows a partial view of the distal end and the attachment of the pull wire 3144 to the pull wire band 3157. The pull wire may slide relative to the deflection spine 3146 and the rest of the catheter. In some examples the pull wire may run over or preferably under the deflection spine. The pull wire may be lubricous or may be within a lubricious channel 3148 that allows the pull wire to be freely actuated while remaining encapsulated in the shaft (e.g., the braided shaft) of the catheter. For example, FIGS. 31F and 31G show the pull wire 3144 extending proximally from the deflection region through the elongate body that includes a braided 3183 shaft. The proximal end of the deflection region includes a region over which the proximal end of the jacket 3180 is fused to the shaft of the catheter.

Figures 32A, 32B, 32C:
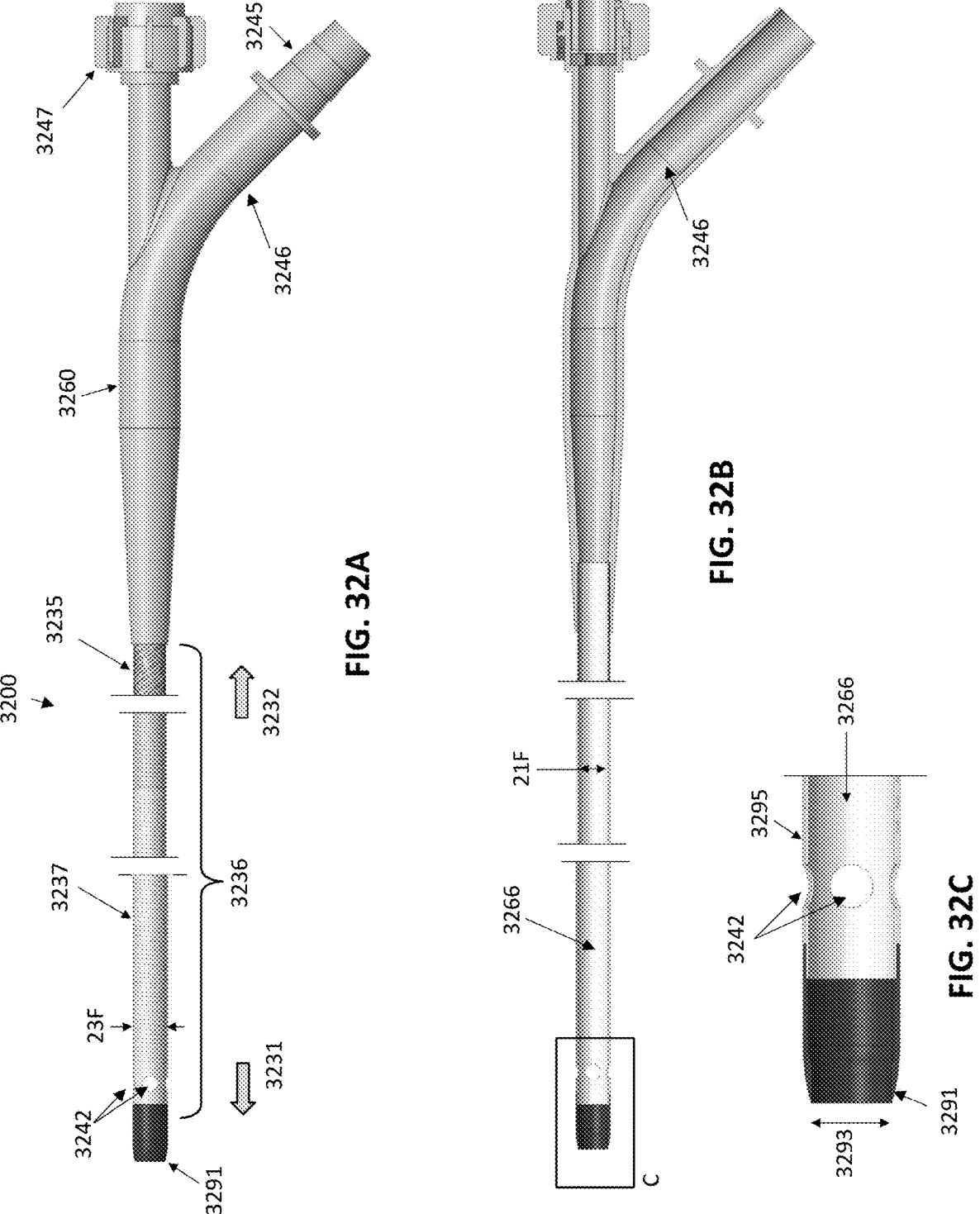
FIGS. 32A-32C illustrate an example of an arterial sheath (e.g., mother catheter) in a perspective view (FIG. 32A), sectional view (FIG. 32B) and an enlarged view of the distal tip region (FIG. 32C).

FIGS. 32A-32C illustrate another example of an arterial sheath (mother catheter) similar to that in FIG. 24 in greater detail. In this example the arterial sheath 3200 includes an elongate body 3239 having regions of different stiffness, decreasing from the proximal end 3231 to the distal end 3232. For example, the region closes to the proximal hub 3260 may be stiffer (e.g., more pushable) and the region 3231 closest to the distal end (distal tip 3291) may be softer and more trackable. The elongate body may be formed of a reinforced multi-durometer shaft 3236 In some cases the proximal region of the shaft may include a stiffer braid section 3235 and the more distal region 3237 may include a more flexible coil. The distal tip region may be formed of a radiopaque (RO) material, preferably a low-durometer RO material, such as tungsten loaded PEBAX.

The mother catheter may include lumen 3266 in fluid communication with side holes 3242 (outlets) the mother catheter for delivery of blood out of these distal infusion side holes 3242. The side hoes 3242 may be arranged radially around the distal end region. The outlets may be positioned proximal of the distal end (distal tip), e.g. between 1-10 cm (e.g., between 1-4 cm, between 1-2 cm, etc.). The proximal hub 3260 may include an off-axis connection line 3246 having a connection port 3245 (e.g., ⅜" hose barb) for connecting to the external ECMO device (not shown) so that blood may be passed through the elongate body and out of the outlets. In some cases blood may pass through the lumen around a daughter catheter (alternatively the daughter catheter(s) may be removed from the lumen). The proximal hub 3260 may also include a hemostasis valve 3247 as described above, to allow insertion and removal of one or more daughter catheter(s) and/or guidewires.

The mother catheter may be any appropriate length or diameter. In the example shown in FIGS. 32A-32B the mother catheter has an outer diameter (excluding the proximal hub) of 23 F and an inner diameter of about 21 F (thus is compatible with daughter catheters of 21 F or less). Other examples may have an outer diameter of between 18 F and 35 F and corresponding inner diameters (e.g., between about 16 F and 32 F). In any of these catheters the distal tip region may be narrower or may include a radially narrow region (e.g., for engaging over another catheter nested within the catheter). In the example shown in FIG. 32C (enlarged region C in FIG. 32) the distal tip 3291 opening 3293 narrows to about 20 F (an approximately 1 F reduction in inner diameter). The distal tip 3291 is fused to the outer jacket 3295 of the catheter. In some examples the lumen 3266 of the mouther catheter may include a lubricious coating or liner (e.g., a PTFE liner) to enhance sliding of catheters within the lumen. In some examples a lubricious liner may slide over the daughter catheter.

Figure 33:
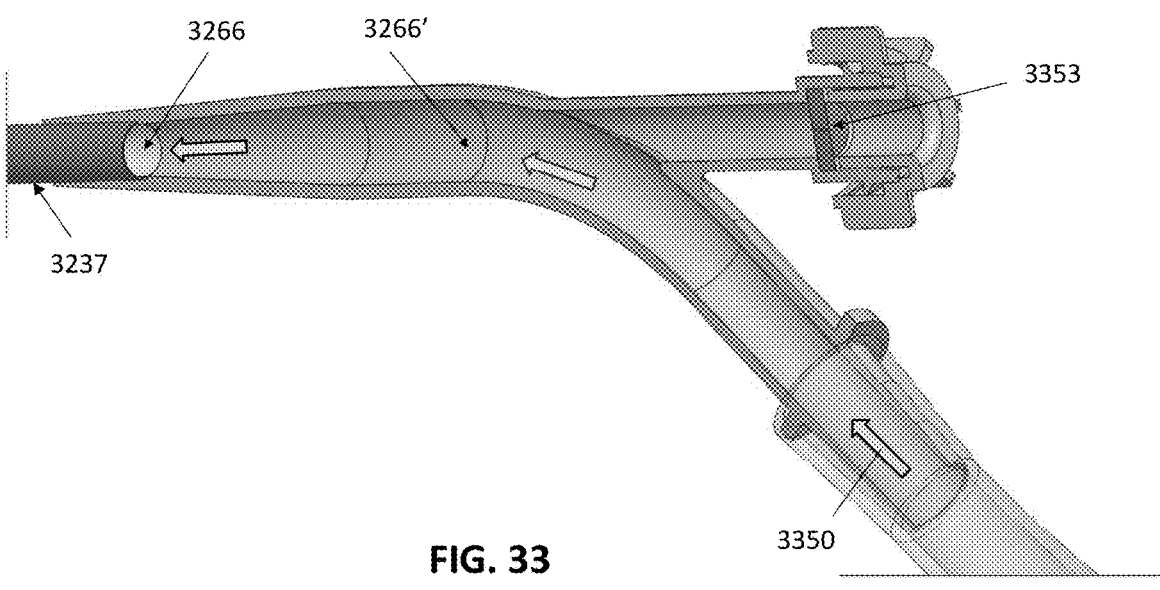
FIG. 33 illustrates one example of a proximal end region (e.g., handle) of an arterial sheath similar to that shown in FIGS. 32A-32C, configured to be a proximal end arterial hub.

FIG. 33 shows an enlarged view of the proximal end hub ("arterial hub") of the mother catheter shown in FIGS. 32A-32C, illustrating the flow path 3350 taken by blood from the ECMO oxygenator. The blood flows from the lumen 3266' of the hub to the lumen of the catheter 3266 along the shaft 3237 of the arterial sheath (mother catheter). In FIG. 33 The hemostasis valve is sealed (e.g., by a closed seal 3353), as no daughter catheter is passing through the mother catheter. Thus blood may flow laterally out of the outlet and/or out of the distal end (not shown in FIG. 33) of the mother catheter.

Figure 34A:
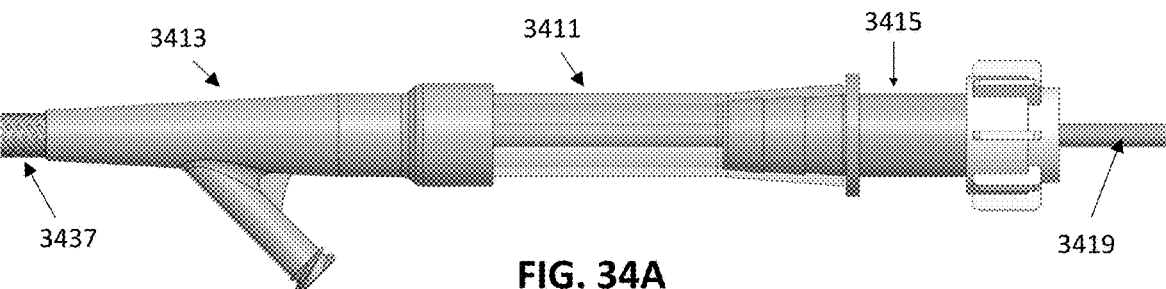
FIGS. 34A-34C illustrate one example of a cannula hub for an arterial sheath configured to allow connection to an ECMO apparatus (e.g., pump).
Figure 34B:
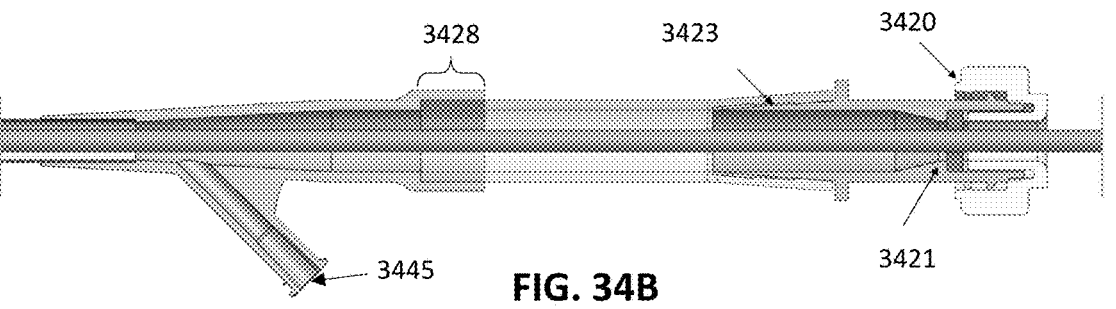

FIGS. 34A-34B illustrate an example of a two-piece arterial sheath hub that may be used with any of these apparatuses. In FIGS. 34A-34B the hub shown may include flexible tubing 3411 (e.g., TYGON tubing) coupled (e.g., bonded 3428) between the proximal hub (Y-arm hub) 3413 that is coupled to the elongate shaft of the mother catheter 3437 on the distal end and to a proximal connector (e.g., removably connector) 3415 on the proximal end including (or coupled to) a hemostasis valve. In this example a granddaughter catheter 3419 is inserted through the hemostasis valve 3420 (e.g., rotating hemostasis valve) so that a seal 3421 within the valve is close (locked) around the granddaughter catheter. The hub 3413 may also include a port 3445 (e.g. for connecting to the ECMO device, as mentioned above, or for acting as a flush port. The flexible tubing 3411 may be coupled to the removably connector 3415 by a hose barb 2423 or other coupling means.

Figure 34C:
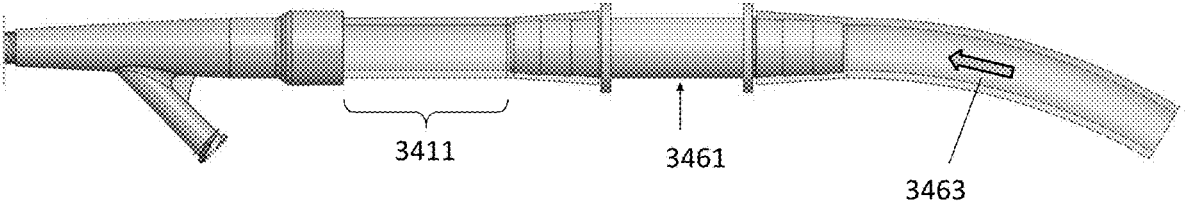

In some examples the proximal end of the mother catheter may be modified after delivery to the target vessel. For example, the proximal end of the mother catheter may include the proximal end shown in FIGS. 33A-33B for positioning the mother catheter, allowing flushing through the flushing port 3445 and passage of one or more daughter catheters through the hemostasis valve. Once positioned, the proximal end may be converted for coupling to the ECMO apparatus, as shown in FIG. 34C. In FIG. 34C the proximal connector shown (with the hemostasis valve) can be removed while the flexible tubing 3411 is clamped shut (to maintain hemostasis) and swapped with a double hose connector 3461 that connects via connectors (e.g., barb connectors) to an ECMO oxygenator to receive oxygenated blood 3463.

In some cases the apparatuses described herein may include a combined daughter/granddaughter. For example the "daughter" (inner catheter) to be used with the mother (arterial sheath) may be configured to include both a steerable distal end region and a deflection region (e.g., balloon). FIGS. 38A-38C illustrate an example of a daughter catheter (in some cases referred to as a granddaughter catheter) that may be used with any of the arterial sheath sets. In some cases the arterial sheath set may include a daughter (granddaughter) catheter having both deflection of the tip region and the expander (balloon) in place of a set of separate deflectors and balloon, or in some cases either the daughter (deflector) catheter or the granddaughter (expander) may be configured to include both steering and an expander.

In the example of the daughter catheter (or granddaughter catheter) shown in FIGS. 38A-38C the catheter may include a proximal handle with a deflection control (e.g., deflection lever 3893) and one or more ports, including an inflation port 3889 (e.g., balloon inflation port) as well as a guidewire port 3891. The distal end region includes a soft distal tip 3861 (e.g., a radiopaque distal tip), a distal expander 3887 (e.g., expandable balloon, basket etc., shown as a balloon in FIGS. 38A-38B), and a steerable distal end region 3684 that is proximal to the balloon and tip. The deflection region may be configured as described above in reference to FIGS. 31A to 31G. For example, the deflection region may include a deflection spine 3886, that in some examples may be formed of a laser-cut hypotube, coil, etc.) and may be covered by a low durometer deflection jacket. The elongate length of the outer shaft 3884 may be stiffer proximally than distally and may include one or more braids 3885 (e.g., braided outer shafts) to enhance pushability and tracking. The distal expander may include a maker 3863 (e.g., a radiopaque marker). The distal end region 3851 may be reinforced with a coil/braid within the inner shaft instead of a braided outer shaft 3885.

The cross-section view shown in FIG. 38B shows the inflation lumen and outlet 3849 into the balloon in fluid communication with the balloon inflation lumen 3881. A pull wire 3857 is connects the control 3893 on the proximal handle to the deflection region 3884 as described above. In any of these daughter/granddaughter catheters the outer diameter may be relatively small to enhance flexibility and navigation. In the example shown the outer diameter is between about 7-9 F and the distal tip narrows to about 3 F. FIG. 38C shows an enhanced view of region C at the distal end region of the catheter, showing the distal end region with the outer sleeve 3848 removed, showing optional coil/braid reinforcements 3581 allowing flexibility (tracking) while maintaining the column strength for pushabilty.

Figures 39A, 39B, 39C, 39D, 39E, 39F, 39G:
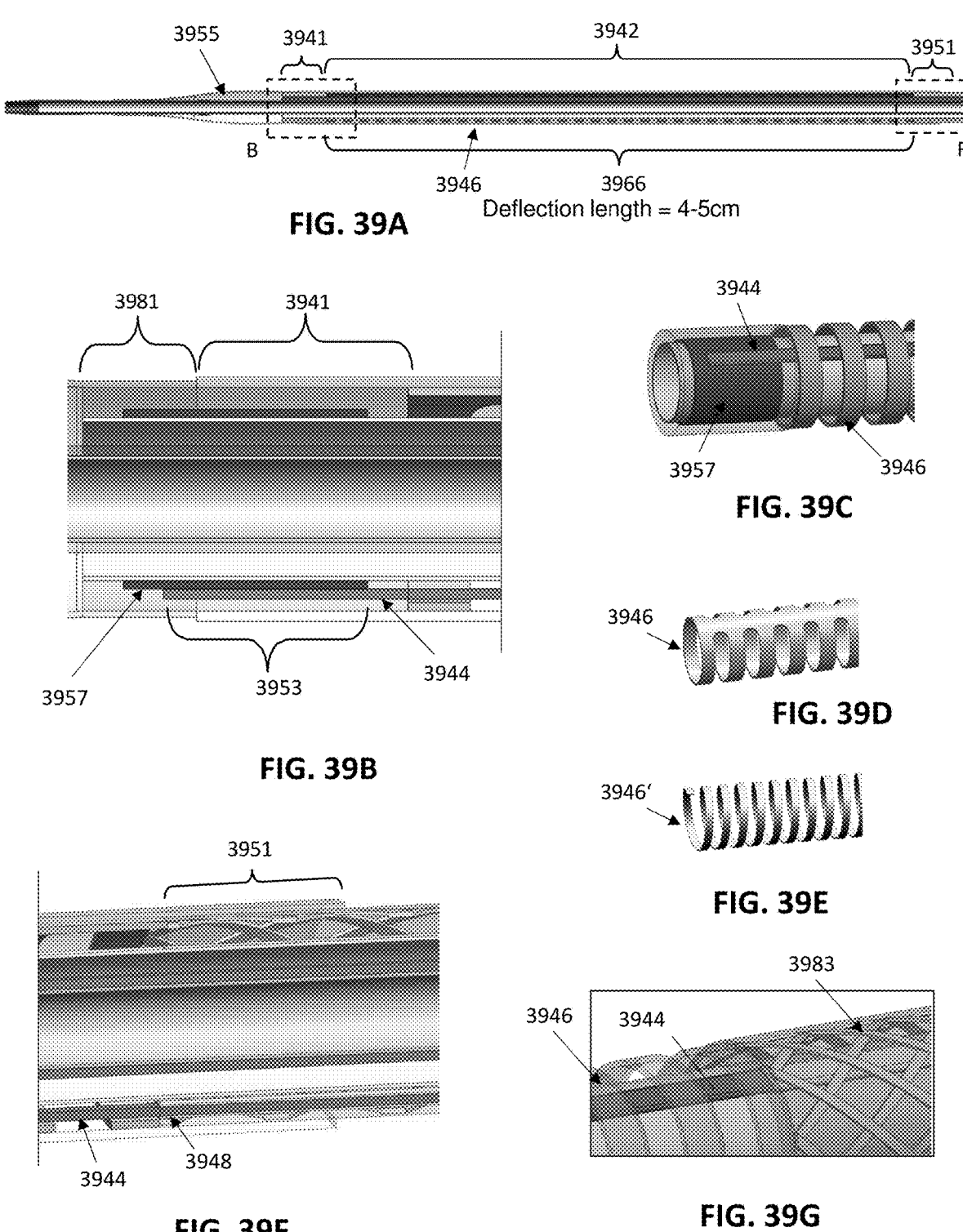
FIGS. 39A-39G illustrate details of regions of the inner catheter shown in FIGS. 38A-38B.

FIGS. 39A-39G show additional detail of the daughter catheter having both an expander (balloon) and deflection (steering) region shown in FIGS. 38A-38C. The exemplary construction details are similar to those shown in FIGS. 31A-31G. For example, FIGS. 39A-39G show details for the construction of one example of a daughter catheter having both an expander (e.g., balloon) and a steerable region. For example, FIG. 39A shows an enlarged view of a distal end region of the daughter catheter of FIGS. 38A-38C. In this example the deflection region 3966 is configured to have a length of the deflectable region of between about 3-10 cm (e.g., between 3-8 cm, between 3-6 cm, between 4-5 cm, etc.). The steering region 3942 in any of these catheters may be formed by a deflection element having a relatively high column strength so that it does not foreshorten when force is applied from the proximal end, e.g., by pulling a tendon (e.g., pull wire 3144) or lengthen when pushing, but will instead bend in a predictable direction. The deflection element may generally be a deflection spine. FIGS. 39D and 39E illustrate examples of deflection spine that may be used and included in the deflection region. In FIG. 39D the deflection spine 3946 is formed from a laser-cut metal hypotube (e.g., nickel titanium, stainless steel, etc.) having radial cut-out regions, e.g., semi-circular radial cut-out regions, arranged along one side, so that it preferentially bends in one direction. In FIG. 39E the deflection spine

3946' is a coil or spring. The deflection spine may be formed of metal or a polymeric material. Other deflection spines may be formed by pivotally connected segments.

As shown in FIG. 39A the deflection spine 3946 is shown in cross-section and extends along the length of the deflection region 3966, outside of the central lumen formed by the (e.g., polymeric) tube of the elongate body. The deflection spine may be fused to the elongate body or may be attached at just the ends. The deflection region 3966 also includes a deflection jacket that covers the deflection region. The distal balloon 3955 (shown collapsed in FIG. 39A) is attached to the elongate body, including attached at a balloon fusion region 3981 shown in FIG. 39B. In any of these apparatuses the deflection jacket may be attached just at the proximal and distal ends, as shown by boxed regions B and F (shown in greater detail in FIGS. 39B and 39F, respectively). The deflection jacket may be un-fused over most of the length of the deflection region, allowing the inner shaft to compress on one side as the deflection region 3966 is bent by pulling on the pull wire 3944. The ends of the deflection region (the distal end and proximal end regions) may be tapered.

For example, FIG. 39B shows the tapered distal region 3941 of the jacketed deflection region is shown at the distal end region of the daughter catheter. The tapered jacket is fused (bonded) over the distal soft tip 3991. The distal end of the pull wire 3944 (e.g., tendon) may be attached to one side of the distal end (or distal end region) of the deflection spine 3946 and secured in place; in FIGS. 39B and 39C the pull wire 3944 is secured to the deflection spine 3946 using a pull wire band 3957, but it may also or alternatively be bonded (e.g., welded, adhesively attached, etc.) to the deflection spine either directly or indirectly over a bonding region 3953. FIG. 39C shows a partial view of the distal end and the attachment of the pull wire 3944 to the pull wire band 3957. The pull wire may slide relative to the deflection spine 3946 and the rest of the catheter. In some examples the pull wire may run over or preferably under the deflection spine. The pull wire may be lubricous or may be within a lubricious channel 3948 that allows the pull wire to be freely actuated while remaining encapsulated in the shaft (e.g., the braided shaft) of the catheter. For example, FIGS. 39F and 389G show the pull wire 3944 extending proximally from the deflection region through the elongate body that includes a braided 3983 shaft. The proximal end of the deflection region includes a region over which the proximal end of the jacket 3980 is fused to the shaft of the catheter.

Figures 40A, 40B, 40C:
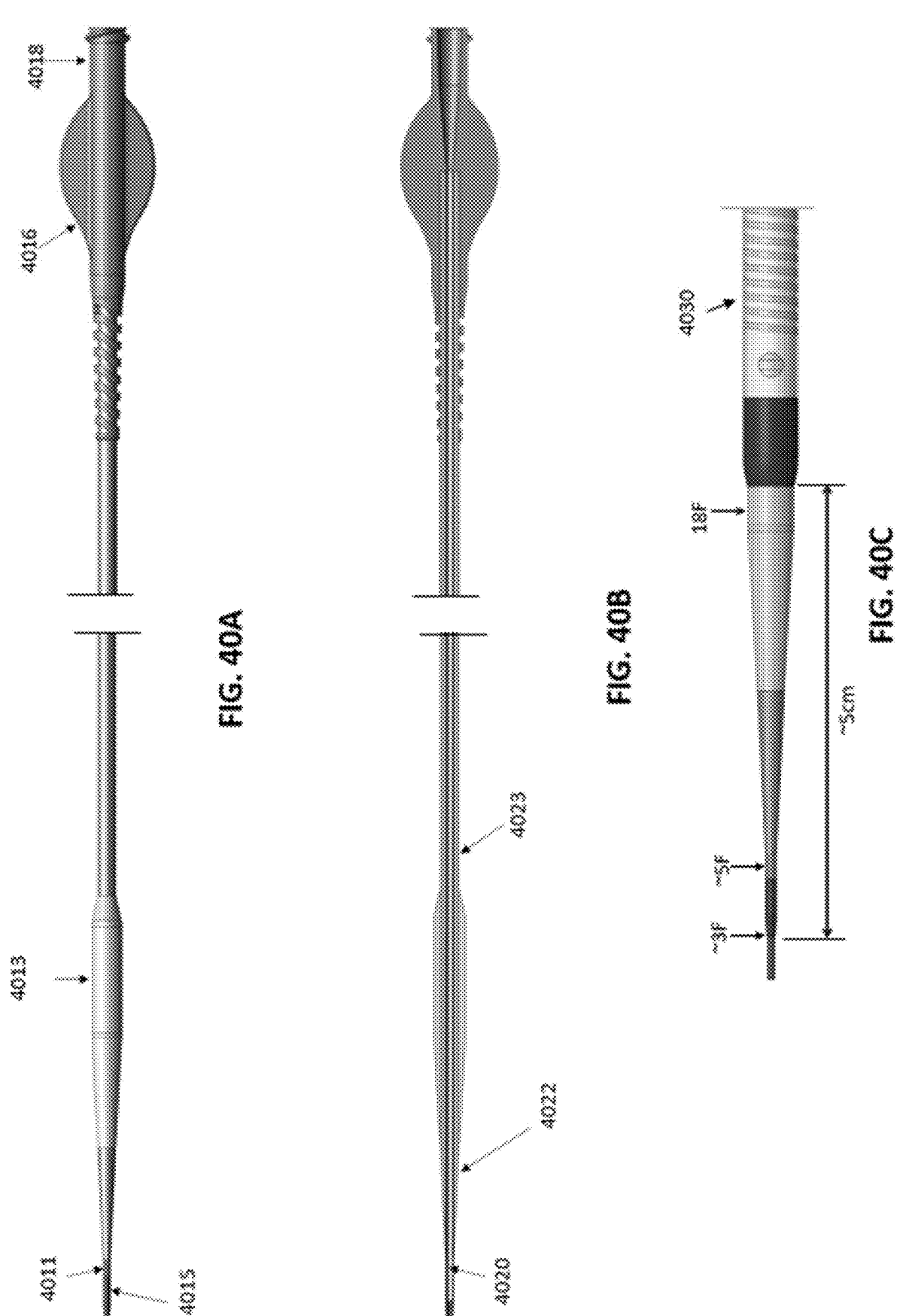
FIG. 40A-40C shows an example of a septal dilator daughter catheter for an arterial catheter (e.g., which may be part of an arterial sheath set) as described herein.

Also described herein are daughter catheters that are configured a septal dilators, which may be used to cross a perforated septum and deliver the apparatus to the left atrium (LA). For example, FIGS. 40A-40C illustrate one example of a septal dilator that are configured to engage with a mother catheter. In FIG. 40A the distal end region of the septal dilator daughter catheter 4000 includes a distal tip region 4015 that is radiopaque as described above, and a more proximal region of the distal end that is tapered up to a plateau region of daughter catheter that is configure to engage with a distal end of the mother catheter, as shown in FIG. 40C. in this example, the mother catheter 4030 forming an arterial sheath ("mother catheter") has a slightly narrower distal tip region that engage with the plateau region of the tapered element 4033. The proximal end of this plateau region 2123 may be tapered up to the plateau region until it reaches the desired thickness. The distal-facing side 4022 is more gradually tapered, as shown in FIGS. 40A-40C. For example, the catheter shaft may taper down distally. This may provide a low crossing profile. The daughter catheter may also include a coil/braid reinforced distal end region

4011 that may help improve tracking and pushability. The plateau region may be formed of a low-durometer (e.g., <80 Shore A, less than 70 Shore A, less than 65 Shore A, less than 60 Shore A, less than 55 Shore A, less than 50 Shore A, less than 45 Shore A, less than 40 Shore A, less than 35 Shore A, etc.).

The proximal end of the septal dilator daughter catheter shown in FIGS. 40A-40C may be configured to include a hub 4016 and may include one or more ports, including an inflation/expansion port 4018 for applying fluid to expand the expandable member (e.g., balloon) to expand the balloon, e.g., when crossing or preparing to cross the septum. The apparatus may include a guidewire lumen 4020 extending longitudinally through it. In addition, these apparatuses may be any appropriate length and/or diameter (inner and/or outer diameter). In FIGS. 40A-40C the apparatus is shown with exemplary dimensions; these dimensions are not limiting and the actual lengths and diameters may be larger or smaller. For example, the portion of the septal dilator daughter catheter extending beyond the distal end of the mother may be, e.g., between 1-10 cm (e.g., approximately 5 cm, shown in FIG. 40C). The radial diameter of the plateau region engaging with the distal end of the mother 40113 be approximately the same as the narrowing at the distal end of the tip of the mother catheter (e.g., 18 F) while the regions mor distally may match the diameter of the guidewire (e.g., 3 F) such as about 5 F.

Similarly, FIGS. 41A-41C illustrate another example of a tapered dilator daughter catheter that may act as a rail for a mother catheter (e.g., arterial sheath). For example, FIGS. 41A-41B show side and sectional views, respectively, of a variation of a daughter catheter that may be part of an arterial sheath set that tapers continuously over a long (e.g., 15 cm or longer, 17.5 cm or longer, 20 cm or longer, 25 cm or longer, 30 cm or longer, etc.) distal end region 4166 adjacent to a region of continuous outer diameter 4167. The constant OD region may provide pushability and kink resistance. The catheter OD/wall may taper down distally to provide low crossing profile and high flexibility to navigate heart valves. The taper may change by between about 0.001 mm diameter per mm length and 0.03 mm diameter per mm length (e.g., between 0.005 mm diameter per mm length and 0.02 mm diameter per mm length, etc.). In the example shown in FIGS. 41A-41C the distal tip has an OD of approximately 3 F, while the distal end of the continuously tapered region has an OD of about 5 F (continuously tapered down from an OD of about 18 F at the more proximal region 4167 having a constant OD). The distal tip region 4161 may be soft and radiopaque and may be reinforced 4165, e.g. by a coil or braid within the inner shaft. The proximal end may include a hub 4168 with one or more ports, including a guidewire port 4169 that is in fluid communication with the guidewire lumen 4170 (which may include a lubricious lining, such as PTFE, or may be formed of a lubricious tubing).

As shown in FIG. 41C, an outer region of the tapered daughter catheter 4100 proximal to the tapered region 4166 may be configured to engage and seal with the distal tip of the arterial sheath (mother catheter) 4177 as described above.

Venous Sheath Sets

Figure 35:
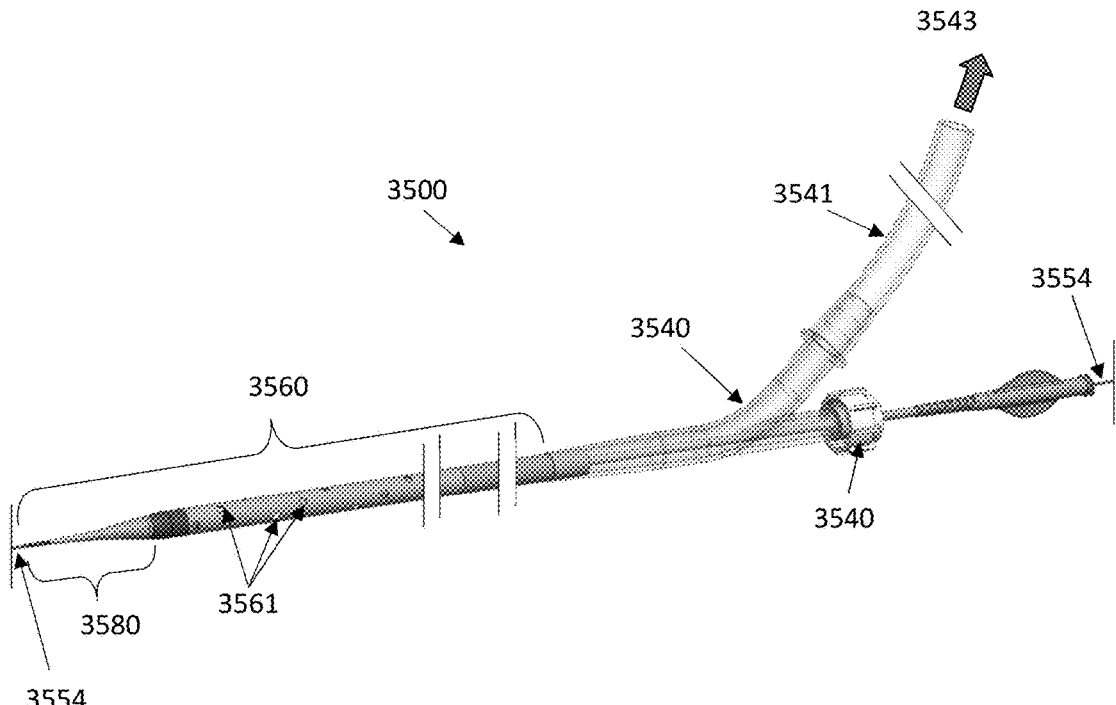
FIG. 35 illustrates one example of a venous sheath set that may be used as part of the apparatuses described herein.

Any of these apparatuses may include a venous sheath set including a venous sheath ("outer catheter") and optionally one or more venous inner catheters. Returning now to FIG. 35, this figure shows an example of a venous sheath that may be used with any of these apparatuses. In this example the venous sheath 3500 includes an elongate shaft (venous shaft) 3560 including a plurality of inlets (openings 3561) for withdrawing blood into the lumen of the outer catheter to pump (venous inflow 3543) via the ECMO pump. The venous sheath shown in FIG. 35 also includes a proximal hub 3540 (venous sheath hub) that includes connectors to connect to the tubing 3541 to the ECMO device and an in-line connector connecting to a hemostasis valve through which an arterial sheath set may be inserted and/or through which one or more venous inner catheters may be inserted. In FIG. 35 a venous sheath inner catheter 3580 and a guidewire 3554 is shown extending through the venous sheath 3500.

Figures 36A, 36B, 36C:
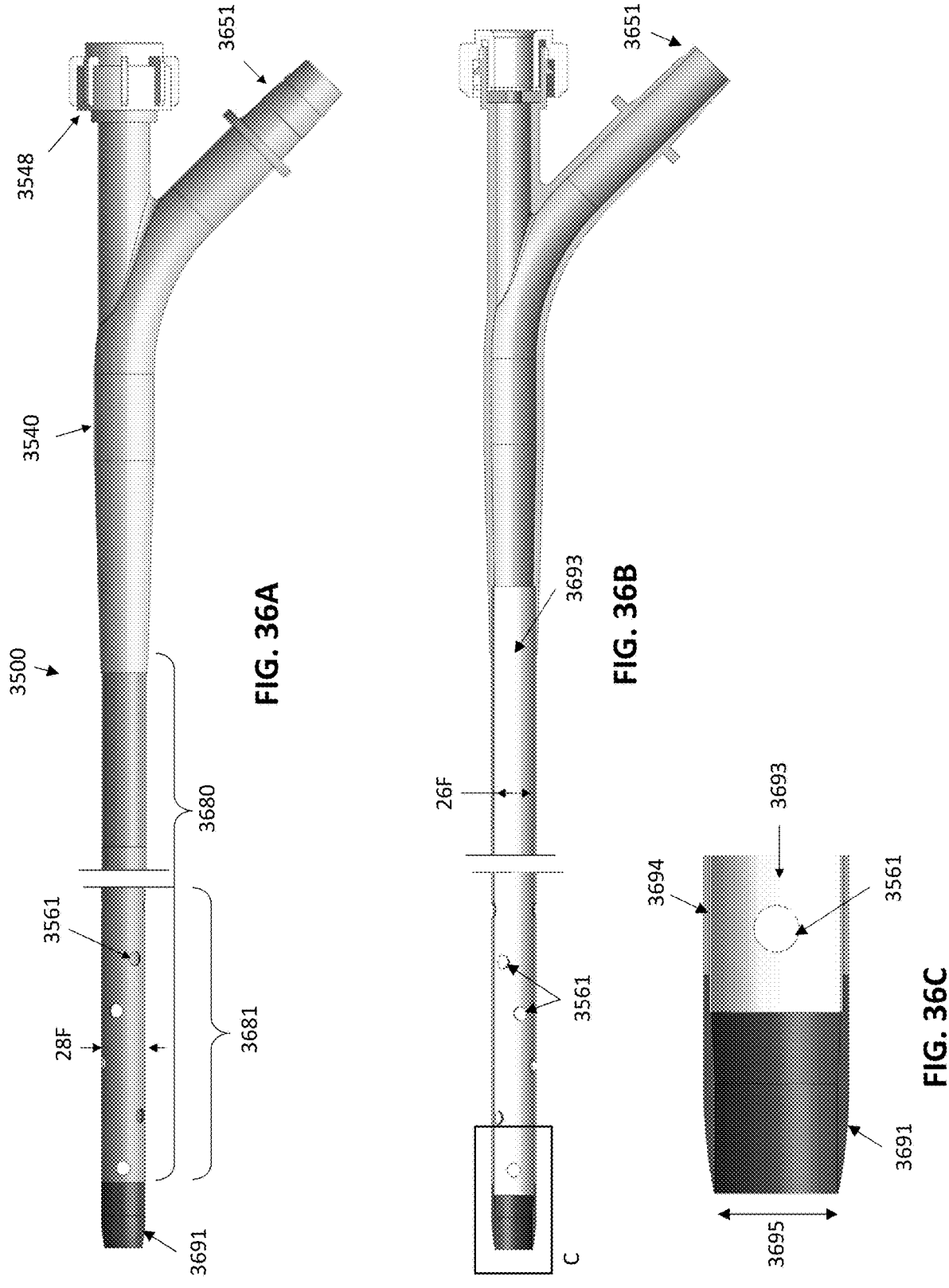
FIGS. 36A-36C illustrate an example of a venous sheaths, similar to that shown in FIG. 35.

FIGS. 36A-36C show additional detail for an example of an outer venous sheath similar to that shown in FIG. 35. In FIG. 36A the venous sheath 3500 includes a soft distal tip 3691 that may be radiopaque, similar to the tips of the arterial sheath set. The distal tip may also be adapted to sealingly engage with an outer surface of an arterial sheath as described above, while still allowing the arterial sheath to advance and/or withdraw within the lumen of the venous sheath (and/or the venous sheath to advance/withdrawn over the arterial sheath). For example an outer surface (proximal to the distal end of the arterial sheath) may include an engagement region, such as a protrusion, which may be a ring, bump, etc., extending slightly proud of the outer surface of the distal end region of the arterial sheath that may releasably engage with an inner region at the tip of the venous sheath; in some cases the venous sheath may include a recessed region to engage with this engagement region. In general, the distal tip of the venous sheath may also taper and may have a narrower inner diameter 3695 (by about 1 F or more) than the inner diameter of the elongate shaft (shown in FIG. 36B as about 26 F). In FIG. 36A the outer diameter is shown as about 28 F. The venous sheath may be any appropriate inner (e.g., between about 18 F and 32 F) and outer (e.g., between 20 F and 34 F) diameters.

The distal end region 3681 of the elongate shaft 3680 may include the plurality of inlet openings 3561 distributed along the length and radially around the perimeter. This inlet region may be any appropriate length (e.g., between about 1 cm to about 15 cm, 1 cm to 12 cm, 1 cm to 10 cm, 1 cm to 8 cm, 1 cm to 7 cm, 1 cm to 6 cm, 1 cm to 5 cm, 1 cm to 4 cm, etc.). In general the length of the flexible elongate body 3680 may be reinforced, and may be stiffer proximally (closer to the proximal hub 3540) than distally, so that it is more trackable at the distal end region. The proximal hub may include a hemostasis valve 3548 and a connector 3651 (e.g., barbed connector) to connect to the tubing linking the lumen 3693 of the venous sheath to the ECMO device. The inlets may pass through the wall of the elongate shaft, including through an outer jacket 3694.

Any of the apparatuses described herein may also include an outer sheath for inserting the venous sheath into the body (not shown).

Figures 37A, 37B:
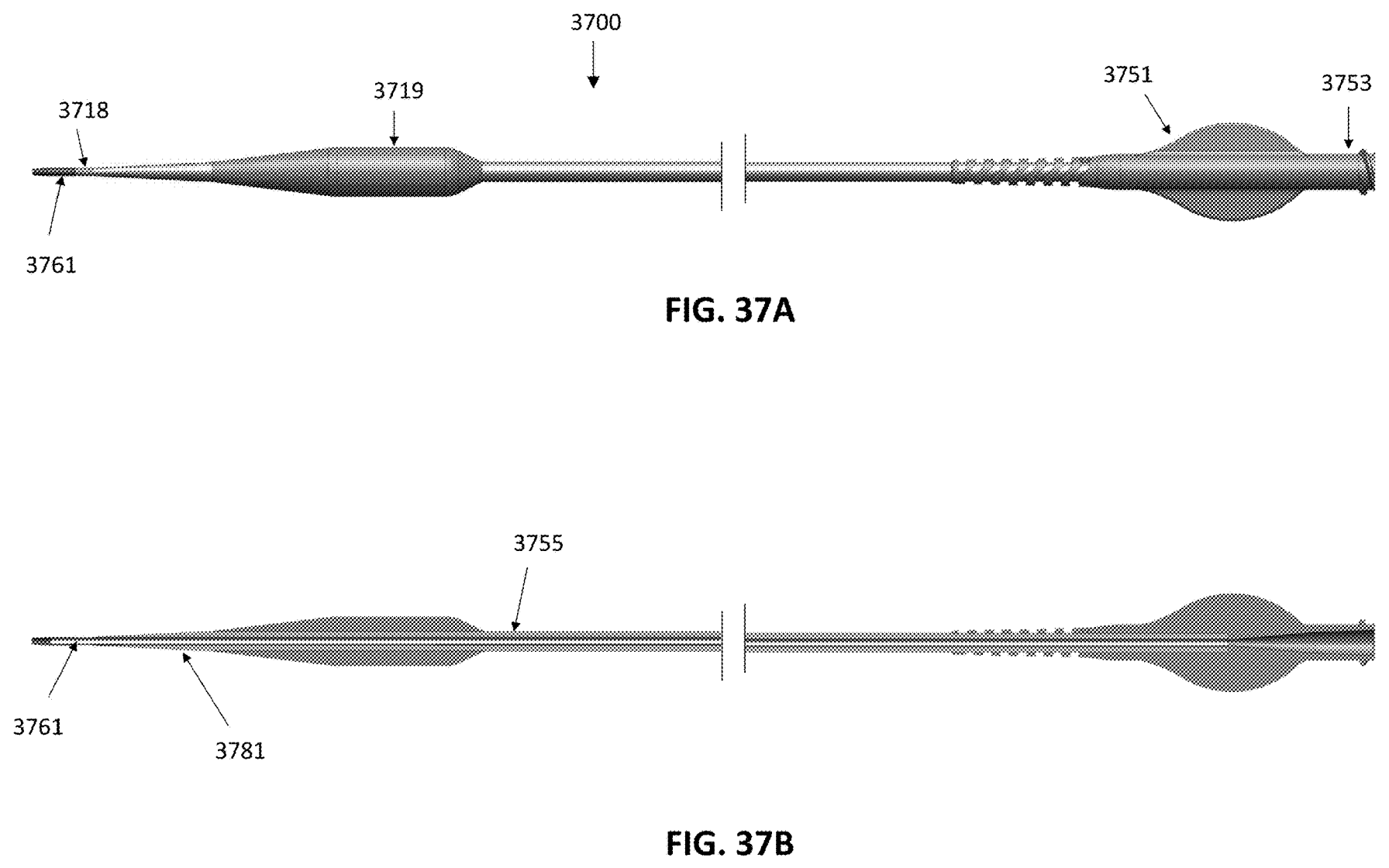

FIGS. 37A and 37B illustrate examples of a venous inner catheter 3700 (venous daughter catheter) that may be used with any of the venous sheaths described herein. The venous inner catheter shown in FIGS. 37A and 37B includes a soft distal tip 3761 which may be radiopaque as described above. The elongate length of the venous inner catheter 3700 may be flexible and may include a coil and/or braid reinforcing it along its length. The proximal end may include a hub 3751 and a port 3753) e.g., for a guidewire (not shown). The distal end region may include a radially enlarged region 3719 for engaging and sealing against the distal tip of the venous sheath, as shown in FIG. 35. This tip engagement region 3719 is tapered on both sides, proximally and distally, but may have a more gradual distal taper 3781; in the example of FIGS. 37A-37B the catheter shaft gradually tapers distally down to provide a low crossing profile. The proximal region 3755 may gradually taper up (e.g., thicken) to increase pushability and kink resistance of the venous inner catheter. The venous inner catheters described herein may therefore be used to advance the venous sheath over a guidewire or otherwise within the body while preventing fishmouthing or catching of the venous sheath on the lumen wall.

Figure 42A:
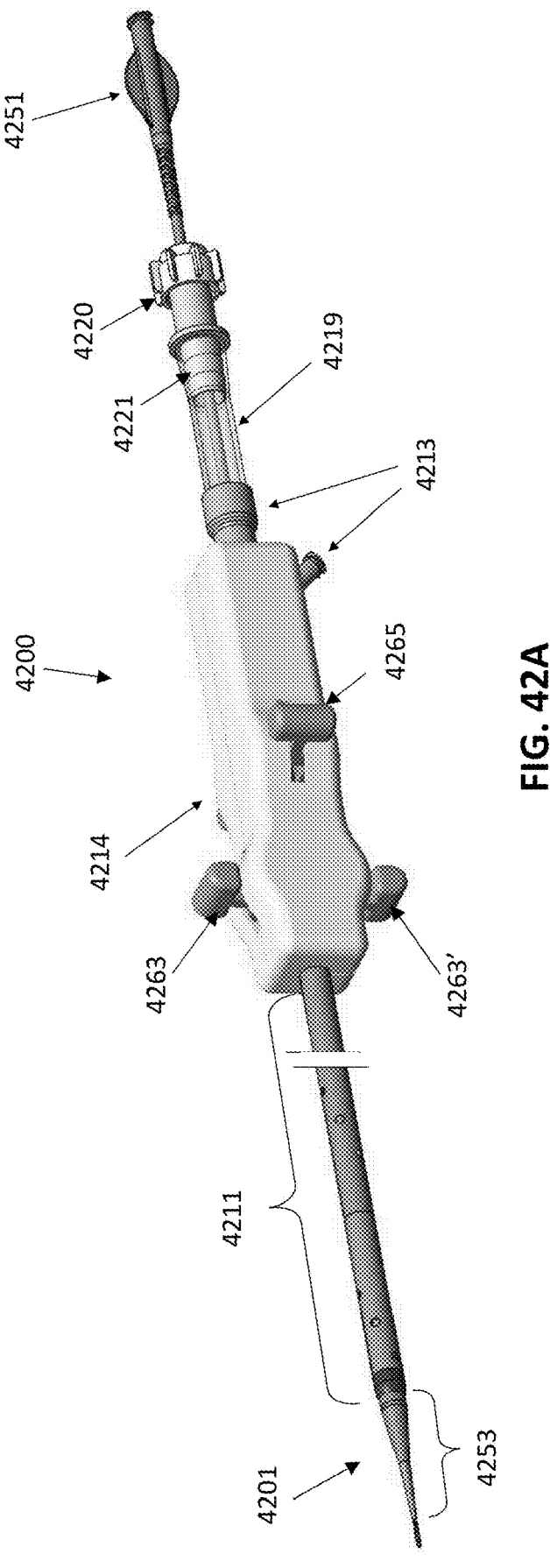
FIGS. 42A-42D illustrate an example of a venous sheath system as described herein.
Figures 42B, 42C, 42D:
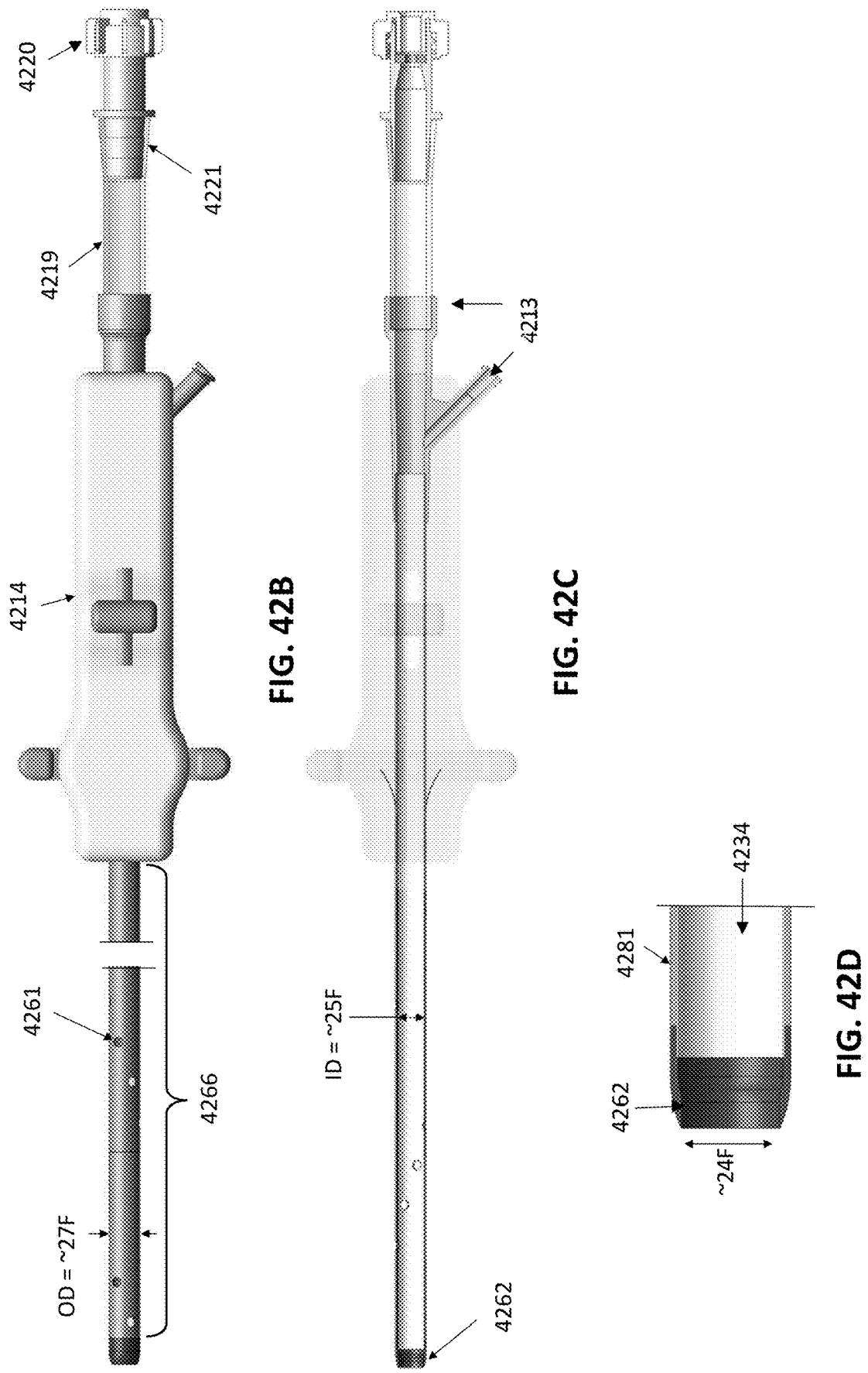

FIG. 42A illustrates another example of a venous sheath set with a venous sheath 4200 and a septum dilator 4201 nested within the venous sheath that may be used in any of the methods and apparatuses described herein. FIGS. 42B-42D show just the venous sheath; in FIG. 42C the proximal handle of the venous sheath has been made transparent. In the venous sheath 4200 shown in FIGS. 42A-42D, the distal end region of the venous sheath shaft 4211 may be steered (deflected) in two planes, which may be arranged perpendicular to each other. In this example, the distal end region of the venous sheath may be bidirectionally steered, e.g., in a first plane or a second plane, using one or more controls on the proximal handle 4214 configured as a bidirectional two-plane deflection handle. The handle also includes a y-arm with a side port 4213, similar to the example of FIGS. 34A-34B (configured to couple to an ECMO system through a pinch tubing), and a through port, in fluid communication with the lumen of the venous sheath. The venous sheath is also connected to a flexible tubing 4219 and a removable hemostasis valve 4220 (connected to the flexible tubing by a removable barb connector 4221). The dilator 4201 is shown inserted through the hemostasis valve and out of the distal end of the venous sheath so that a distal end region 4253 of the dilator catheter extends distally from the venous sheath and is sealingly engaged with the distal tip of the venous sheath.

On the handle 4214 of the venous sheath, the handle includes four controls (two sets of controls) for steering the distal end region of the venous sheath. The first set includes two opposing levers 4263, 4263' configured to pull a pair of complementary tendons (not shown) that operate opposite to each other. The first control 4263 in the first set pulls a first tendon to bend the distal end region of the shaft in a first direction while extending a second tendon in the opposite direction. The second tendon is arranged on the opposite side of the elongate shaft. Pulling the second control 4263' in the first set pulls the complementary second tendon to bend the distal end region in the direction opposite from the first direction (e.g., 180 degrees off of the third direction) and extend the first tendon. Similarly, the first control 4265 in the second set pulls a third tendon to bend the distal end region of the shaft in a third direction while extending a fourth tendon in the second set in an opposite direction (180 degrees off of the third direction). The fourth tendon is arranged on the opposite side of the elongate shaft from the third tendon. Pulling the second control in the second set pulls the complementary fourth tendon to bend the distal end region in the direction opposite from the third direction and extend the third tendon.

The elongate shaft 4266 of the venous sheath may be reinforced, e.g., by a coil, braid, and/or laser cut hypotube, and may have different stiffnesses along its length. In particular, the shaft may be more flexible distally and less flexible (stiffer) proximally. The shaft also include a plurality of inflow openings (inlets) 4261, which may be referred to as LAVA inflow side holes.

The venous sheath may be any appropriate dimensions. For example the venous sheath may have an outer diameter (OD) of between 20 F-35 F and an inner diameter (ID) of between 18 F-33 F. In FIGS. 42A-42C the OD is shown as about 27 F along the elongate shaft and the ID of the inner lumen 4234 is about 25 F, while the distal tip 4262 tapers down by about 1 F (e.g., to 24 F). FIG. 42D shows the distal tip in greater detail, showing the soft distal tip couped to the outer jacket 4281 and enclosing the inner lumen 4234 that may be lubricious, e.g., coated with a lubricous coating and/or including a lubricous inner liner (e.g., a PTFE liner).

Figure 43A:
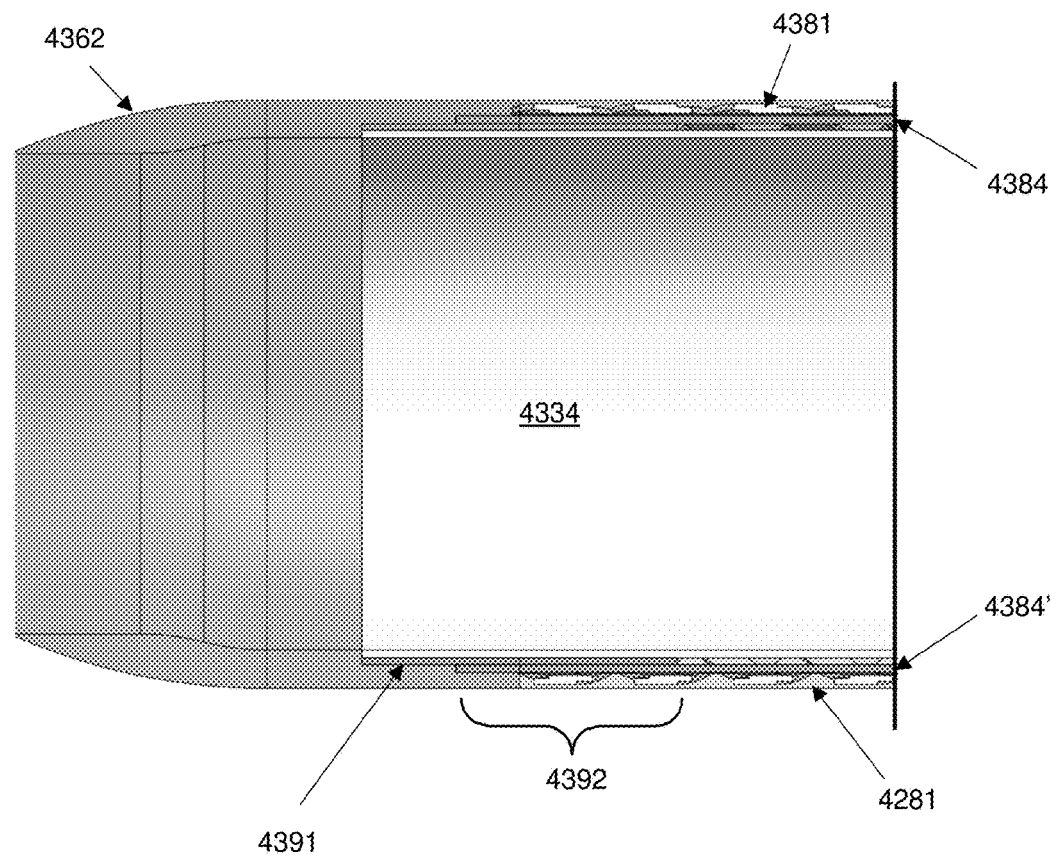
FIGS. 43A-43B illustrate details of one example of a venous sheath similar that shown in FIGS. 42A-42C.
Figure 43B:
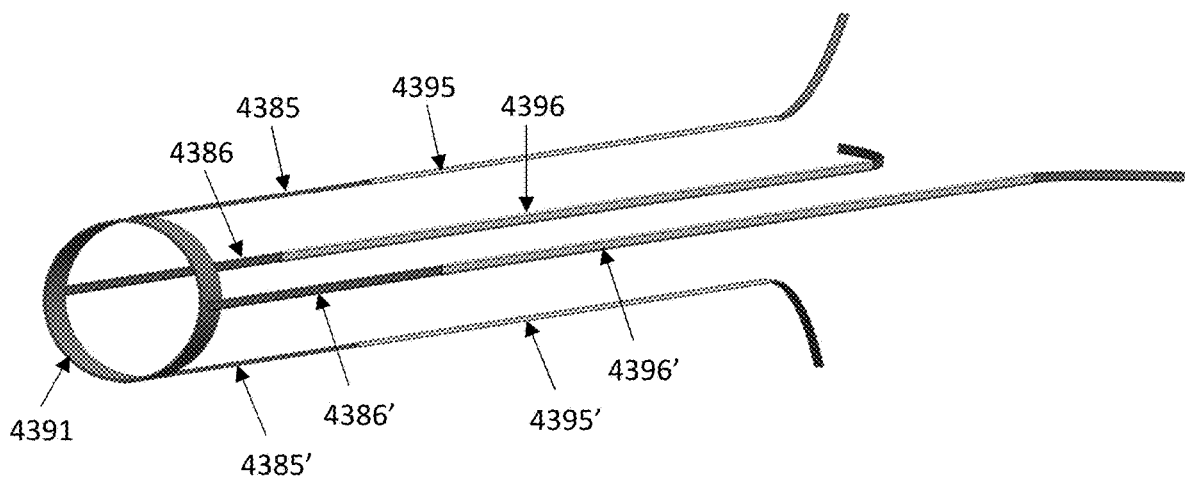

FIGS. 43A-43B illustrate one example of venous sheath shaft deflection elements that may be used. For example, in FIG. 43A the section through the distal end region (including the soft and radiopaque distal tip 4362, also shows a portion of elongate shaft, which in this example is reinforced by a braid 4381. The lumen 4334 (which may be lubricous) passes through the elongate length of the venous sheath. FIG. 43B shows just a portion of the four pull wires (e.g., two opposing sets of pull wires) 4385, 4385', 4386, 4386'. The pull wires may be coupled to an anchor 4391 at a distal anchoring region 4392 of the pull wires, as shown in FIGS. 43A, and may extend along the length of the venous sheath. The pull wire anchor 4391 in this example is a distal band and may be welded and/or bonded to the pull wires. The pull wires are allowed to slide relative to the wall of the elongate member. In the distal deflection region the pull wires are exposed, while in the region proximal to the deflection region the pull wires are ensheathed within a pull wire lumen; for example, the first pull wire 4385 is ensheathed proximally within a first lumen 4395 and connected to a first control to apply/release tension on the first pull wire. The second pull wire 4385' (opposite the first pull wire) is ensheathed proximally within a second lumen 4395' and connected to a second control (complimentary to the first control) to apply/release tension on the second pull wire. The third pull wire 4386 is ensheathed proximally within a third lumen 4396 and connected to a first control to apply/release tension on the first pull wire. The second pull wire 4386' (opposite the first pull wire) is ensheathed proximally within a second lumen 4396' and connected to a second control (complimentary to the first control) to apply/release tension on the second pull wire. The first and second controls may be coupled so that they operate together (and opposite each other, e.g., tensioning the first pull wire may release tension on the second pull wire). Thus, the pull wires steering the venous sheath in this example are bi-directional, and provide deflection in two planes which may be operated together to steer in virtually any direction. Although four pull wires are shown in this example in any of the deflectable catheters described herein more or fewer pull wires and controls may be used. For example two pull wires could be used to provide uni-directional deflection; the user may rotate and torque the elongate shaft to direct and steer the distal tip.

Figure 44A:
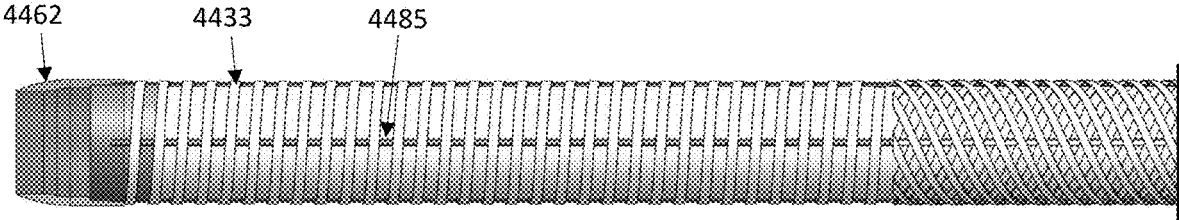
FIGS. 44A-44C illustrate examples of detail for a shaft deflection region of a venous sheath similar to that shown in FIG. 42B.
Figure 44B:
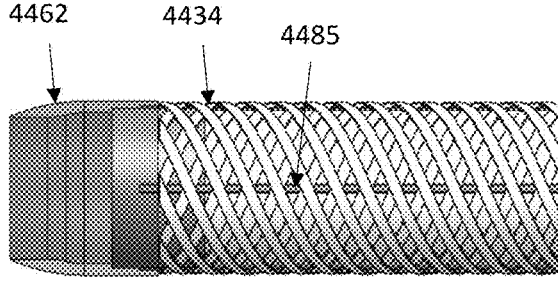
Figure 44C:
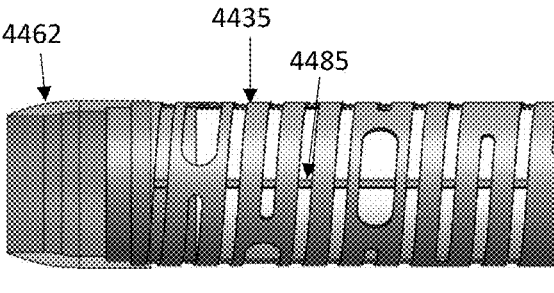

FIGS. 44A-44C shows examples of the deflection region of a venous sheath. In FIG. 44A the pull wire(s) 4484 are shown under a continuous coil 4433 that forms the shaft reinforcement for the deflection region. In FIG. 44B the shaft reinforcement 4434 is a multi-layer coil with opposing windings. FIG. 44C shows an example in which the shaft reinforcement 4435 is a laser-cut structure (e.g., hypotube, curled sheet, etc.). FIGS. 44A-44C shows these apparatuses without the outer jackets. Other examples of shaft reinforcement may include a continuous braid, coil/braid hybrids, and other laser-cut patterns.

Figure 45A:
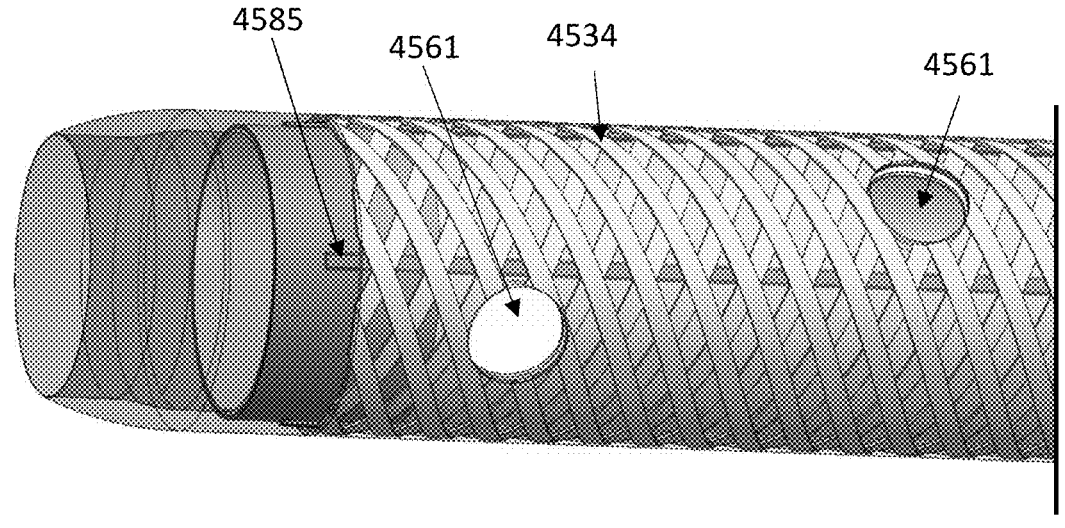
FIGS. 45A-45B show examples of a distal end region of a venous sheath showing side openings for LAVA decompression through the venous sheath.
Figure 45B:
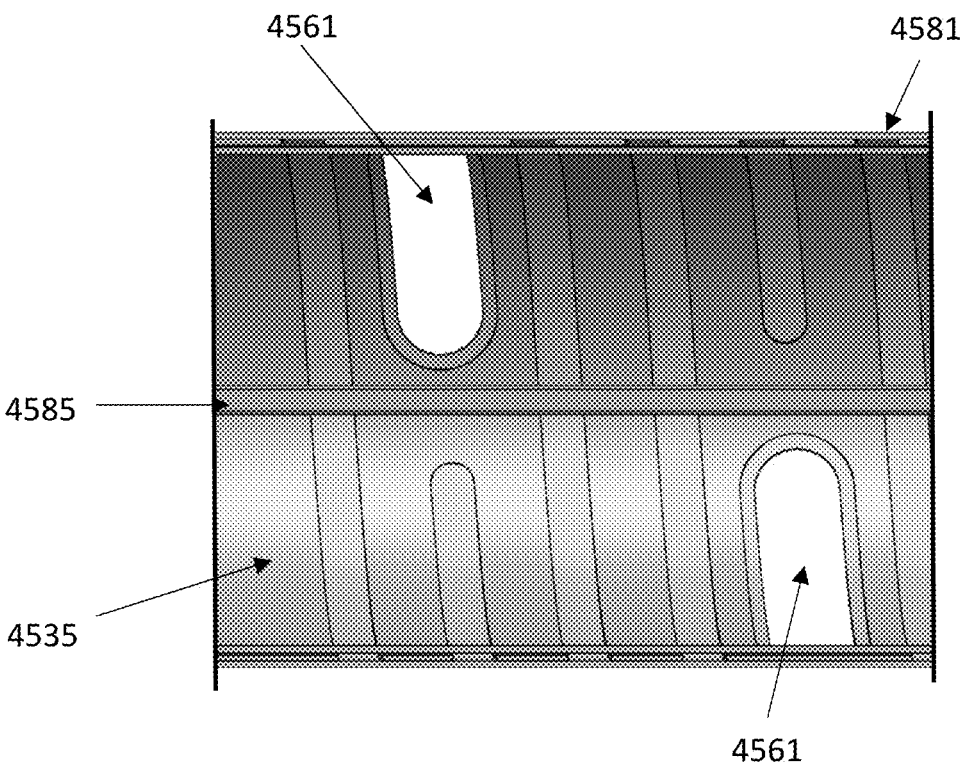

FIGS. 45A-45B illustrate examples of the positioning of the inlet ports (side holes) formed through the wall of the venous sheath in the examples shown in FIGS. 42A-42D, 43A-43B and 44A-44C, in which the distal end region is steerable/deflectable. In this case the addition of these side holes, which may act as LAVA decompression side holes, may require that the holes be punched between pull wires. In FIG. 45A, the side holes 4561 are formed between the pull wires 4585 so that the holes remain open as it is deflected during use. In FIG. 44A the support frame 4534 at the deflectable distal end region is formed as a continuous coil with opposing windings, similar to the example shown in FIG. 44B.

FIG. 45B shows an example of a venous sheath having a laser-cut shaft support 4535, in which integrated holes 4561 maybe included to allow the polymer jacket and liner to be "punched out". The inlet ports may be arranged as interruptions along a spiral or linear pattern that provides space for the pull wires 4585 to run between the holes, as shown. The polymer outer jacket 4581 covering the outer surface (and inner surface in some examples) is transparent in FIGS. 45A and 45B. These device may also include a liner (e.g., a lubricious liner) not shown in this example.

Method of Use

In operation the apparatuses described herein, including the arterial sheath sets and the venous sheath sets may be used as described above (e.g. in FIGS. 15A-15I, 16A-16B, 17A-17I, 22A-22G, and 23A-23G. FIGS. 46A-46J, 47A-47J, and 48A-48J also illustrate examples of methods of using the apparatuses described above, including in particular, the method of using these arterial sheath sets and venous sheath sets. The use of the arterial sheath sets (e.g. including a mother, daughter, and one or more granddaughter catheters) may increase the safety and ease of traversing the 180° band at the LV apex, as well as allowing a greater amount of reproducibility in working with virtually any size heart. These apparatuses may enhance access to cross traverse virtually any aorta with the mother/cross pump ECMO systems described herein.

For example, these apparatuses (e.g., systems, devices, etc.) may include an arterial sheath set with a highly flexible inner catheter including a first inner catheter having a balloon with an inflated diameter that is greater than about 5 mm to allow safe passage through the mitral valve, which may be used in combination with a second inner catheter that is configured to be steered (e.g., deflected) to allow the smaller inner catheter (first inner catheter) to be deflected across the mitral valve and then also deflected around the LV apex to allow the smaller balloon catheter to traverse into the LV outflow track across the valve and ultimately into the arch of the aorta and possibly descending aorta. This secondary deflection inner catheter, which is able to be advanced over the innermost catheter allows the possibility of advancing a stiff wire through the innermost catheter, and then advancing the arterial sheath (e.g., the ECMO sheath) over the inner catheter, innermost catheter and stiff wire into the ascending aorta.

Figures 46A, 46B:
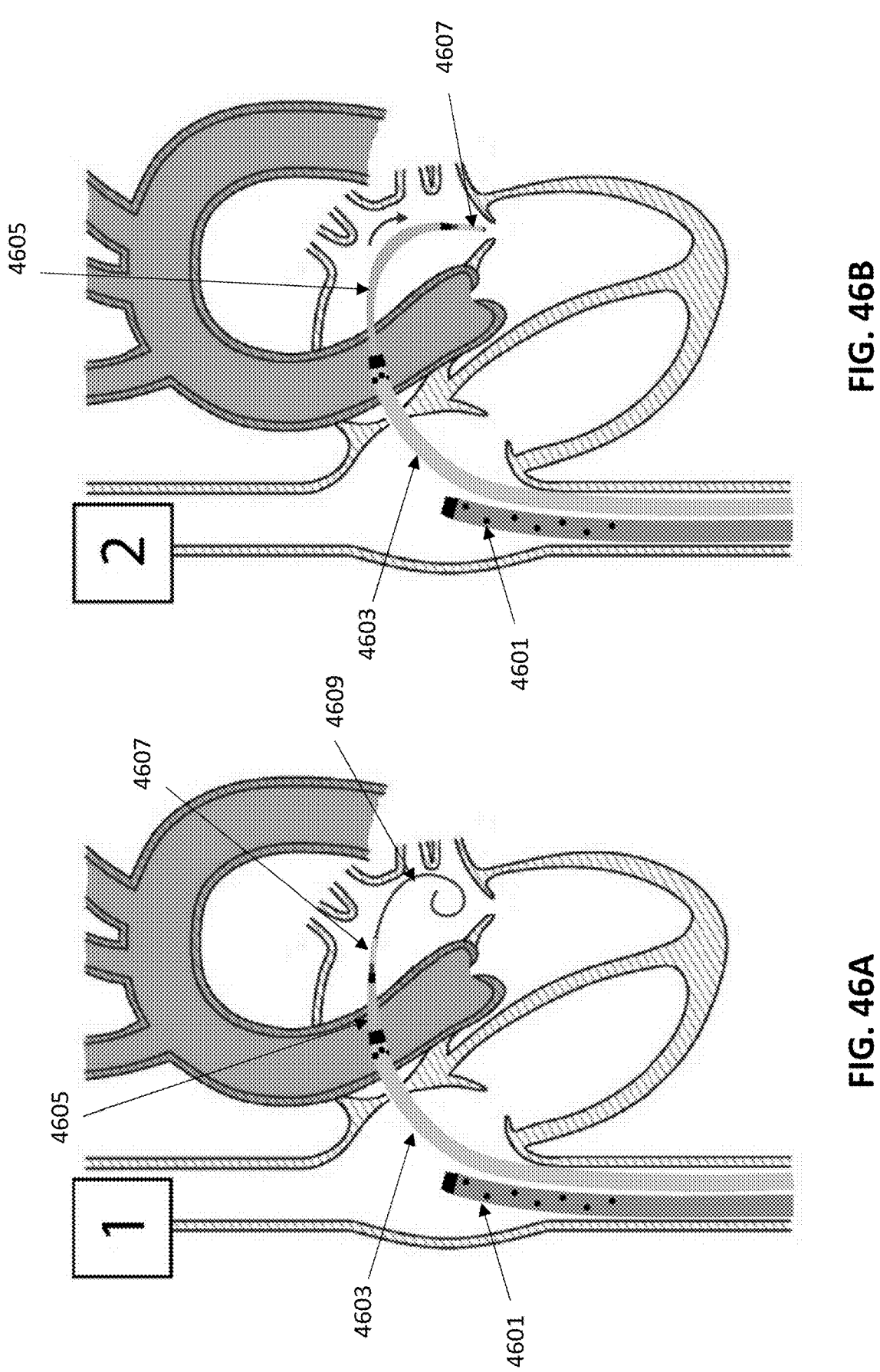
FIGS. 46A-46J illustrate one example of a method of performing a procedure using the arterial sheath set and a venous sheath as described herein.
Figures 46C, 46D:
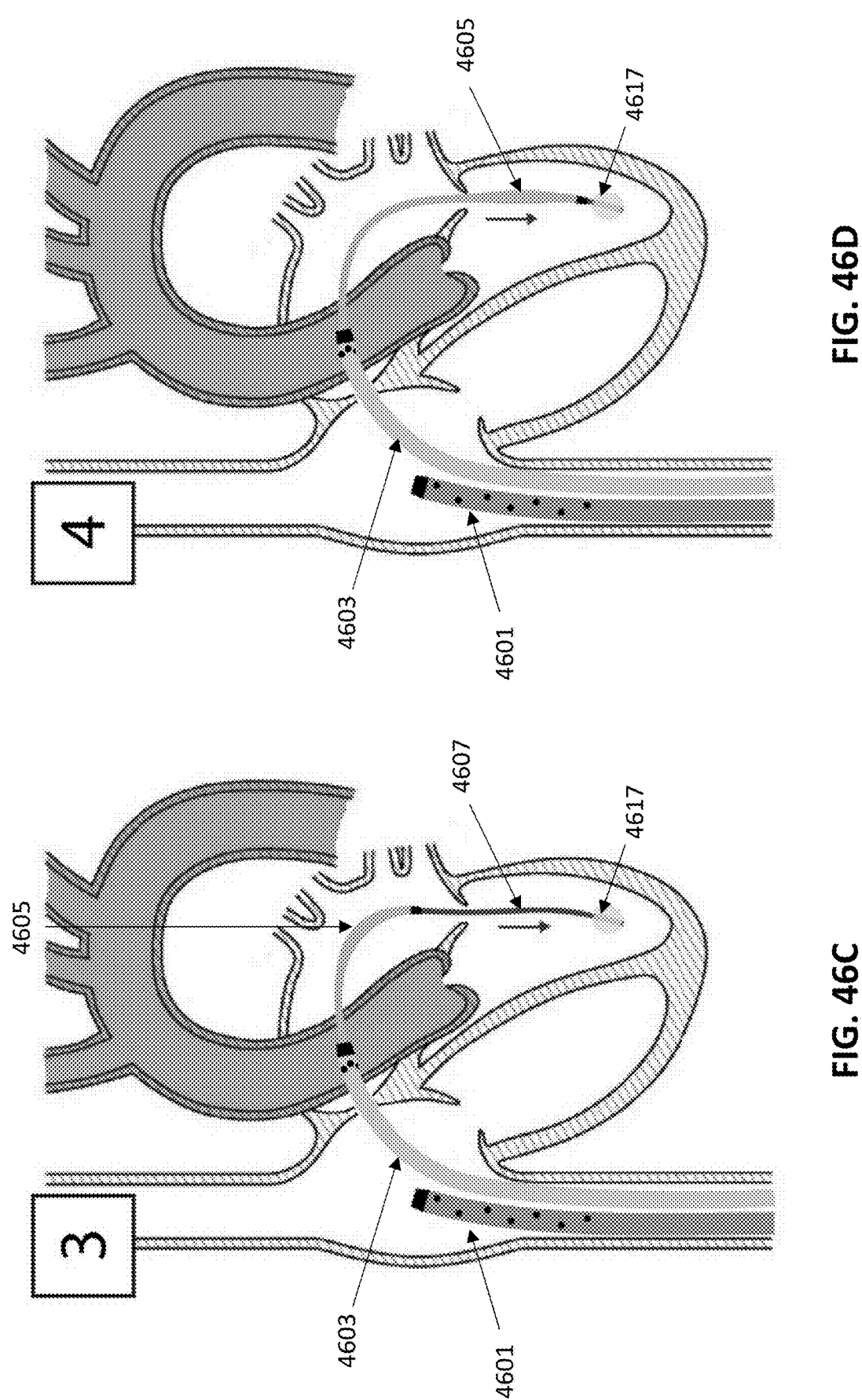
Figures 46E, 46F:
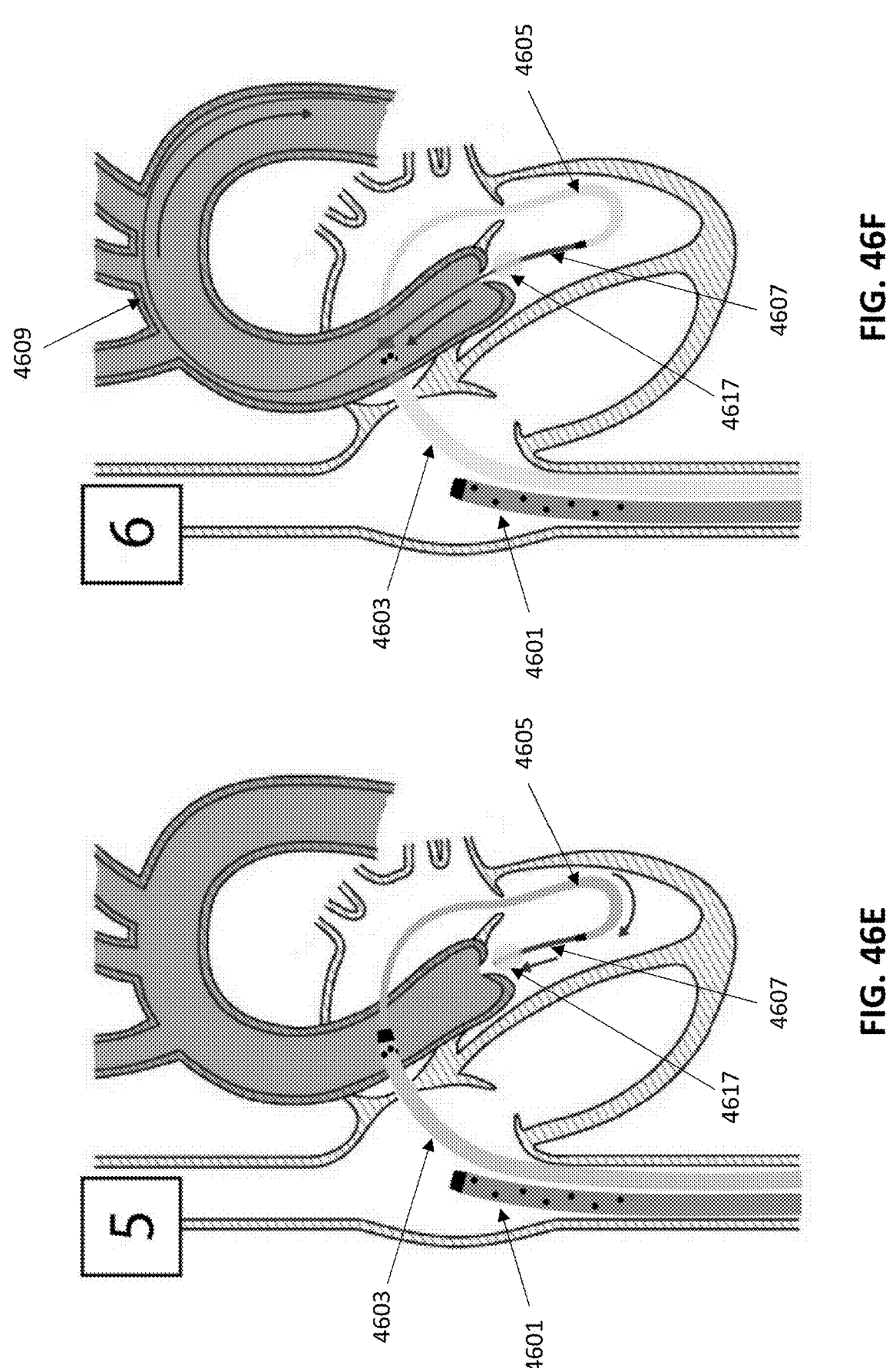
Figure 46H:
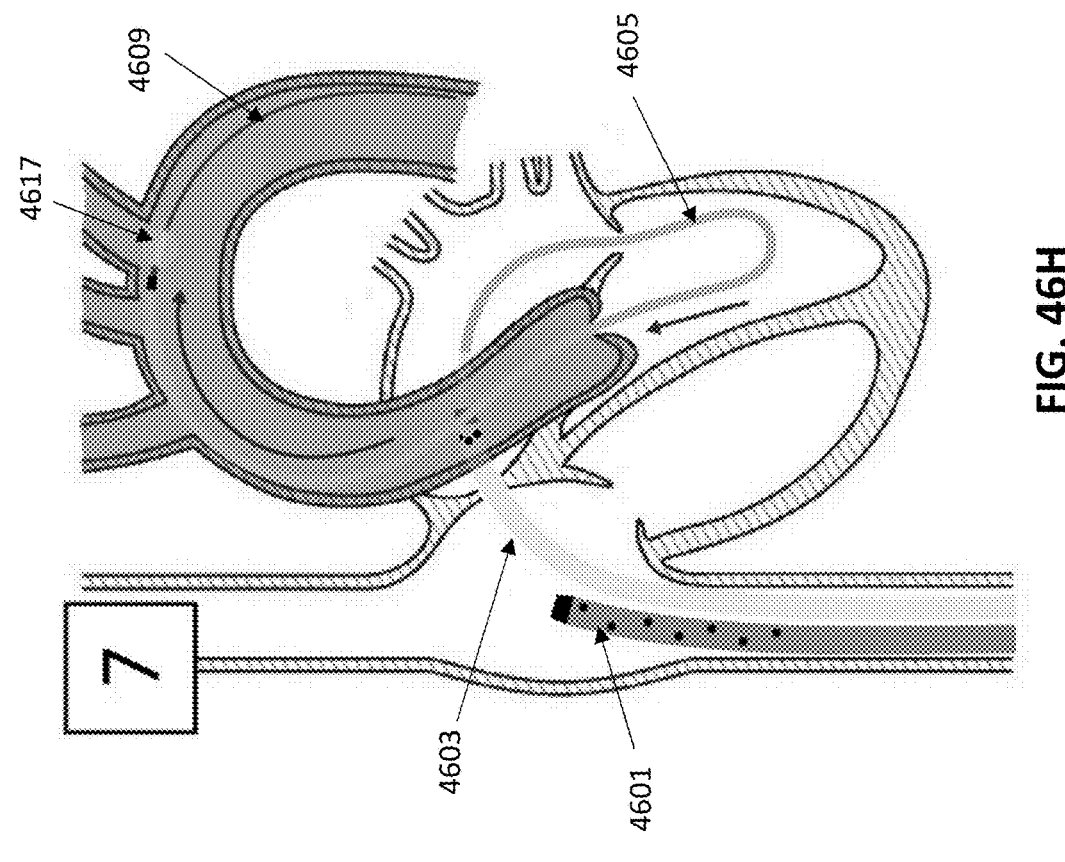
Figure 46G:
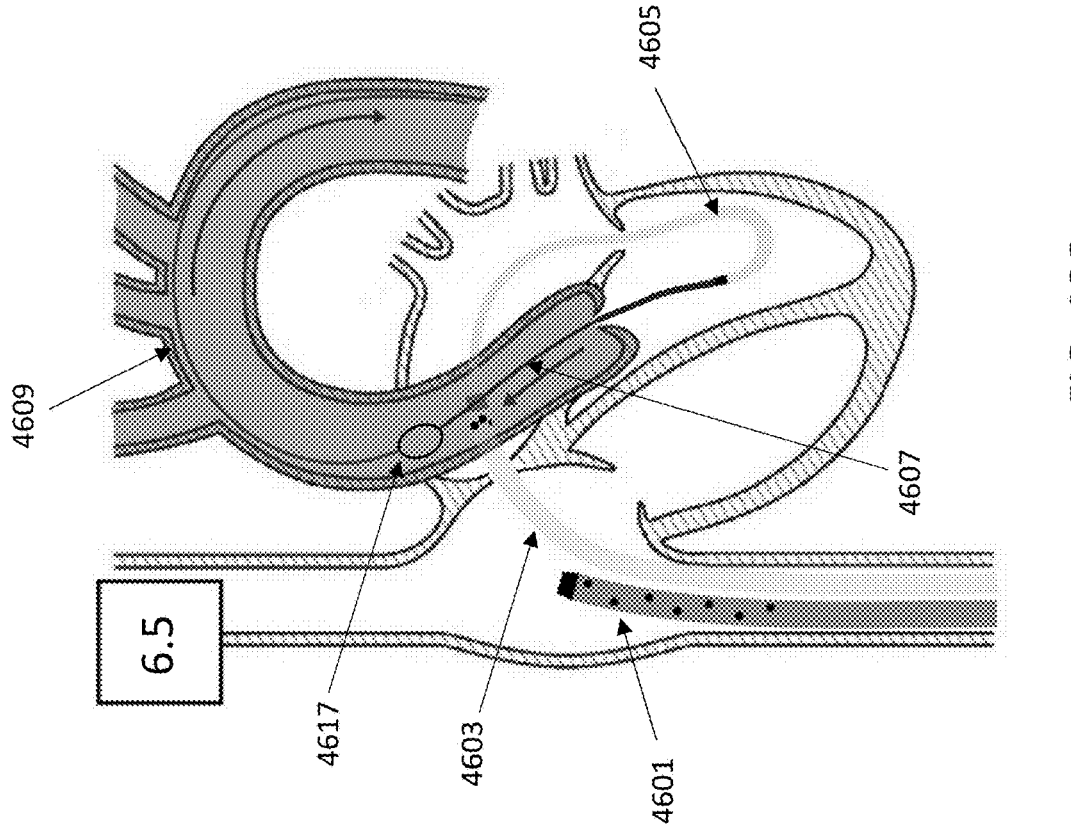

For example, FIGS. 46A-46J illustrate one example of a method as described herein. In this example, a venous sheath 4601 may be positioned in the inferior vena cava while the arterial sheath set (including a mother 4603, daughter 4605 and granddaughter 4607) are nested together and advanced through the atrial septum into the left atrium (LA) over a highly flexible (e.g., "floppy") guidewire, such as a 0.035" guidewire 4609, as shown in FIG. 46A. In FIG. 46B, the daughter 4605 and granddaughter 4607 are advanced together into the LA and the daughter catheter 4605 is deflected, pointing the granddaughter towards the mitral valve (MV) orifice. The guidewire may be withdrawn into the nested system. The granddaughter balloon 4617 may then be inflated, and the granddaughter catheter 4607 (only) may be advanced across the MV toward the left ventricle (LV) apex, as shown in FIG. 46C. In FIG. 46D, the daughter catheter 4605 is advanced over the granddaughter 4607 across the MV and into the LV. In FIG. 46E, the daughter catheter 4605 deflects the granddaughter catheter 4607 by about 180°, and the granddaughter 4607 is advanced to the LV outflow track. the distal balloon 4617 of the granddaughter may be used to center the granddaughter relative to the valve, while protecting the tissue (e.g., valves, chordae tendinea, etc.). Once the granddaughter is positioned and/or centered, a guidewire 4609 (the same or a different guidewire, e.g., a stiffer guidewire) may be advanced across the aortic valve (AV) into the descending aorta, as shown in FIG. 46G. In FIG. 46H, the granddaughter has been advanced across the AV into the left subclavian artery over the guidewire 4609, in this example with the distal expander (balloon) 4617 expanded, and the daughter 4605 has been tracked over the granddaughter. The guidewire may be swapped for a different stiffness guidewire and introduced to prior to advancing the mother catheter 4603 to provide more support.

Figures 46I, 46J:
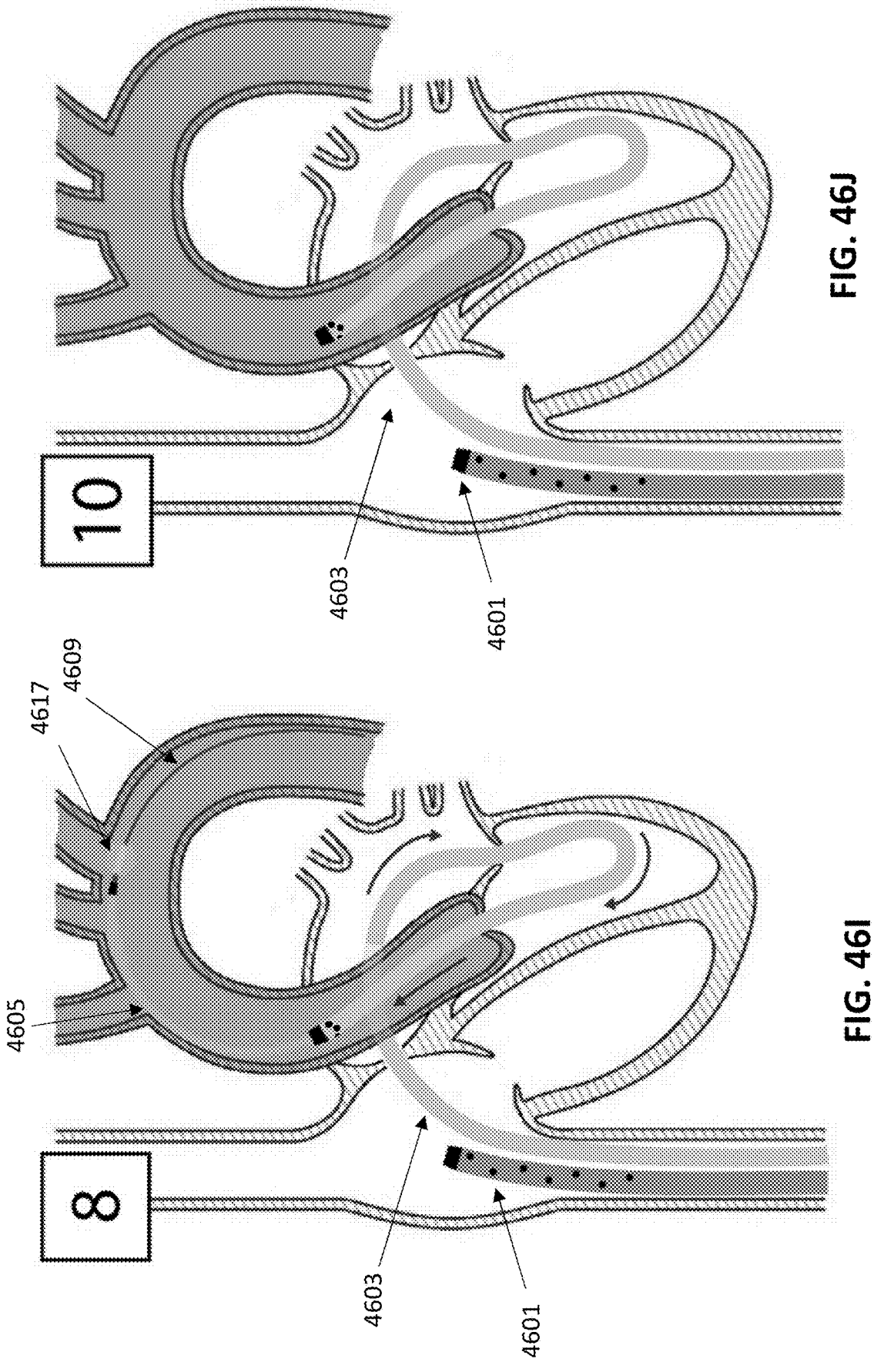

In FIG. 46I the mother catheter 4603 is shown being advanced over the daughter 4605 (and granddaughter 4607 nested within the daughter) into the descending aorta. The balloon 4617 may remain expanded during this procedure. The daughter 4605 and granddaughter 4607 may be completely withdrawn (separately or together), and the arterial sheath 4603 (mother) may be positioned within the ascending aorta, while the venous sheath remains in the inferior vena cava. The guidewire may be withdrawn and the system is ready for use (e.g., for ECMO) Note that in any of these methods the daughter and/or granddaughter may be modified so that the same catheter nested within the mother (arterial sheath) may include both steering and a balloon at the distal end region (e.g., similar to the apparatus shown in FIGS. 38A-38C and 39A-39G). For example, FIGS. 47A-47J illustrate a method of positioning an arterial sheath set and a venous sheath set for ECMO in which the same daughter/granddaughter catheter includes both a steerable distal region and a more distal expander (e.g., balloon).

Figures 47A, 47B:
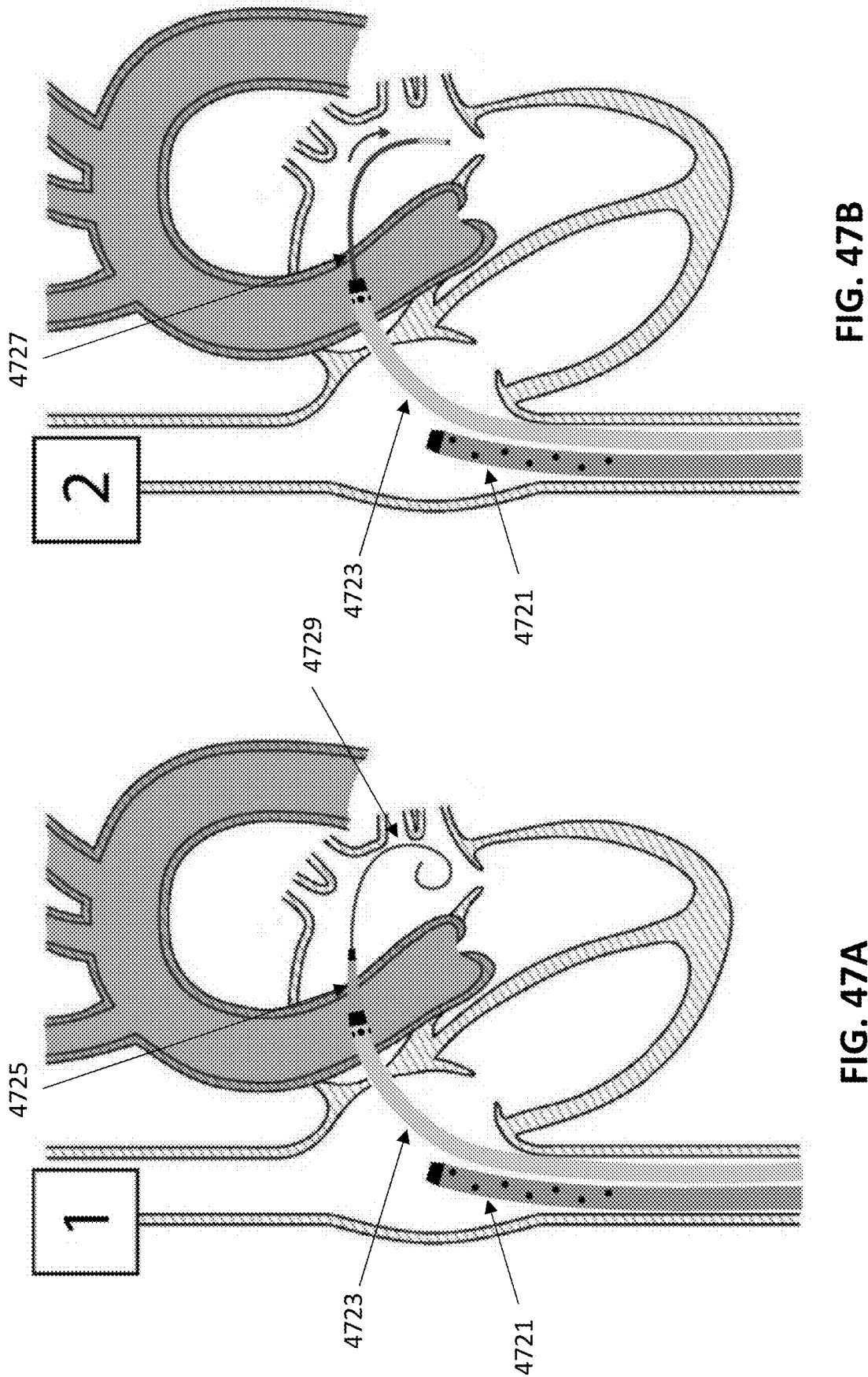
FIGS. 47A-47J illustrate an example of a method of performing a procedure including positioning an arterial sheath set and a venous sheath set for ECMO in which the same daughter/granddaughter catheter includes both a steerable distal region and a more distal expander (e.g., balloon).
Figures 47C, 47D:
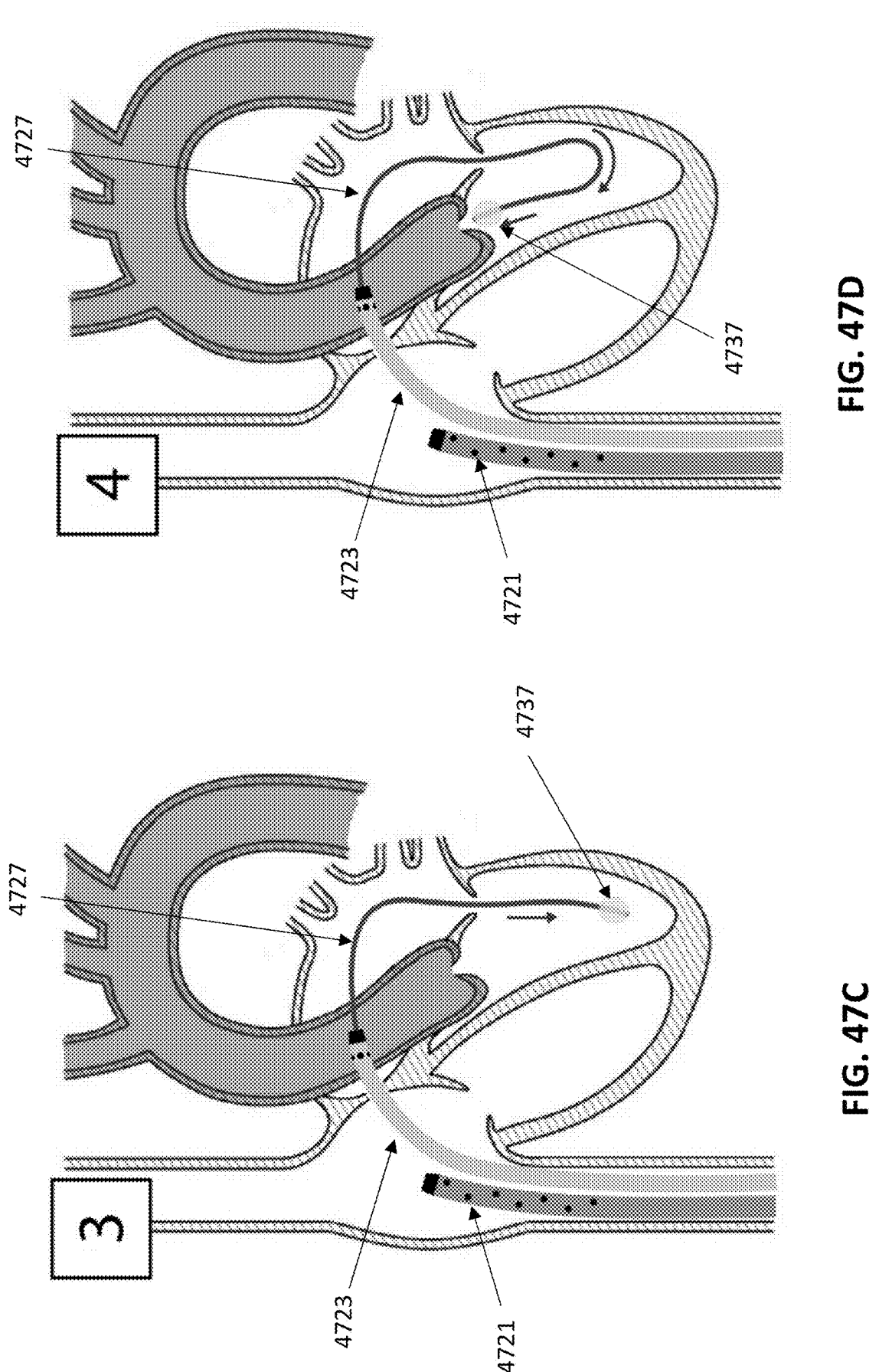

For example, FIG. 47A shows an arterial sheath (mother catheter 4723) and daughter configured as a septum dilator 4725 being advanced through the atrial septum into the left atrium (LA) over a guidewire (e.g., a 0.035" guidewire) 4729. The venous sheath 4721 is maintained in the inferior vena cava. In FIG. 47B, the daughter catheter 4725 (septum dilator) has been removed from system, and a second daughter catheter 4727 (also referred to herein as a granddaughter, as it may fit nested within the daughter catheter 4725) that includes a deflectable (steering) region and a distal expander (e.g., balloon) is introduced and advanced into the la and deflected towards the mitral valve (mv) orifice. The guidewire 4729 may be withdrawn into system and the balloon 4737 of the granddaughter catheter may be inflated and advanced across the MV toward the left ventricle (LV) apex, as shown in FIG. 47C. In FIG. 47D the granddaughter catheter 4727 is deflected, using the steering region, by 180°, and advanced to the LV outflow track with the expander (balloon 4737) expanded.

Figures 47E, 47F:
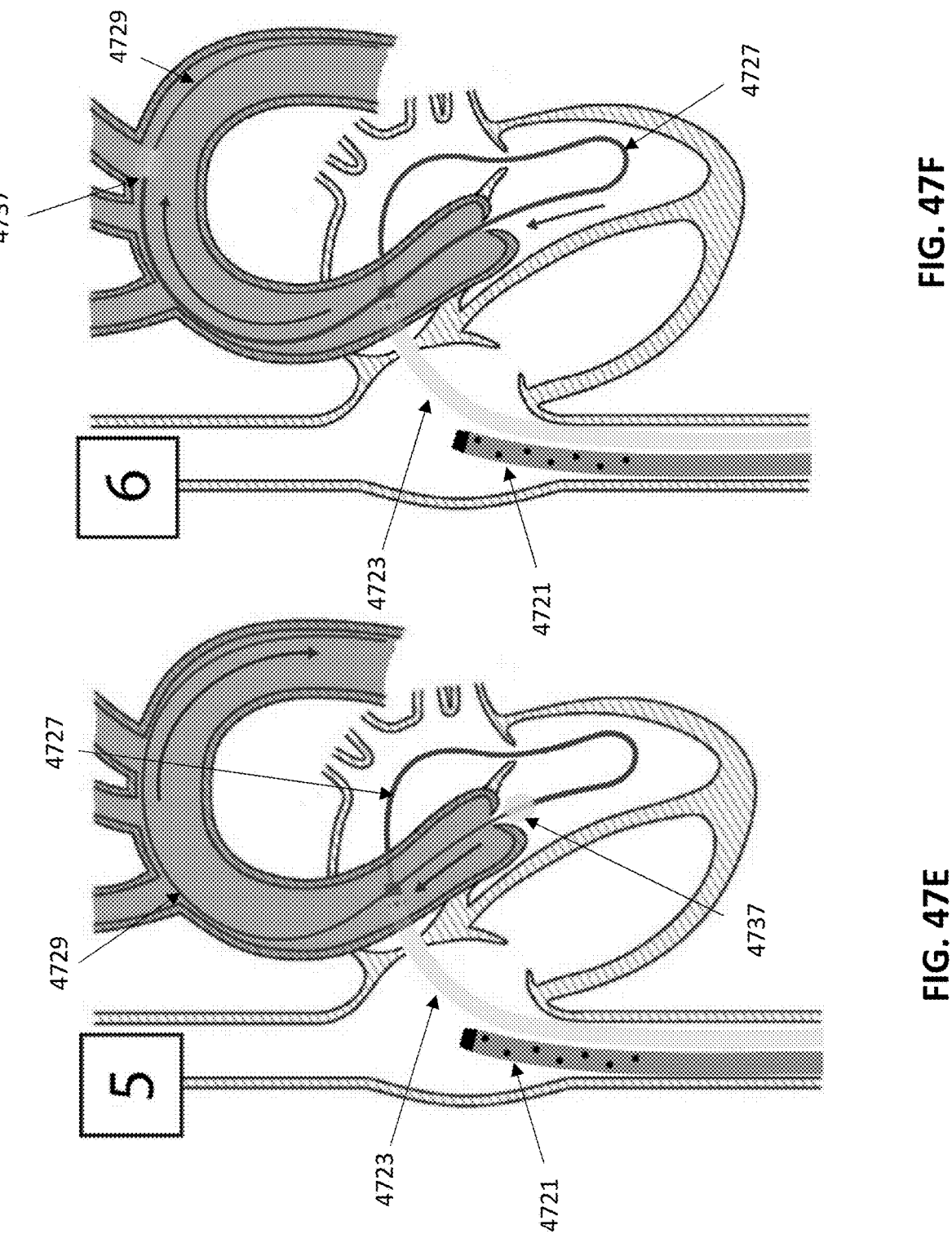
Figure 47H:
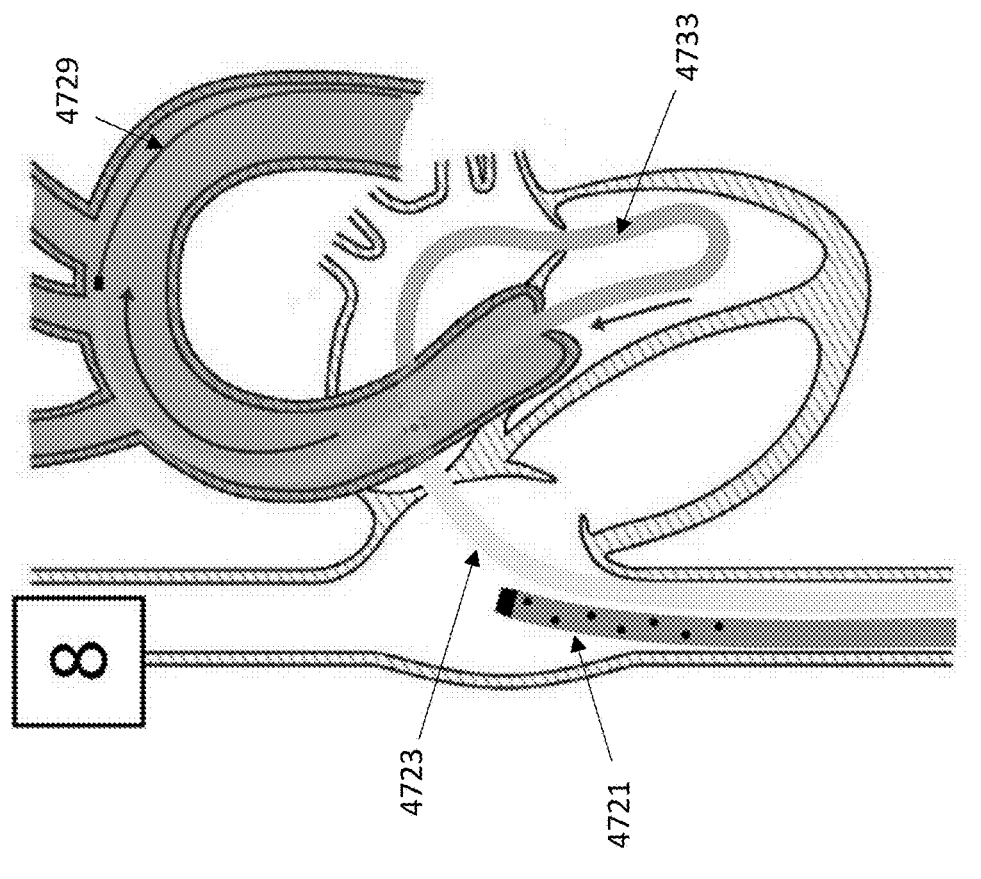
Figure 47G:
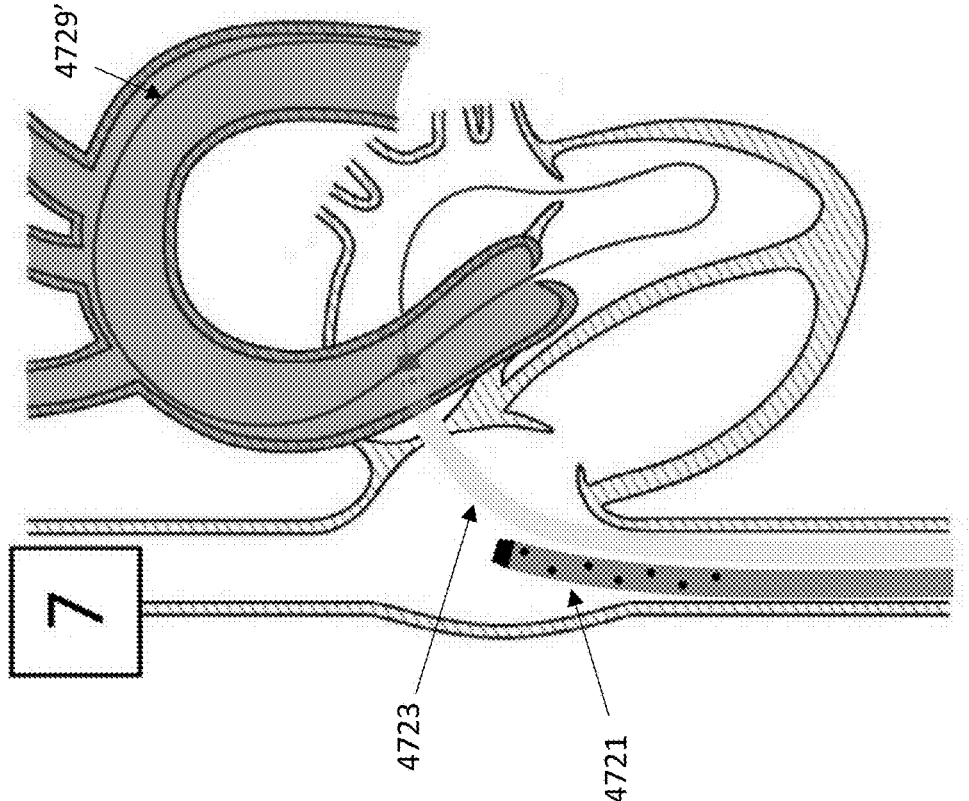

As shown in FIG. 47E, a guidewire (e.g., the same or a different guidewire as used in FIG. 47A (such as, e.g., a stiffer guidewire) may be extended through the granddaughter catheter and advanced across the aortic valve (AV) into the descending aorta. In FIG. 47F, the granddaughter may be advanced (with the balloon expanded) across the AV to the left subclavian artery, as shown. In FIG. 47G a guidewire 4729' (such as a stiff guidewire) may be exchanged (or the same guidewire may be used) and the granddaughter catheter 4727 may be removed from the system. Thereafter, as shown in FIG. 27H, a tapered and flexible elongate daughter catheter 4733 (see, e.g., FIGS. 41A-41C) may be introduced and advanced over the guidewire (e.g., stiff guide wire) towards the left subclavian artery. The daughter catheter (inner catheter 4733) is tapered over its elongate length and may act as a dilator having a highly flexible at tip, enhancing tracking over the guidewire, with progressively less flexibility (greater stiffness) towards the proximal end. This may enhance tracking of the arterial sheath (mother) 4723 over the inner arterial catheter (daughter) 4733.

Figures 47I, 47J:
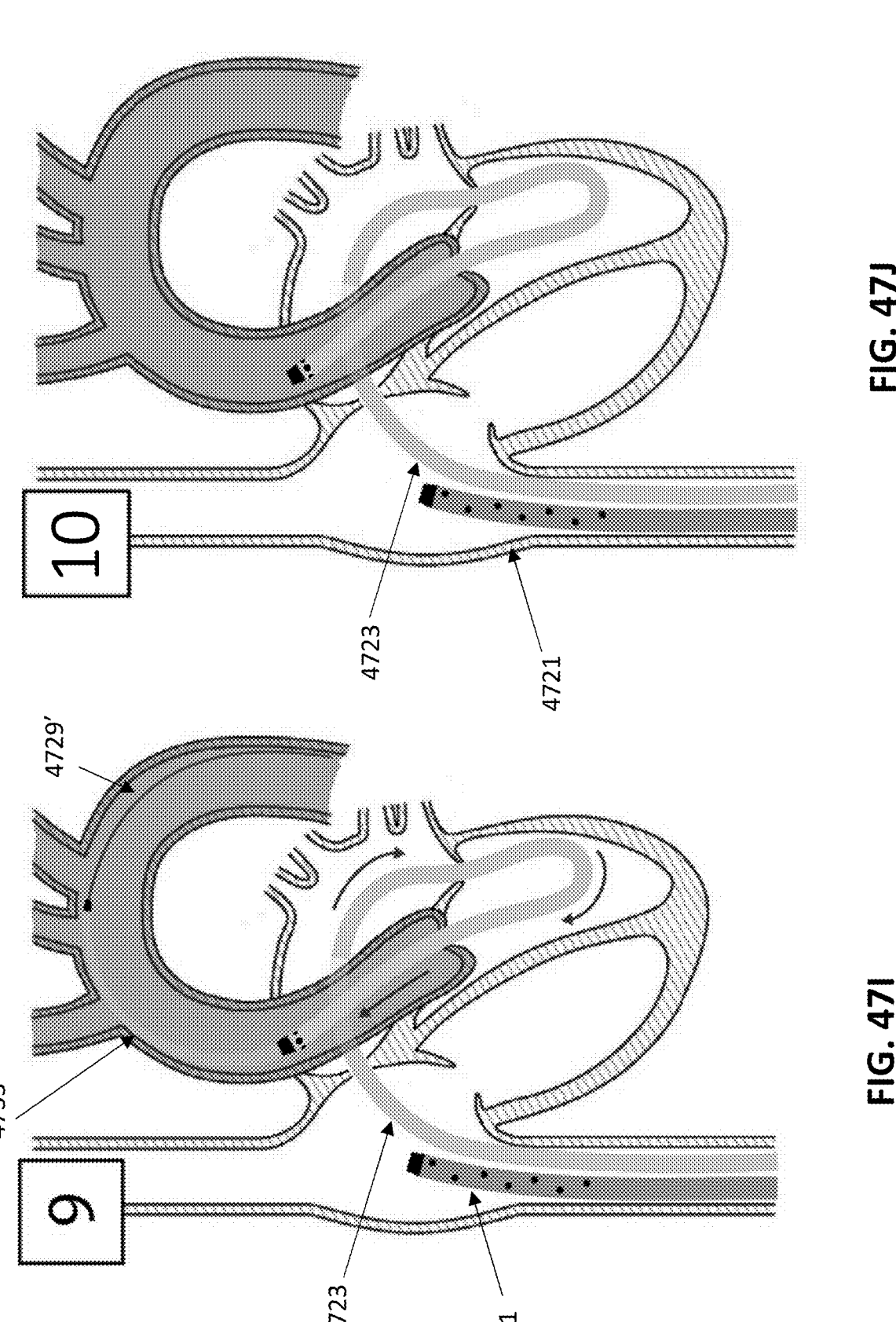

Once the daughter catheter 4733 is positioned, the mother catheter (arterial sheath) 4723 may be advanced over the tapered daughter catheter into the ascending aorta, supported by the tapered daughter catheter and the stiffer guidewire 4729', as shown in FIG. 47I. In FIG. 47J, the daughter catheter (long tapered daughter catheter 4733) may be completely withdrawn and the arterial sheath (mother catheter 4723) may be positioned within the ascending aorta by advancing over the guidewire as shown. The guidewire may be removed with the daughter catheter 4733, as shown in FIG. 47J, or may be left in place, and the system is ready for use with the eternal ECMO pump apparatus.

Thus, in some examples, a highly flexible inner catheter (granddaughter catheter) that has a deflection region at the distal end (typically capable of deflecting at least 170 degrees (e.g., at least 175 degrees, at least 180 degrees, etc.) and also include an expander (e.g., a distal balloon, distal to the steering region), that may be expanded to a dimension greater than 5 mm may be used. This inner catheter (granddaughter) may be advanced from the left atrium across the mitral valve and then deflected around the LV apex and with wire guidance across the aortic valve into the ascending and eventually arch of the aorta and descending aorta. At this point, a stiff wire can be advanced/exchanged through this inner catheter. The inner catheter may then be removed and a dedicated long tapered dilator may be advanced over the stiff wire through the ECMO sheath that is stationed in the left atrium, such that it tracks over the guide wire through the mitral valve across the aortic valve into the ascending and possibly descending aorta. This highly taper catheter may begin with a tip that is in the range of five or six French and then tapers very gradually over at least 15 cm (e.g., 20 cm, 25 cm, 30 cm, etc.) and up to about 60 cm to an eventually more proximal dimension that would allow seamless connection to the outer catheter meaning the OD of the proximal part of this expander (e.g., dilator) as it meets, the outer catheter may be approximately 17 F or 18 F or larger, depending on the size (e.g., ID) of the ECMO sheath. Once the dilator inner catheter is advanced all the way through the valve into the descending aorta. The outer catheter sheath may be advanced over it into the ascending aorta. Then the stiff wire and dilator may be removed to allow the sheath to be hooked up to ECMO arterial outflow.

Figures 48A, 48B:
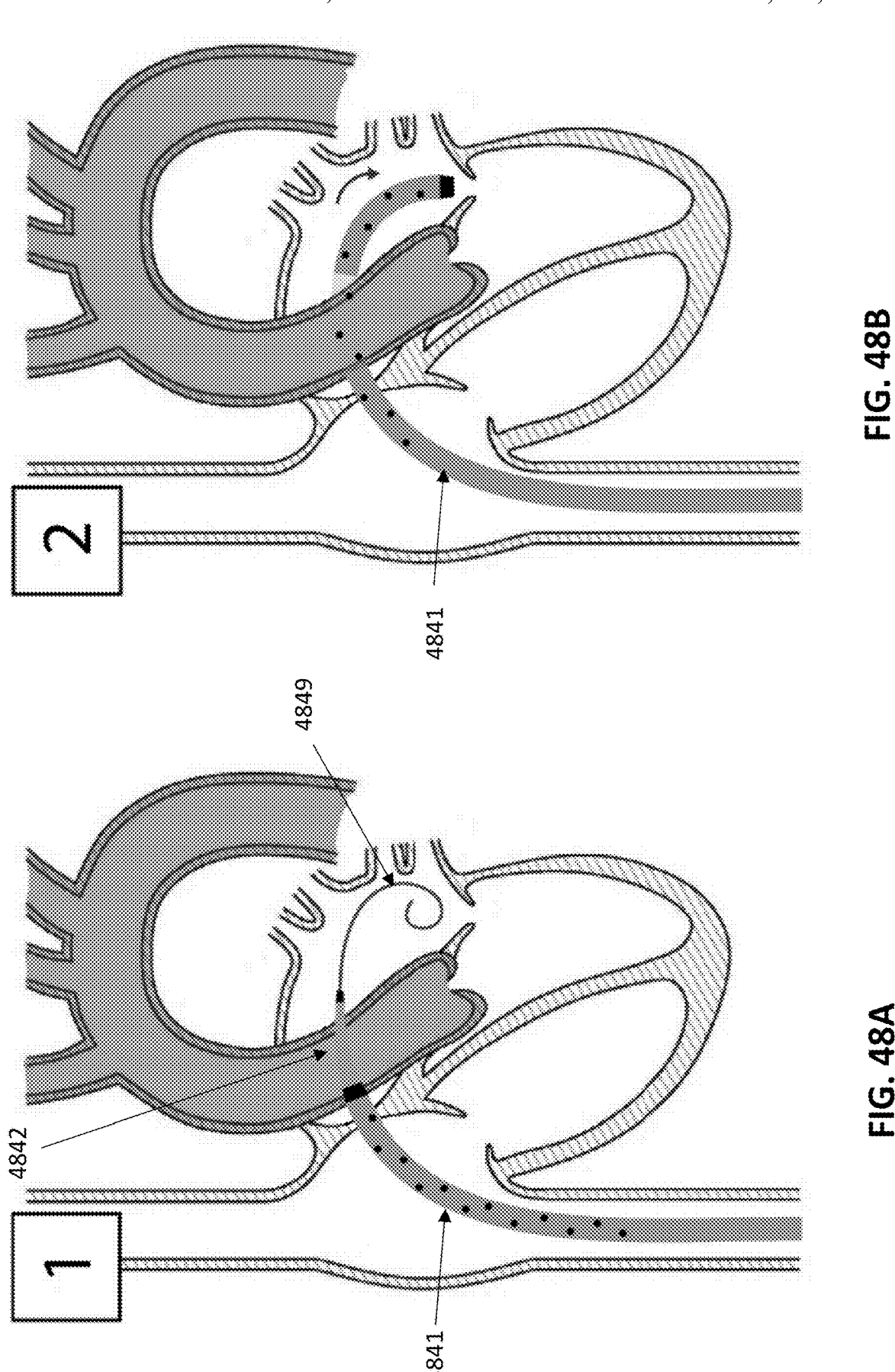
FIGS. 48A-48J illustrate an example of a method of performing a procedure in which the venous sheath set is configured to be nested over the arterial sheath set.

Note that in any of these methods the venous sheath may be nested over the arterial sheath set and may be advanced across the atrium/atria and/or ventricle(s). For example, FIGS. 48A-48J illustrate an example in which the venous sheath set is configured to be nested over the arterial sheath set. FIG. 48A shows a venous sheath system including a venous sheath 4841 and a venous daughter catheter (e.g., venous dilator or septum dilator) 4842 nested within the venous sheath being advanced through the atrial septum and into the left atrium (LA) over a first guidewire (e.g., a floppy, 0.035" GW).

Figures 48C, 48D:
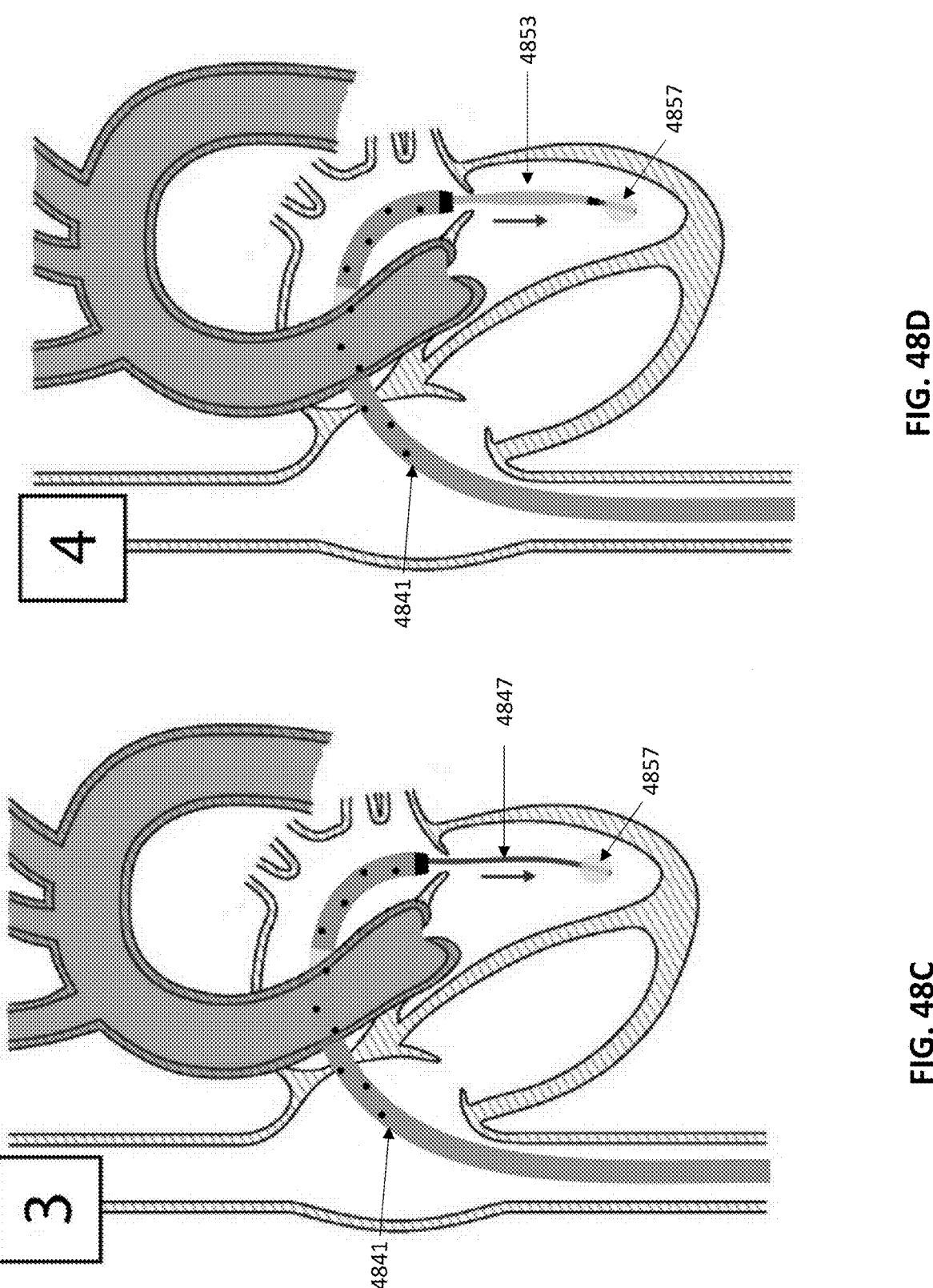

In FIG. 48B, the septum dilator, after dilating the septum, may be removed and the venous sheath 4841 may be advanced into the LA and deflected towards the mitral valve (MV) orifice. In some examples, this may be done by deflecting (steering) the distal end of the venous sheath, e.g., using an apparatus such as that shown in FIGS. 42A-42D. The guidewire 4849 may be withdrawn into system. In FIG. 48C, the arterial sheath set (including an arterial sheath, daughter catheter and/or granddaughter catheter) may then be introduced; in FIG. 48B the granddaughter having an expander (e.g., balloon) at the distal end region may be advanced distally to the LA, and the granddaughter 4847 may be advanced with the expander (e.g., balloon 4857) expanded, across the MV and toward the left ventricle (LV) apex.

Figures 48E, 48F:
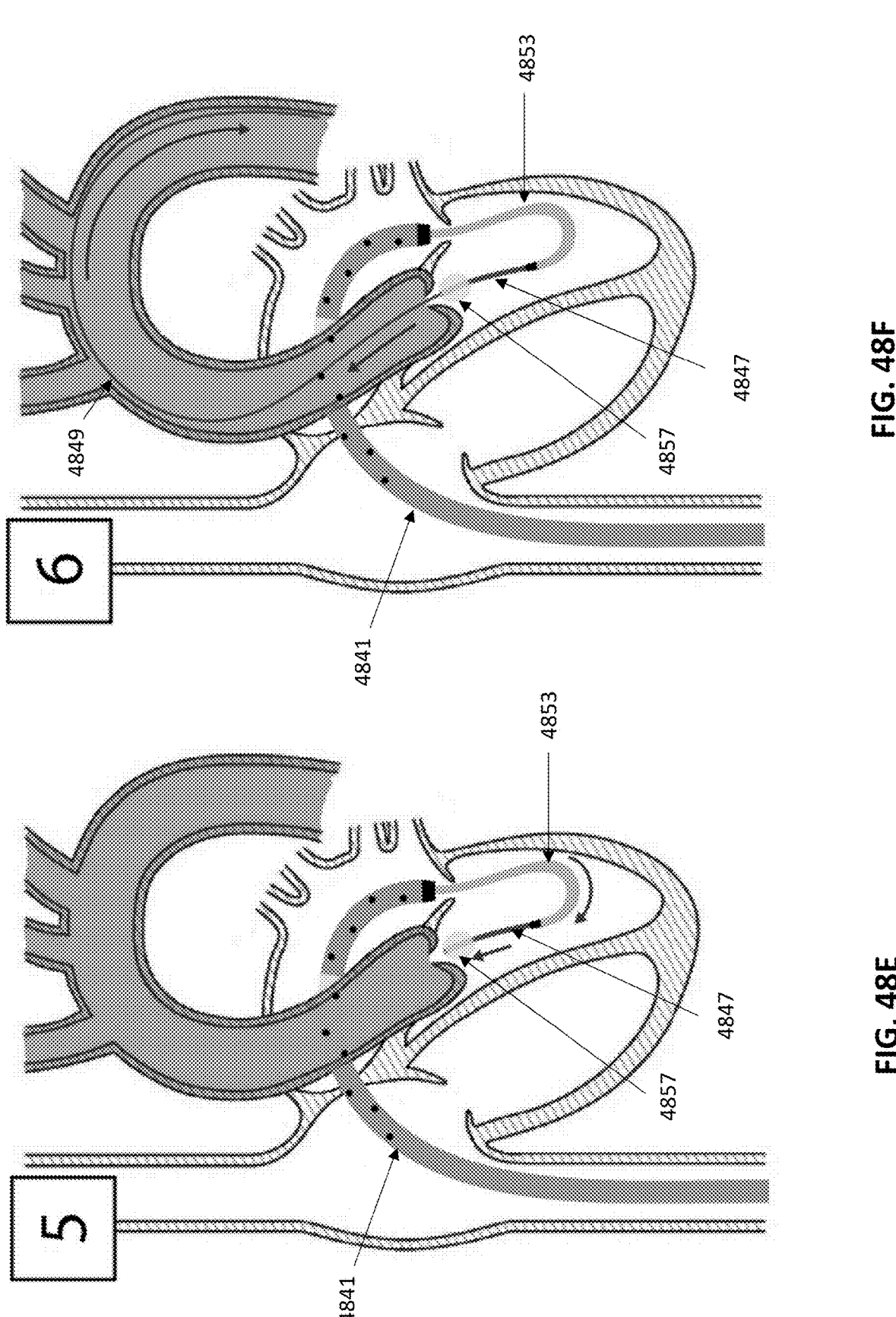

In FIG. 48D, the atrial sheath daughter catheter 4853 may be advanced over the granddaughter catheter 4847 and across the MV and into the LV, as shown (the balloon on the granddaughter catheter may remain inflated. In FIG. 48E a daughter catheter 4853 may be advanced distally over the granddaughter and then steered to deflect the granddaughter (including balloon 4857) 180°, and the granddaughter 4874 may then be advanced to the LV outflow track, as shown in FIG. 48E. The expanded balloon 4857 may prevent harm to the chordae tendinea and may help center the arterial sheath set, as shown in FIG. 48F. Once positioned at the valve, a guidewire, which may be the same guidewire or a different guidewire (specifically, a stiffer guidewire) than the first guidewire may be advanced across the aortic valve (AV) and into the descending aorta, as shown in FIG. 48F.

Figures 48G, 48H:
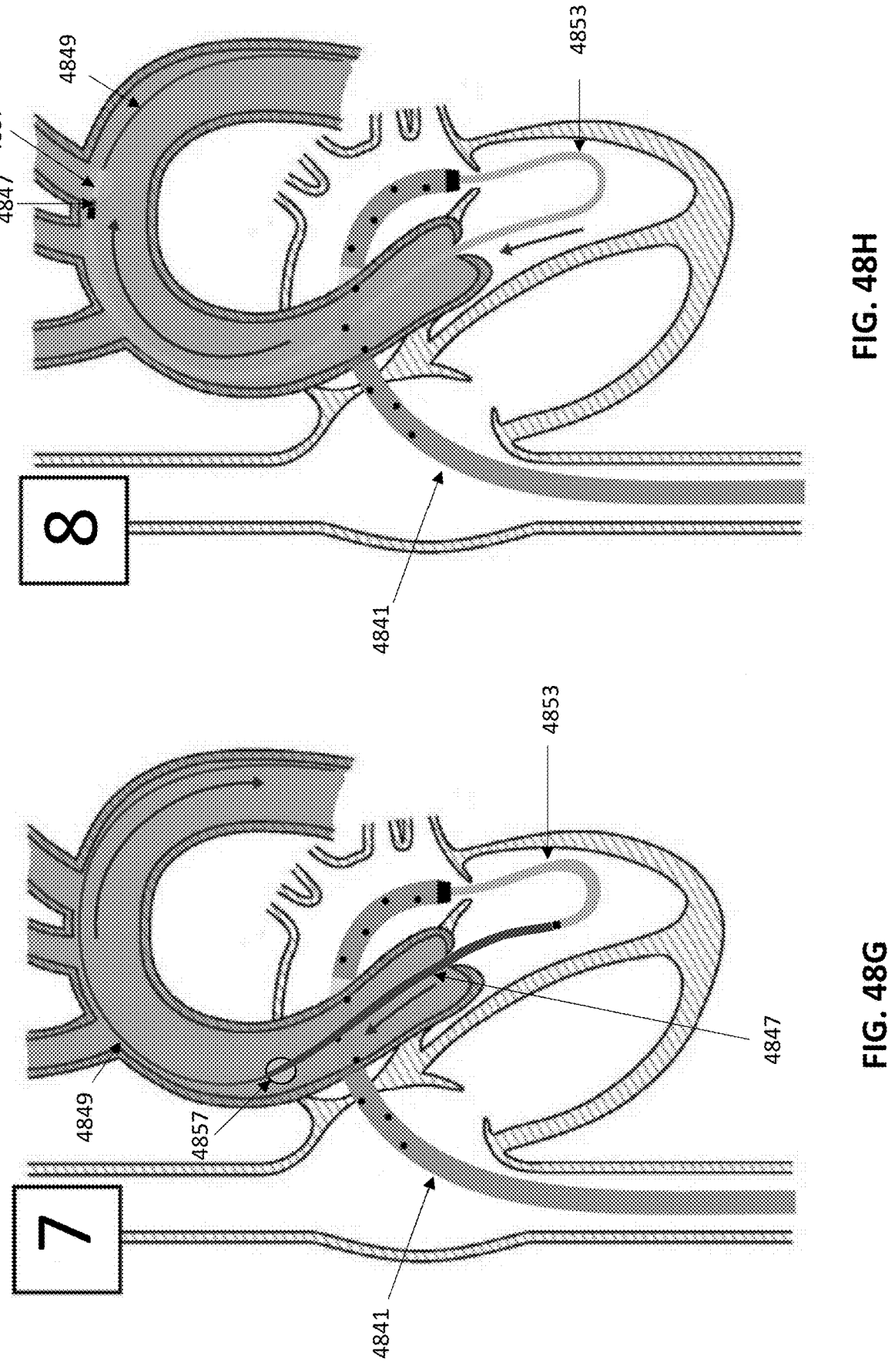
Figure 48J:
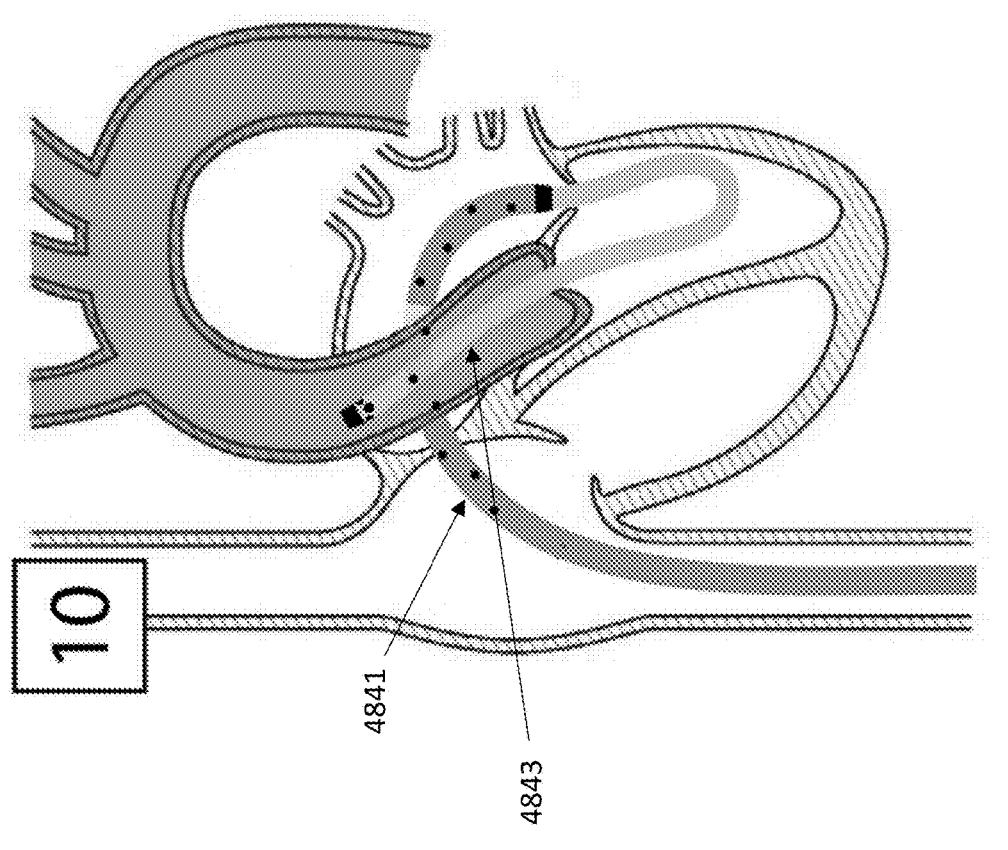
Figure 48I:
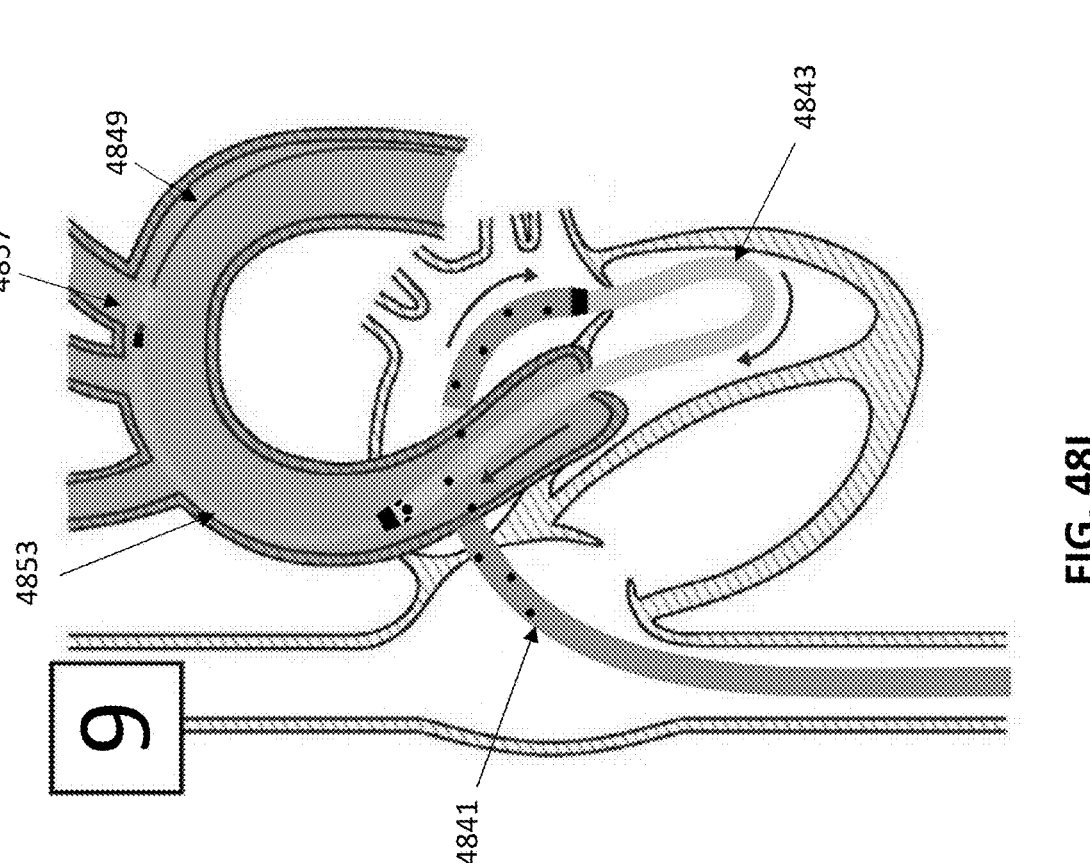

A second inner arterial catheter (e.g., granddaughter catheter) 4847 may then be advanced over the guidewire, through the first inner catheter (daughter catheter) 4853 and into the ascending aorta, optionally with a distal expander (e.g., ballon) 4857 partially or fully inflated, as shown in FIG. 48G. In FIG. 48G the granddaughter catheter 4847 is advanced across the AV to the left subclavian artery. In FIG. 48H, the daughter catheter 4853 is advanced over the granddaughter catheter 4847. In some examples the guidewire may be swapped for a stiffer guidewire 4849' and introduced prior to advancing the granddaughter/daughter catheter(s) to provide additional support. In FIG. 48I the mother catheter (e.g., the arterial sheath 4843) may then be advanced over the daughter 4853 and granddaughter 4847 into the descending aorta. Once the distal end of the mother (arterial sheath) 4843 is positioned, the daughter 4853 and granddaughter 4847 catheters (and optionally the guidewire 4849) may be withdrawn proximally (after collapsing the expander, e.g., balloon 4857) and completely withdrawn, and the arterial sheath may be positioned within the ascending aorta, as shown in FIG. 48J. The nested arterial sheath and venous sheath may then be used to with a LAVA-ECMO system as described above.

Any of these apparatuses may be used with a large sheath that is first advanced into the left atrium. This sheath may be steerable in at least one plane and may be centered and deflected above the central access of the mitral valve. The entire ECMO system, including the outer venous sheath and inner arterial sheath or additional catheters as described above may be advanced through such a large (e.g., 24 F or 25 F or larger sheath) and passed to aorta as described above. This large deflectable "grandmother" sheath may allow back up and coaxial alignment for passage through the heart and also can be hooked up as the venous return. In some cases, the sheath can have side holes to allow venous blood return and left atrial blood return so the side holes may be positioned in the left atrium and the right atrium and or inferior vena cava to return the venous blood to the ECMO pump and then the arterial blood is returned through the 18 F or 20 F ECMO sheath.

In general, the apparatuses described herein may allow a LAVA decompression of the entire heart and a single venous entry point to provide both venous and arterial return to the ECMO pump.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

When a feature or element is herein referred to as being "on" another feature or element, it can be directly on the other feature or element, or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for performing transseptal extracorporeal membrane oxygenation (ECMO) on a patient, the method comprising:

introducing an arterial sheath catheter through a right atrium and into a patient's heart via an arterial access site;

advancing a daughter inner catheter through the arterial sheath catheter and into a left atrium;

advancing a granddaughter inner catheter out of a lumen of the daughter inner catheter and into the left ventricle with a balloon at a distal end of the granddaughter inner catheter at least partially expanded;

deflecting a distal end region of the granddaughter inner catheter towards an aortic valve;

advancing the granddaughter inner catheter distally across the aortic valve and into an ascending aortic arch;

advancing the daughter inner catheter distally into the ascending aortic arch;

advancing the arterial sheath catheter over the daughter inner catheter until the arterial sheath catheter is at least 1 cm distal to the aortic valve; and receiving, from the patient, oxygen-poor blood through a venous sheath catheter and returning oxygenated blood through the arterial sheath catheter to the ascending aortic arch.

2. The method of claim 1, wherein deflecting the granddaughter inner catheter comprises advancing the daughter inner catheter over the granddaughter inner catheter and deflecting the daughter inner catheter to deflect the granddaughter inner catheter.

3. The method of claim 1, wherein advancing the daughter inner catheter comprises advancing the daughter inner catheter distally over the granddaughter inner catheter into the ascending aortic arch.

4. The method of claim 1, wherein advancing the arterial sheath catheter over the daughter inner catheter comprises advancing the arterial sheath catheter over the daughter inner catheter and granddaughter inner catheter.

5. The method of claim 1, further comprising withdrawing the daughter inner catheter and granddaughter inner catheter through the arterial sheath catheter before returning oxygenated blood through the arterial sheath catheter.

6. The method of claim 1, wherein deflecting the distal end region of the granddaughter inner catheter comprises actuating a deflection mechanism comprising a pullwire extending through the daughter inner catheter to deflect the distal end region of the daughter inner catheter.

7. The method of claim 1, further comprising delivering a guidewire through the granddaughter inner catheter into the left ventricle before advancing the granddaughter inner catheter.

8. The method of claim 1, further comprising delivering a guidewire through the granddaughter inner catheter and into the ascending aorta before advancing the granddaughter inner catheter into the ascending aorta.

9. The method of claim 1, further comprising advancing the venous sheath catheter over the mother catheter.

10. The method of claim 9, wherein advancing the venous sheath catheter comprises sealing the venous sheath catheter to an outer surface of the arterial sheath catheter.

11. The method of claim 1, further comprising positioning the venous sheath catheter in an inferior vena cava.

12. The method of claim 1, wherein the granddaughter inner catheter includes a low durometer deflection jacket that allows asymmetric compression of an inner shaft under pull wire tension.

13. The method of claim 1, further comprising positioning the venous sheath catheter so that a plurality of inflow openings on the venous sheath catheter are positioned within the right atrium, the left atrium, or both the right atrium and left atrium.

14. The method of claim 1, wherein the daughter inner catheter includes a laser-cut hypotube with a spine to control planar deflection.

15. The method of claim 1, further comprising visualizing a radiopaque distal tip and a mid-shaft marker band on the granddaughter inner catheter.

16. The method of claim 1, further comprising coupling the arterial sheath catheter and the venous sheath catheter to an ECMO pump device and performing ECMO.

17. A method for performing transseptal extracorporeal membrane oxygenation (ECMO) on a patient, the method comprising:
    introducing an arterial sheath catheter through a right atrium and into a patient's heart via an arterial access site;
    advancing a daughter inner catheter through the arterial sheath catheter and into a left atrium;
    advancing a granddaughter inner catheter out of a lumen of the daughter inner catheter and into the left ventricle with a balloon at a distal end of the granddaughter inner catheter expanded;
    advancing the daughter inner catheter over the granddaughter inner catheter;
    deflecting a distal end region of the granddaughter inner catheter towards an aortic valve;
    advancing the granddaughter inner catheter distally out of the daughter inner catheter across the aortic valve and into the ascending aorta;
    advancing the daughter inner catheter distally over the granddaughter inner catheter into the ascending aorta;
    advancing the arterial sheath catheter over the daughter inner catheter and granddaughter inner catheter until the arterial sheath catheter is at least 1 cm distal to the aortic valve; and
    receiving, from the patient, oxygen-poor blood through a venous sheath catheter and returning oxygenated blood through the arterial sheath catheter to the ascending aortic arch.

18. The method of claim 17, further comprising positioning the venous sheath catheter so that a plurality of inflow openings on the venous sheath catheter are positioned within the right atrium, the left atrium, or both the right atrium and left atrium.

19. The method of claim 17, further comprising coupling the arterial sheath catheter and the venous sheath catheter to an ECMO pump device and performing ECMO.

20. A method for performing transseptal extracorporeal membrane oxygenation (ECMO) on a patient, the method comprising:
    introducing an arterial sheath catheter through a right atrium and into a patient's heart via an arterial access site;
    advancing a daughter inner catheter through the arterial sheath catheter and into a left atrium;
    advancing a granddaughter inner catheter out of a lumen of the daughter inner catheter and into the left ventricle with a balloon at a distal end of the granddaughter inner catheter at least partially expanded;
    deflecting a distal end region of the granddaughter inner catheter towards an aortic valve;
    advancing the granddaughter inner catheter distally across the aortic valve and into an ascending aortic arch;
    advancing the daughter inner catheter distally into the ascending aortic arch;
    advancing the arterial sheath catheter over the daughter inner catheter until the arterial sheath catheter is at least 1 cm distal to the aortic valve;
    positioning a venous sheath catheter so that a plurality of inflow openings on the venous sheath catheter are positioned within the right atrium, the left atrium, or both the right atrium and left atrium; and
    receiving, from the patient, oxygen-poor blood through the venous sheath catheter and returning oxygenated blood through the arterial sheath catheter to the ascending aortic arch.

* * * * *